(12) United States Patent
Jin

(10) Patent No.: US 11,313,865 B2
(45) Date of Patent: Apr. 26, 2022

(54) NUCLEIC ACIDS ENCODING ANTI-HCTNT-N69 ANTIBODIES

(71) Applicant: Wayne State University, Detroit, MI (US)

(72) Inventor: Jian-Ping Jin, Chicago, IL (US)

(73) Assignee: Wayne State University, Detroit, MI (US)

( * ) Notice: Subject to any disclaimer, the term of this patent is extended or adjusted under 35 U.S.C. 154(b) by 97 days.

(21) Appl. No.: 16/861,897

(22) Filed: Apr. 29, 2020

(65) Prior Publication Data

US 2020/0319206 A1 Oct. 8, 2020

Related U.S. Application Data

(62) Division of application No. 16/009,904, filed on Jun. 15, 2018, now Pat. No. 10,648,987.

(60) Provisional application No. 62/548,052, filed on Aug. 21, 2017, provisional application No. 62/520,250, filed on Jun. 15, 2017.

(51) Int. Cl.
| | |
|---|---|
| *C07K 16/18* | (2006.01) |
| *G01N 33/68* | (2006.01) |
| *G01N 33/53* | (2006.01) |
| *C07K 14/47* | (2006.01) |

(52) U.S. Cl.
CPC ......... *G01N 33/6887* (2013.01); *C07K 16/18* (2013.01); *G01N 33/53* (2013.01); *C07K 14/4702* (2013.01); *C07K 2317/56* (2013.01); *G01N 2333/4712* (2013.01); *G01N 2800/32* (2013.01)

(58) Field of Classification Search
CPC . C07K 16/18; C07K 14/4702; C07K 2317/56
See application file for complete search history.

(56) References Cited

PUBLICATIONS

Wells (1990) "Additivity of Mutational Effects in Proteins." Biochemistry 29(37): 8509-8517.*

Ngo et al (1995) "The Protein Folding Problem and Tertiary Structure Prediction, Chapter 14: Computational Complexity Protein Structure Prediction, and the Levinthal Paradox" pp. 492-495.*
Jin, J. et al., Isoform Diversity, Regulation, and Functional Adaptation of Troponin and Calponin, *Critical Reviews in Eukaryotic Gene Expression*, 18(2): 93-124, 2008.
Wei, B. et al., TNNT1, TNNT2, and TNNT3: Isoform Genes, Regulation, and Structure-Function Relationships, Gene, 582(1): 1-13, May 10, 2016.
Zhang, Z. et al., Selective deletion of the NH2-terminal variable region of cardiac troponin T in ischemia reperfusion by myofibril-associated mu-calpain cleavage, Biochemistry, 45(38):11681-94, Sep. 26, 2006.
Feng, H. et al., Restricted N-terminal truncation of cardiac troponin T: a novel mechanism for functional adaptation to energetic crisis, J Physiol., 14: 3537-3550, 2008.
Benjamini, E., Immunology: A Short Course, 2nd edition, p. 40, 1991.
Ferrara, F. et al., Recombinant renewable polyclonal antibodies, mAbs, 7(1): 32-41, 2015.

* cited by examiner

*Primary Examiner* — Zachary C Howard
(74) *Attorney, Agent, or Firm* — Julie K. Staple; Dinsmore & Shohl LLP

(57) ABSTRACT

Methods for detecting a cardiac condition in a human subject are provided according to aspects of the present invention which include providing an immunological reagent characterized by specific binding to: an N-terminal fragment of human cardiac troponin T (HcTnT-N69) or a neoepitope of human cardiac troponin T generated by removal of HcTnT-N69 from HcTnT (HcTnT-neo); contacting the immunological reagent with a biological sample of the human subject under binding conditions; and detecting binding of the immunological reagent with HcTnT-N69 or HcTnT-neo, wherein detection of HcTnT-N69 or HcTnT-neo in the biological sample is indicative of a cardiac condition in the subject. Antibodies and antigen binding fragments thereof characterized by specific binding to HcTnT-N69 or HcTnT-neo, or a variant of either thereof, are provided according to aspects of the present invention.

3 Claims, 11 Drawing Sheets

Specification includes a Sequence Listing.

VH Variant 1: mAbs 1D6, 2A8, 2C1, 2D11, 2F11, 3F3

VH Variant 1 (IgG1): GPELVKPGASVKISCKTSGYTFTENTIHWKQSHGKSLEWVGGIN-P-NNGGTNYNQKFKGRAALTVD
Unrelated IgG1 VH:   GAELVRPGTSVKVSCKAFGYAFSNYLIEWVQQRHGQGLEGIGVMIYPGSGDHK-YNEKFKGKATLTAD VH Variant 1 (IgG1): KSSSTAYMELRSLTSEDSAVYYCARSW-D---WFAYWGQGTLVTVSA(SEQ ID NO:2)
Unrelated IgG1 VH:   KSSSTAYMQLSSLTSDDSAVYFCARFDYDVTYAMAYWGQGTSATV (accession # S59138.1;
SEQ ID NO:25)

38.9% (44/113) of the aligned residues are non-conserved; Conserved residues are underlined in the reference sequence VH Variant 2: mAbs 1E11, 3B6, 3E5

VH Variant 2 (IgG3): GAELAKPGASVKMSCKASGYTFTTYWMHWKQRPGQGLEWIGFINP--STGYT-EYNQKFKDKATLTAD
Unrelated IgG3 VH:   GGGLVQPGGSMKLSCVASEFTFNNYWMNWVRQSPEKGLEWVAEIRLKSNNYATHYAESVKGRFTISRD VH Variant 2 (IgG3): KSSSTAYMQLSSLTSGDSAVYYCAR-KSFAYWGHGTLVTVSAATTTA (SEQ ID NO:8)
Unrelated IgG3 VH:   DSKSSVYLQMNNLRAEDTGIYYCTSNVAMDYWGQGTTVTVSS (accession # DQ273284.1;
SEQ ID NO:26)

54.5% (60/110) of the aligned residues are non-conserved; Conserved residues are underlined in the reference sequence VH Variant 3: mAbs 3H5, 2H3, 4F5, 2D9

VH Variant 3 (IgM): GGGLVQPKGSLKLSCAASGFTFNTYAMNWVRQAPGKGLEWVARIRSK-SNNYATYYADSVKDRFTISRD
Unrelated IgM VH:   GLVAPSQSLSITCTVSGFSLTSYGVHWVRQPPGKGLEWLGVIWAGGSTNYNSA-LMS-RLSISKG-D VH Variant 3 (IgM): DSQSMLYLQMNNLKTEDTAMYYCVRHDGVAWFAYWGQGTLVTVSA (SEQ ID NO:12)
Unrelated IgM VH:   NSKSQVFLKMNSLQTDDTAMYYCARCYYGSHFDYWGQGTTLTVSS (accession # M77137.1;
SEQ ID NO:27)

50.9% (57/112) of the aligned residues are non-conserved; Conserved residues are underlined in the reference sequence.

FIG. 10

```
VL Variants (kappa):

VL Variant 1:        LSLPVSLGDQASISCRSSQSLVHSNGNT-YLHWYLQKPGQSPKLLVYKVSNRFSGVPDRFSGSGSGTDF
VL Variant 2:        LSLPVSLGDQASISCRSSQSLVHSNGNT-YLHWYLQKPGQSPKLLVYKVSNRFSGVPDRFSGSGSGTDF
VL Variant 3:        LTLSVTIGQPASISCKSSQSLLHSDGKT-YLNWLLQRPGQSPKRLIYLVSKLDSGVPDRFTGSGSGTDF
VL Variant 4:        LSLPVSLGDQASISCRSSQSIVHSNGNT-YLEWYLQKPGQSPKLLIYKVSNRFSGVPDRFSGSGSGTDF
VL Variant 5:        LSLPVSLGDQASISCRSSQSIVHSNGNT-YLEWYLQKPGQSPKLLIYKVSNRFSGVPDRFSGSGSGTDF
VL Variant 6:        LSLPVSLGDQASISCKSSQSIVHSNGNT-YLEWYLQKPGQSPKLLIYKVSNRFSGVPDRFSGSGSGTDF
VL Variant 7:        LSLPVSLGDQASISCKSSQSIVHSNGNT-YLKWYLQKPGQSPKLLIYKVSNRFSGVPDRFSGSGSGTDF
Anti-N69 Consensus:  lslpvslgdqasisckssqsivhsngnt-ylewylqrpgqspklliykvsnrfsgvpdrfsgsgsgtdf
     Substitutions:   t s ti qp          ll  d k    h l          r v l kld       t
                                                    n
                                                    k Unrelated kappa VL:  SSLAVSAGEKVTMSCKSSQSLLNSRTRKNYLAWYQQKPGQSPKLLIYWASSRESGVPDRFTGSGSGTDF (Continued)
VL Variant 1:        TLKIIRVEAEDLGVYFCSQSTRIPFTFGSGTKLEMKRA  (SEQ ID NO:3) mAbs 1D6, 2A8, 2C1
VL Variant 2:        TLKIIRVKAEDLGVYFCSQSTRIPFTFGSGTKLEMKRA  (SEQ ID NO:6) mAbs 2D11, 2F11, 3F3
VL Variant 3:        TLKISRVEAEDVGIYYCWQGTQFPRTFGGGTKLEIKRA  (SEQ ID NO:9) mAbs 1E11, 3B6, 3E5
VL Variant 4:        TLKISRVEAEDLGVYYCFQGSHVPPTFGAGTKLELKRA  (SEQ ID NO:13) mAb 3H5
VL Variant 5:        TLKISRVKAEDLGVYYCFQGSHVPPTFGAGTKLELKRA  (SEQ ID NO:16) mAb 2H3
VL Variant 6:        TLKISRVKAEDLGVYYCFQGSHVPPTFGAGTKLELKRA  (SEQ ID NO:18) mAb 4F5
VL Variant 7:        TLKISRVKAEDLGVYYCFQGSHVPPTFGAGTKLELKRA  (SEQ ID NO:20) mAb 2D9
Anti-N69 Consensus:  tlkisrvkaedlgvyycfqgshvpptfgagtklelk    (SEQ ID NO:29)
     Substitutions:      i  e   v i f s stri f  s    m
                                      w  qf r  g    i Unrelated kappa VL:  TLTISSVQAEDLAVYYCKQSYNL-YTFGGGTKLEIK  (accession # Z22039.1; SEQ ID NO:28)
```

Conserved residues are underlined in the reference sequence. The shaded residues are different among the anti-N69 mAbs.

Percent of the aligned residues which are non-conserved:

Variant 1: 34.3% (36/105)
Variant 2: 34.3% (36/105)
Variant 3: 34.3% (36/105)
Variant 4: 33.3% (35/105)
Variant 5: 33.3% (35/105)
Variant 6: 33.3% (35/105)
Variant 7: 33.3% (35/105)

FIG. 11

SEQUENCE LISTING

```
<160> NUMBER OF SEQ ID NOS: 30

<210> SEQ ID NO 1
<211> LENGTH: 69
<212> TYPE: PRT
<213> ORGANISM: Homo sapiens

<400> SEQUENCE: 1

Met Ser Asp Leu Glu Glu Val Val Glu Glu Tyr Glu Glu Glu Glu
1               5                   10                  15

Gln Glu Glu Ala Ala Val Glu Val Gln Glu Glu Ala Ala Glu Glu Asp
                20                  25                  30

Ala Glu Ala Glu Ala Glu Thr Glu Glu Thr Arg Ala Glu Glu Asp Glu
            35                  40                  45

Glu Glu Glu Glu Ala Lys Glu Ala Glu Asp Gly Pro Met Glu Glu Ser
        50                  55                  60

Lys Pro Lys Pro Arg
65

<210> SEQ ID NO 2
<211> LENGTH: 109
<212> TYPE: PRT
<213> ORGANISM: Artificial Sequence
<220> FEATURE:
<223> OTHER INFORMATION: Amino acid sequence of variable heavy chain
      region of mAb 1D6

<400> SEQUENCE: 2

Gly Pro Glu Leu Val Lys Pro Gly Ala Ser Val Lys Ile Ser Cys Lys
1               5                   10                  15

Thr Ser Gly Tyr Thr Phe Thr Glu Asn Thr Ile His Trp Val Lys Gln
                20                  25                  30

Ser His Gly Lys Ser Leu Glu Trp Val Gly Gly Ile Asn Pro Asn Asn
            35                  40                  45

Gly Gly Thr Asn Tyr Asn Gln Lys Phe Lys Gly Arg Ala Ala Leu Thr
        50                  55                  60

Val Asp Lys Ser Ser Ser Thr Ala Tyr Met Glu Leu Arg Ser Leu Thr
65                  70                  75                  80

Ser Glu Asp Ser Ala Val Tyr Tyr Cys Ala Arg Ser Trp Asp Trp Phe
                85                  90                  95

Ala Tyr Trp Gly Gln Gly Thr Leu Val Thr Val Ser Ala
            100                 105

<210> SEQ ID NO 3
<211> LENGTH: 106
```

<212> TYPE: PRT
<213> ORGANISM: Artificial Sequence
<220> FEATURE:
<223> OTHER INFORMATION: Amino acid sequence of variable light chain
      region of mAb 1D6

<400> SEQUENCE: 3

Leu Ser Leu Pro Val Ser Leu Gly Asp Gln Ala Ser Ile Ser Cys Arg
1               5                   10                  15

Ser Ser Gln Ser Leu Val His Ser Asn Gly Asn Thr Tyr Leu His Trp
            20                  25                  30

Tyr Leu Gln Lys Pro Gly Gln Ser Pro Lys Leu Leu Val Tyr Lys Val
        35                  40                  45

Ser Asn Arg Phe Ser Gly Val Pro Asp Arg Phe Ser Gly Ser Gly Ser
    50                  55                  60

Gly Thr Asp Phe Thr Leu Lys Ile Ile Arg Val Glu Ala Glu Asp Leu
65                  70                  75                  80

Gly Val Tyr Phe Cys Ser Gln Ser Thr Arg Ile Pro Phe Thr Phe Gly
                85                  90                  95

Ser Gly Thr Lys Leu Glu Met Lys Arg Ala
            100                 105

<210> SEQ ID NO 4
<211> LENGTH: 327
<212> TYPE: DNA
<213> ORGANISM: Artificial Sequence
<220> FEATURE:
<223> OTHER INFORMATION: nucleotide sequence encoding variable heavy
      chain region of mAb 1D6

<400> SEQUENCE: 4
ggacctgaac tggtgaagcc tggggcttca gtgaagattt cctgtaagac ttctggatac      60
acattcactg aaaacaccat acactgggtg aagcagagcc atggaaagag ccttgagtgg     120
gttggaggta tcaatcctaa caatggtggc actaattaca atcagaaatt taagggcagg     180
gccgcattga ctgtagacaa gtcctccagc acagcctaca tggagctccg cagcctgaca     240
tctgaagatt ctgcagtcta ttattgtgca agatcctggg actggtttgc ttactggggc     300
caagggactc tggtcactgt ctctgca                                         327

<210> SEQ ID NO 5
<211> LENGTH: 318
<212> TYPE: DNA
<213> ORGANISM: Artificial Sequence
<220> FEATURE:
<223> OTHER INFORMATION: nucleotide sequence encoding variable light
      chain region of mAb 1D6

<400> SEQUENCE: 5
ctctccctgc ctgtcagtct tggagatcag gcctccatct cttgcagatc tagtcagagc      60
cttgtacaca gtaatggaaa cacctattta cattggtacc tgcagaagcc aggccagtct     120
ccaaagctcc tggtctacaa agtttccaac cgattttctg ggtcccaga caggttcagt      180 ggcagtggat cagggacaga tttcacactc aagatcatca gagtggaggc tgaggatctg     240
ggagtttatt tctgctctca agtacacgt attccattca cgttcggctc ggggacaaag     300
ttggaaatga aacgggct                                                   318

<210> SEQ ID NO 6
<211> LENGTH: 106
<212> TYPE: PRT

<213> ORGANISM: Artificial Sequence
<220> FEATURE:
<223> OTHER INFORMATION: Amino acid sequence of variable light chain
      region of mAb 2D11

<400> SEQUENCE: 6

```
Leu Ser Leu Pro Val Ser Leu Gly Asp Gln Ala Ser Ile Ser Cys Arg
1               5                   10                  15

Ser Ser Gln Ser Leu Val His Ser Asn Gly Asn Thr Tyr Leu His Trp
            20                  25                  30

Tyr Leu Gln Lys Pro Gly Gln Ser Pro Lys Leu Leu Val Tyr Lys Val
        35                  40                  45

Ser Asn Arg Phe Ser Gly Val Pro Asp Arg Phe Ser Gly Ser Gly Ser
    50                  55                  60

Gly Thr Asp Phe Thr Leu Lys Ile Ile Arg Val Lys Ala Glu Asp Leu
65                  70                  75                  80

Gly Val Tyr Phe Cys Ser Gln Ser Thr Arg Ile Pro Phe Thr Phe Gly
                85                  90                  95

Ser Gly Thr Lys Leu Glu Met Lys Arg Ala
            100                 105
```

<210> SEQ ID NO 7
<211> LENGTH: 318
<212> TYPE: DNA
<213> ORGANISM: Artificial Sequence
<220> FEATURE:
<223> OTHER INFORMATION: nucleotide sequence encoding variable light
      chain region of mAb 2D11

<400> SEQUENCE: 7

```
ctctccctgc ctgtcagtct tggagatcag gcctccatct cttgcagatc tagtcagagc    60
cttgtacaca gtaatggaaa cacctattta cattggtacc tgcagaagcc aggccagtct   120
ccaaagctcc tggtctacaa agtttccaac cgatttttctg ggtcccaga caggttcagt   180 ggcagtggat cagggacaga tttcacactc aagatcatca gagtgaaggc tgaggatctg   240
ggagtttatt tctgctctca agtacacgt attccattca cgttcggctc ggggacaaag   300
ttggaaatga aacgggct                                                 318
```

<210> SEQ ID NO 8
<211> LENGTH: 112
<212> TYPE: PRT
<213> ORGANISM: Artificial Sequence
<220> FEATURE:
<223> OTHER INFORMATION: Amino acid sequence of variable heavy chain
      region of mAb 1E11

<400> SEQUENCE: 8

```
Gly Ala Glu Leu Ala Lys Pro Gly Ala Ser Val Lys Met Ser Cys Lys
1               5                   10                  15

Ala Ser Gly Tyr Thr Phe Thr Thr Tyr Trp Met His Trp Val Lys Gln
            20                  25                  30

Arg Pro Gly Gln Gly Leu Glu Trp Ile Gly Phe Ile Asn Pro Ser Thr
        35                  40                  45

Gly Tyr Thr Glu Tyr Asn Gln Lys Phe Lys Asp Lys Ala Thr Leu Thr
    50                  55                  60

Ala Asp Lys Ser Ser Ser Thr Ala Tyr Met Gln Leu Ser Ser Leu Thr
65                  70                  75                  80

Ser Gly Asp Ser Ala Val Tyr Tyr Cys Ala Arg Lys Ser Phe Ala Tyr
                85                  90                  95
```

```
Trp Gly His Gly Thr Leu Val Thr Val Ser Ala Ala Thr Thr Thr Ala
            100                 105                 110
```

<210> SEQ ID NO 9
<211> LENGTH: 106
<212> TYPE: PRT
<213> ORGANISM: Artificial Sequence
<220> FEATURE:
<223> OTHER INFORMATION: Amino acid sequence of variable heavy chain
      region of mAb 1E11

<400> SEQUENCE: 9

```
Leu Thr Leu Ser Val Thr Ile Gly Gln Pro Ala Ser Ile Ser Cys Lys
1               5                   10                  15

Ser Ser Gln Ser Leu Leu His Ser Asp Gly Lys Thr Tyr Leu Asn Trp
            20                  25                  30

Leu Leu Gln Arg Pro Gly Gln Ser Pro Lys Arg Leu Ile Tyr Leu Val
        35                  40                  45

Ser Lys Leu Asp Ser Gly Val Pro Asp Arg Phe Thr Gly Ser Gly Ser
    50                  55                  60

Gly Thr Asp Phe Thr Leu Lys Ile Ser Arg Val Glu Ala Glu Asp Val
65                  70                  75                  80

Gly Ile Tyr Tyr Cys Trp Gln Gly Thr Gln Phe Pro Arg Thr Phe Gly
                85                  90                  95

Gly Gly Thr Lys Leu Glu Ile Lys Arg Ala
            100                 105
```

<210> SEQ ID NO 10
<211> LENGTH: 336
<212> TYPE: DNA
<213> ORGANISM: Artificial Sequence
<220> FEATURE:
<223> OTHER INFORMATION: nucleotide sequence encoding variable heavy
      chain region of mAb 1E11

<400> SEQUENCE: 10

```
ggggctgaac tggcaaaacc tggggcctca gtgaagatgt cctgcaaggc ttctggttac    60
acctttacta cttactggat gcactgggta aaacagaggc ctggacaggg tctggaatgg   120
attggattca ttaatcctag tactggttat actgaataca atcagaagtt caaggacaag   180
gccacattga ctgcagacaa atcctccagc acagcctaca tgcaactgag cagcctgaca   240
tctggggact ctgcagtcta ttactgtgca agaaagagtt ttgcttactg gggccacggg   300
actctggtca ctgtctctgc agctacaaca acagcc                             336
```

<210> SEQ ID NO 11
<211> LENGTH: 318
<212> TYPE: DNA
<213> ORGANISM: Artificial Sequence
<220> FEATURE:
<223> OTHER INFORMATION: nucleotide sequence encoding variable light
      chain region of mAb 1E11

<400> SEQUENCE: 11

```
ctcactttgt cggttaccat tggacaacca gcctccatct cttgcaagtc aagtcagagc    60
ctcttacata gtgatggaaa gacatatttg aattggttgt tacagaggcc aggccagtct   120
ccaaagcgcc taatctatct ggtgtctaaa ctggactctg gagtccctga caggttcact   180
ggcagtggat cagggacaga tttcacactg aaaatcagca gagtggaggc tgaggatgtg   240
ggaatttatt attgctggca agtacacaa tttcctcgga cgttcggtgg aggcaccaag   300
```
ctggaaatca aacgggct                                                318

<210> SEQ ID NO 12
<211> LENGTH: 113
<212> TYPE: PRT
<213> ORGANISM: Artificial Sequence
<220> FEATURE:
<223> OTHER INFORMATION: Amino acid sequence of variable heavy chain
      region of mAb 3H5

<400> SEQUENCE: 12

```
Gly Gly Gly Leu Val Gln Pro Lys Gly Ser Leu Lys Leu Ser Cys Ala
1               5                   10                  15

Ala Ser Gly Phe Thr Phe Asn Thr Tyr Ala Met Asn Trp Val Arg Gln
            20                  25                  30

Ala Pro Gly Lys Gly Leu Glu Trp Val Ala Arg Ile Arg Ser Lys Ser
        35                  40                  45

Asn Asn Tyr Ala Thr Tyr Tyr Ala Asp Ser Val Lys Asp Arg Phe Thr
    50                  55                  60

Ile Ser Arg Asp Asp Ser Gln Ser Met Leu Tyr Leu Gln Met Asn Asn
65                  70                  75                  80

Leu Lys Thr Glu Asp Thr Ala Met Tyr Tyr Cys Val Arg His Asp Gly
                85                  90                  95

Val Ala Trp Phe Ala Tyr Trp Gly Gln Gly Thr Leu Val Thr Val Ser
            100                 105                 110

Ala
```

<210> SEQ ID NO 13
<211> LENGTH: 106
<212> TYPE: PRT
<213> ORGANISM: Artificial Sequence
<220> FEATURE:
<223> OTHER INFORMATION: Amino acid sequence of variable light chain
      region of mAb 3H5

<400> SEQUENCE: 13

```
Leu Ser Leu Pro Val Ser Leu Gly Asp Gln Ala Ser Ile Ser Cys Arg
1               5                   10                  15

Ser Ser Gln Ser Ile Val His Ser Asn Gly Asn Thr Tyr Leu Glu Trp
            20                  25                  30

Tyr Leu Gln Lys Pro Gly Gln Ser Pro Lys Leu Leu Ile Tyr Lys Val
        35                  40                  45

Ser Asn Arg Phe Ser Gly Val Pro Asp Arg Phe Ser Gly Ser Gly Ser
    50                  55                  60

Gly Thr Asp Phe Thr Leu Lys Ile Ser Arg Val Glu Ala Glu Asp Leu
65                  70                  75                  80

Gly Val Tyr Tyr Cys Phe Gln Gly Ser His Val Pro Pro Thr Phe Gly
                85                  90                  95

Ala Gly Thr Lys Leu Glu Leu Lys Arg Ala
            100                 105
```

<210> SEQ ID NO 14
<211> LENGTH: 339
<212> TYPE: DNA
<213> ORGANISM: Artificial Sequence
<220> FEATURE:
<223> OTHER INFORMATION: nucleotide sequence encoding variable heavy
      chain region of mAb 3H5

<400> SEQUENCE: 14

```
ggtggaggat tggtgcagcc taaagggtca ttgaaactct catgtgcagc ctctggattc    60
accttcaata cctacgccat gaactgggtc cgccaggctc caggaaaggg tttggaatgg   120
gttgctcgca taagaagtaa aagtaataat tatgcaacat attatgccga ttcagtgaaa   180
gacaggttca ccatctccag agatgattca caaagcatgc tctatctgca aatgaacaac   240
ttgaaaactg aggacacagc catgtattac tgtgtgagac atgatggtgt cgcctggttt   300
gcttactggg gccaagggac tctggtcact gtctctgca                          339
```

```
<210> SEQ ID NO 15
<211> LENGTH: 318
<212> TYPE: DNA
<213> ORGANISM: Artificial Sequence
<220> FEATURE:
<223> OTHER INFORMATION: nucleotide sequence encoding variable light
      chain region of mAb 3H5

<400> SEQUENCE: 15
```

```
ctctccctgc ctgtcagtct tggagatcaa gcctccatct cttgcagatc tagtcagagc    60
attgtacata gtaatggaaa cacctattta gaatggtacc tgcagaaacc aggccagtct   120
ccaaagctcc tgatctacaa agtttccaac cgatttctg gggtcccaga caggttcagt    180
ggcagtggat cagggacaga tttcacactc aagatcagca gagtggaggc tgaggatctg   240
ggagtttatt actgctttca aggttcacat gttcctccca cgttcggtgc tgggaccaag   300
ctggagctga acgggct                                                  318
```

```
<210> SEQ ID NO 16
<211> LENGTH: 106
<212> TYPE: PRT
<213> ORGANISM: Artificial Sequence
<220> FEATURE:
<223> OTHER INFORMATION: Amino acid sequence of variable light chain
      region of mAb 2H3

<400> SEQUENCE: 16
```

```
Leu Ser Leu Pro Val Ser Leu Gly Asp Gln Ala Ser Ile Ser Cys Arg
1               5                   10                  15

Ser Ser Gln Ser Ile Val His Ser Asn Gly Asn Thr Tyr Leu Glu Trp
            20                  25                  30

Tyr Leu Gln Lys Pro Gly Gln Ser Pro Lys Leu Leu Ile Tyr Lys Val
        35                  40                  45

Ser Asn Arg Phe Ser Gly Val Pro Asp Arg Phe Ser Gly Ser Gly Ser
    50                  55                  60

Gly Thr Asp Phe Thr Leu Lys Ile Ser Arg Val Lys Ala Glu Asp Leu
65                  70                  75                  80

Gly Val Tyr Tyr Cys Phe Gln Gly Ser His Val Pro Pro Thr Phe Gly
                85                  90                  95

Ala Gly Thr Lys Leu Glu Leu Lys Arg Ala
            100                 105
```

```
<210> SEQ ID NO 17
<211> LENGTH: 318
<212> TYPE: DNA
<213> ORGANISM: Artificial Sequence
<220> FEATURE:
<223> OTHER INFORMATION: nucleotide sequence encoding variable light
      chain region of mAb 2H3

<400> SEQUENCE: 17
```

```
ctctccctgc ctgtcagtct tggagatcaa gcctccatct cttgcagatc tagtcagagc    60
attgtacata gtaatggaaa cacctattta gaatggtacc tgcagaaacc aggccagtct   120
ccaaagctcc tgatctacaa agtttccaac cgatttctg gggtcccaga caggttcagt   180
ggcagtggat cagggacaga tttcacactc aagatcagca gagtgaaggc tgaggatctg   240
ggagtttatt actgctttca aggttcacat gttcctccca cgttcggtgc tgggaccaag   300
ctggagctga aacgggct                                                 318
```

<210> SEQ ID NO 18
<211> LENGTH: 106
<212> TYPE: PRT
<213> ORGANISM: Artificial Sequence
<220> FEATURE:
<223> OTHER INFORMATION: Amino acid sequence of variable light chain
      region of mAb 4F5

<400> SEQUENCE: 18

```
Leu Ser Leu Pro Val Ser Leu Gly Asp Gln Ala Ser Ile Ser Cys Lys
1               5                  10                  15

Ser Ser Gln Ser Ile Val His Ser Asn Gly Asn Thr Tyr Leu Glu Trp
            20                  25                  30

Tyr Leu Gln Lys Pro Gly Gln Ser Pro Lys Leu Leu Ile Tyr Lys Val
        35                  40                  45

Ser Asn Arg Phe Ser Gly Val Pro Asp Arg Phe Ser Gly Ser Gly Ser
    50                  55                  60

Gly Thr Asp Phe Thr Leu Lys Ile Ser Arg Val Lys Ala Glu Asp Leu
65                  70                  75                  80

Gly Val Tyr Tyr Cys Phe Gln Gly Ser His Val Pro Pro Thr Phe Gly
                85                  90                  95

Ala Gly Thr Lys Leu Glu Leu Lys Arg Ala
            100                 105
```

<210> SEQ ID NO 19
<211> LENGTH: 318
<212> TYPE: DNA
<213> ORGANISM: Artificial Sequence
<220> FEATURE:
<223> OTHER INFORMATION: nucleotide sequence encoding variable light
      chain region of mAb 4F5

<400> SEQUENCE: 19

```
ctctccctgc ctgtcagtct tggagatcaa gcctccatct cttgcaaatc tagtcaaagc    60
attgtacata gtaatggaaa cacctattta gaatggtacc tgcagaaacc aggccagtct   120
ccaaagctcc tgatctacaa agtttccaac cgatttctg gggtcccaga caggttcagt   180
ggcagtggat cagggacaga tttcacactc aagatcagca gagtgaaggc tgaggatctg   240
ggagtttatt actgctttca aggttcacat gttcctccca cgttcggtgc tgggaccaag   300
ctggagctga aacgggct                                                 318
```

<210> SEQ ID NO 20
<211> LENGTH: 106
<212> TYPE: PRT
<213> ORGANISM: Artificial Sequence
<220> FEATURE:
<223> OTHER INFORMATION: Amino acid sequence of variable light chain
      region of mAb 2D9

<400> SEQUENCE: 20

```
Leu Ser Leu Pro Val Ser Leu Gly Asp Gln Ala Ser Ile Ser Cys Lys
```

```
                1               5                  10                  15
            Ser Ser Gln Ser Ile Val His Ser Asn Gly Asn Thr Tyr Leu Lys Trp
                            20                  25                  30

Tyr Leu Gln Lys Pro Gly Gln Ser Pro Lys Leu Leu Ile Tyr Lys Val
                        35                  40                  45

Ser Asn Arg Phe Ser Gly Val Pro Asp Arg Phe Ser Gly Ser Gly Ser
                    50                  55                  60

Gly Thr Asp Phe Thr Leu Lys Ile Ser Arg Val Lys Ala Glu Asp Leu
            65                  70                  75                  80

Gly Val Tyr Tyr Cys Phe Gln Gly Ser His Val Pro Pro Thr Phe Gly
                            85                  90                  95

Ala Gly Thr Lys Leu Glu Leu Lys Arg Ala
                        100                 105

<210> SEQ ID NO 21
<211> LENGTH: 318
<212> TYPE: DNA
<213> ORGANISM: Artificial Sequence
<220> FEATURE:
<223> OTHER INFORMATION: nucleotide sequence encoding variable light
      chain region of mAb 2D9

<400> SEQUENCE: 21 ctctcccctgc ctgtcagtct tggagatcaa gcctccatct cttgcagatc tagtcagagc      60
attgtacata gtaatggaaa cacctattta aatggtacc tgcagaaacc aggccagtct       120
ccaaagctcc tgatctacaa agtttccaac cgatttttctg gggtcccaga caggttcagt    180
ggcagtggat cagggacaga tttcacactc aagatcagca gagtgaaggc tgaggatctg     240
ggagtttatt actgctttca aggttcacat gttcctccca cgttcggtgc tgggaccaag    300
ctggagctga aacgggct                                                     318

<210> SEQ ID NO 22
<211> LENGTH: 42
<212> TYPE: PRT
<213> ORGANISM: Homo sapiens

<400> SEQUENCE: 22

Met Ser Asp Glu Glu Val Glu Gln Val Glu Glu Gln Tyr Glu Glu Glu
1               5                   10                  15

Glu Glu Ala Gln Glu Glu Glu Glu Val Gln Glu Asp Thr Ala Glu Glu
                20                  25                  30

Asp Ala Glu Glu Glu Lys Pro Arg Pro Lys
            35                  40

<210> SEQ ID NO 23
<211> LENGTH: 43
<212> TYPE: PRT
<213> ORGANISM: Homo sapiens

<400> SEQUENCE: 23

Met Ser Asp Thr Glu Glu Gln Glu Tyr Glu Glu Gln Pro Glu Glu
1               5                   10                  15

Glu Ala Ala Glu Glu Glu Glu Ala Pro Glu Pro Glu Pro Val
            20                  25                  30

Ala Glu Pro Glu Glu Glu Arg Pro Lys Pro Ser
            35                  40

<210> SEQ ID NO 24
```

```
<211> LENGTH: 43
<212> TYPE: PRT
<213> ORGANISM: Artificial Sequence
<220> FEATURE:
<223> OTHER INFORMATION: consensus sequence obtained by comparison of
      HcTnT-N69, HfTnT-N42, and HsTnT-N43.
<220> FEATURE:
<221> NAME/KEY: x
<222> LOCATION: (4)..(4)
<223> OTHER INFORMATION: X1 is L or T
<220> FEATURE:
<221> NAME/KEY: x
<222> LOCATION: (14)..(14)
<223> OTHER INFORMATION: X is E or Y
<220> FEATURE:
<221> NAME/KEY: x
<222> LOCATION: (14)..(14)
<223> OTHER INFORMATION: X is E or Y
<220> FEATURE:
<221> NAME/KEY: x
<222> LOCATION: (15)..(15)
<223> OTHER INFORMATION: X is Q or E or P
<220> FEATURE:
<221> NAME/KEY: x
<222> LOCATION: (19)..(19)
<223> OTHER INFORMATION: X is D or E or A
<220> FEATURE:
<221> NAME/KEY: x
<222> LOCATION: (26)..(26)
<223> OTHER INFORMATION: X is T or V or A
<220> FEATURE:
<221> NAME/KEY: x
<222> LOCATION: (29)..(29)
<223> OTHER INFORMATION: X is T or D or P
<220> FEATURE:
<221> NAME/KEY: x
<222> LOCATION: (30)..(30)
<223> OTHER INFORMATION: X is R or T or E
<220> FEATURE:
<221> NAME/KEY: x
<222> LOCATION: (35)..(35)
<223> OTHER INFORMATION: X is E or A or P
<220> FEATURE:
<221> NAME/KEY: x
<222> LOCATION: (43)..(43)
<223> OTHER INFORMATION: X is R or K or S

<400> SEQUENCE: 24

Met Ser Asp Xaa Glu Glu Val Glu Glu Tyr Glu Glu Glu Xaa Xaa Glu
1               5                   10                  15

Glu Glu Xaa Ala Glu Glu Glu Glu Xaa Glu Glu Xaa Xaa Ala Glu
            20                  25                  30

Glu Asp Xaa Glu Glu Glu Lys Pro Lys Pro Xaa
        35                  40

<210> SEQ ID NO 25
<211> LENGTH: 112
<212> TYPE: PRT
<213> ORGANISM: Artificial Sequence
<220> FEATURE:
<223> OTHER INFORMATION: unrelated IgG1 VH amino acid sequence
      (accession # S59138.1)

<400> SEQUENCE: 25

Gly Ala Glu Leu Val Arg Pro Gly Thr Ser Val Lys Val Ser Cys Lys
1               5                   10                  15

Ala Phe Gly Tyr Ala Phe Ser Asn Tyr Leu Ile Glu Trp Val Gln Gln
            20                  25                  30

Arg His Gly Gln Gly Leu Glu Gly Ile Gly Val Met Ile Tyr Pro Gly
        35                  40                  45

Ser Gly Asp His Lys Tyr Asn Glu Lys Phe Lys Gly Lys Ala Thr Leu
```

Thr Ala Asp Lys Ser Ser Ser Thr Ala Tyr Met Gln Leu Ser Leu
65                  70                  75                  80

Thr Ser Asp Asp Ser Ala Val Tyr Phe Cys Ala Arg Phe Asp Tyr Asp
                    85                  90                  95

Val Thr Tyr Ala Met Ala Tyr Trp Gly Gln Gly Thr Ser Ala Thr Val
                100                 105                 110

<210> SEQ ID NO 26
<211> LENGTH: 110
<212> TYPE: PRT
<213> ORGANISM: Artificial Sequence
<220> FEATURE:
<223> OTHER INFORMATION: unrelated IgG3 VH amino acid sequence
      (accession # DQ273284.1)

<400> SEQUENCE: 26

Gly Gly Gly Leu Val Gln Pro Gly Gly Ser Met Lys Leu Ser Cys Val
1               5                   10                  15

Ala Ser Glu Phe Thr Phe Asn Asn Tyr Trp Met Asn Trp Val Arg Gln
                20                  25                  30

Ser Pro Glu Lys Gly Leu Glu Trp Val Ala Glu Ile Arg Leu Lys Ser
            35                  40                  45

Asn Asn Tyr Ala Thr His Tyr Ala Glu Ser Val Lys Gly Arg Phe Thr
50                  55                  60

Ile Ser Arg Asp Asp Ser Lys Ser Ser Val Tyr Leu Gln Met Asn Asn
65                  70                  75                  80

Leu Arg Ala Glu Asp Thr Gly Ile Tyr Tyr Cys Thr Ser Asn Val Ala
                85                  90                  95

Met Asp Tyr Trp Gly Gln Gly Thr Thr Val Thr Val Ser Ser
                100                 105                 110

<210> SEQ ID NO 27
<211> LENGTH: 109
<212> TYPE: PRT
<213> ORGANISM: Artificial Sequence
<220> FEATURE:
<223> OTHER INFORMATION: unrelated IgM VH amino acid sequence
      (accession # M77137.1)

<400> SEQUENCE: 27

Gly Leu Val Ala Pro Ser Gln Ser Leu Ser Ile Thr Cys Thr Val Ser
1               5                   10                  15

Gly Phe Ser Leu Thr Ser Tyr Gly Val His Trp Val Arg Gln Pro Pro
                20                  25                  30

Gly Lys Gly Leu Glu Trp Leu Gly Val Ile Trp Ala Gly Gly Ser Thr
            35                  40                  45

Asn Tyr Asn Ser Ala Leu Met Ser Arg Leu Ser Ile Ser Lys Gly Asp
50                  55                  60

Asn Ser Lys Ser Gln Val Phe Leu Lys Met Asn Ser Leu Gln Thr Asp
65                  70                  75                  80

Asp Thr Ala Met Tyr Tyr Cys Ala Arg Cys Tyr Tyr Gly Ser His Phe
                85                  90                  95

Asp Tyr Trp Gly Gln Gly Thr Thr Leu Thr Val Ser Ser
                100                 105

<210> SEQ ID NO 28
<211> LENGTH: 104
<212> TYPE: PRT

<213> ORGANISM: Artificial Sequence
<220> FEATURE:
<223> OTHER INFORMATION: unrelated kappa VL amino acid sequence
      (accession # Z22039.1)

<400> SEQUENCE: 28

Ser Ser Leu Ala Val Ser Ala Gly Glu Lys Val Thr Met Ser Cys Lys
1               5                   10                  15

Ser Ser Gln Ser Leu Leu Asn Ser Arg Thr Arg Lys Asn Tyr Leu Ala
            20                  25                  30

Trp Tyr Gln Gln Lys Pro Gly Gln Ser Pro Lys Leu Leu Ile Tyr Trp
        35                  40                  45

Ala Ser Ser Arg Glu Ser Gly Val Pro Asp Arg Phe Thr Gly Ser Gly
    50                  55                  60

Ser Gly Thr Asp Phe Thr Leu Thr Ile Ser Ser Val Gln Ala Glu Asp
65                  70                  75                  80

Leu Ala Val Tyr Tyr Cys Lys Gln Ser Tyr Asn Leu Tyr Thr Phe Gly
                85                  90                  95

Gly Gly Thr Lys Leu Glu Ile Lys
            100

<210> SEQ ID NO 29
<211> LENGTH: 104
<212> TYPE: PRT
<213> ORGANISM: Artificial Sequence
<220> FEATURE:
<223> OTHER INFORMATION: Anti-N69 mAb kappa VL Consensus sequence

<400> SEQUENCE: 29

Leu Ser Leu Pro Val Ser Leu Gly Asp Gln Ala Ser Ile Ser Cys Lys
1               5                   10                  15

Ser Ser Gln Ser Ile Val His Ser Asn Gly Asn Thr Tyr Leu Glu Trp
            20                  25                  30

Tyr Leu Gln Arg Pro Gly Gln Ser Pro Lys Leu Leu Ile Tyr Lys Val
        35                  40                  45

Ser Asn Arg Phe Ser Gly Val Pro Asp Arg Phe Ser Gly Ser Gly Ser
    50                  55                  60

Gly Thr Asp Phe Thr Leu Lys Ile Ser Arg Val Lys Ala Glu Asp Leu
65                  70                  75                  80

Gly Val Tyr Tyr Cys Phe Gln Gly Ser His Val Pro Pro Thr Phe Gly
                85                  90                  95

Ala Gly Thr Lys Leu Glu Leu Lys
            100

<210> SEQ ID NO 30
<211> LENGTH: 104
<212> TYPE: PRT
<213> ORGANISM: Artificial Sequence
<220> FEATURE:
<223> OTHER INFORMATION: Anti-N69 mAb kappa VL Consensus sequence
<220> FEATURE:
<221> NAME/KEY: x
<222> LOCATION: (2)..(2)
<223> OTHER INFORMATION: X is S or T
<220> FEATURE:
<221> NAME/KEY: x
<222> LOCATION: (4)..(4)
<223> OTHER INFORMATION: X is P or S
<220> FEATURE:
<221> NAME/KEY: x
<222> LOCATION: (6)..(6)
<223> OTHER INFORMATION: X is S or T
<220> FEATURE:

-continued

```
<221> NAME/KEY: x
<222> LOCATION: (7)..(7)
<223> OTHER INFORMATION: X is L or I
<220> FEATURE:
<221> NAME/KEY: x
<222> LOCATION: (9)..(9)
<223> OTHER INFORMATION: X is D or Q
<220> FEATURE:
<221> NAME/KEY: x
<222> LOCATION: (10)..(10)
<223> OTHER INFORMATION: X is Q or P
<220> FEATURE:
<221> NAME/KEY: x
<222> LOCATION: (21)..(21)
<223> OTHER INFORMATION: X is L or I
<220> FEATURE:
<221> NAME/KEY: x
<222> LOCATION: (22)..(22)
<223> OTHER INFORMATION: X is V or L
<220> FEATURE:
<221> NAME/KEY: x
<222> LOCATION: (25)..(25)
<223> OTHER INFORMATION: X is N or D
<220> FEATURE:
<221> NAME/KEY: x
<222> LOCATION: (27)..(27)
<223> OTHER INFORMATION: X is N or K
<220> FEATURE:
<221> NAME/KEY: x
<222> LOCATION: (31)..(31)
<223> OTHER INFORMATION: X is E or H or N or K
<220> FEATURE:
<221> NAME/KEY: x
<222> LOCATION: (33)..(33)
<223> OTHER INFORMATION: X is Y or L
<220> FEATURE:
<221> NAME/KEY: x
<222> LOCATION: (43)..(43)
<223> OTHER INFORMATION: X is L or R
<220> FEATURE:
<221> NAME/KEY: x
<222> LOCATION: (45)..(45)
<223> OTHER INFORMATION: X is I or V
<220> FEATURE:
<221> NAME/KEY: x
<222> LOCATION: (47)..(47)
<223> OTHER INFORMATION: X is K or L
<220> FEATURE:
<221> NAME/KEY: x
<222> LOCATION: (50)..(50)
<223> OTHER INFORMATION: X is N or K
<220> FEATURE:
<221> NAME/KEY: x
<222> LOCATION: (51)..(51)
<223> OTHER INFORMATION: X is L or R
<220> FEATURE:
<221> NAME/KEY: x
<222> LOCATION: (52)..(52)
<223> OTHER INFORMATION: X is F or D
<220> FEATURE:
<221> NAME/KEY: x
<222> LOCATION: (60)..(60)
<223> OTHER INFORMATION: X is S or T
<220> FEATURE:
<221> NAME/KEY: x
<222> LOCATION: (73)..(73)
<223> OTHER INFORMATION: X is S or I
<220> FEATURE:
<221> NAME/KEY: x
<222> LOCATION: (76)..(76)
<223> OTHER INFORMATION: X is K or E
<220> FEATURE:
<221> NAME/KEY: x
<222> LOCATION: (80)..(80)
<223> OTHER INFORMATION: X is V or L
<220> FEATURE:
<221> NAME/KEY: x
<222> LOCATION: (82)..(82)
<223> OTHER INFORMATION: X is I or V
```

```
<220> FEATURE:
<221> NAME/KEY: x
<222> LOCATION: (84)..(84)
<223> OTHER INFORMATION: X is Y or F
<220> FEATURE:
<221> NAME/KEY: x
<222> LOCATION: (86)..(86)
<223> OTHER INFORMATION: X is F or S or W
<220> FEATURE:
<221> NAME/KEY: x
<222> LOCATION: (88)..(88)
<223> OTHER INFORMATION: X is G or S
<220> FEATURE:
<221> NAME/KEY: x
<222> LOCATION: (89)..(89)
<223> OTHER INFORMATION: X is S or T
<220> FEATURE:
<221> NAME/KEY: x
<222> LOCATION: (90)..(90)
<223> OTHER INFORMATION: X is H or R or Q
<220> FEATURE:
<221> NAME/KEY: x
<222> LOCATION: (91)..(91)
<223> OTHER INFORMATION: X is V or I or F
<220> FEATURE:
<221> NAME/KEY: x
<222> LOCATION: (93)..(93)
<223> OTHER INFORMATION: X is P or F or R
<220> FEATURE:
<221> NAME/KEY: x
<222> LOCATION: (97)..(97)
<223> OTHER INFORMATION: X is A or S or G
<220> FEATURE:
<221> NAME/KEY: x
<222> LOCATION: (103)..(103)
<223> OTHER INFORMATION: X is L or M or I

<400> SEQUENCE: 30

Leu Xaa Leu Xaa Val Xaa Xaa Gly Xaa Xaa Ala Ser Ile Ser Cys Lys
1               5                   10                  15

Ser Ser Gln Ser Xaa Xaa His Ser Xaa Gly Xaa Thr Tyr Leu Xaa Trp
                20                  25                  30

Xaa Leu Gln Arg Pro Gly Gln Ser Pro Lys Xaa Leu Xaa Tyr Xaa Val
            35                  40                  45

Ser Xaa Xaa Xaa Ser Gly Val Pro Asp Arg Phe Xaa Gly Ser Gly Ser
    50                  55                  60

Gly Thr Asp Phe Thr Leu Lys Ile Xaa Arg Val Xaa Ala Glu Asp Xaa
65                  70                  75                  80

Gly Xaa Tyr Xaa Cys Xaa Gln Xaa Xaa Xaa Pro Xaa Thr Phe Gly
            85                  90                  95

Xaa Gly Thr Lys Leu Glu Xaa Lys
            100
```

NUCLEIC ACIDS ENCODING ANTI-HCTNT-N69 ANTIBODIES

REFERENCE TO RELATED APPLICATIONS

This application is a divisional of U.S. patent application Ser. No. 16/009,904, filed Jun. 15, 2018, which claims priority from U.S. Provisional Patent Application Serial Nos. 62/520,250, filed Jun. 15, 2017 and 62/548,052, filed Aug. 21, 2017, the entire content of all of which is incorporated herein by reference.

FIELD OF THE INVENTION

According to general aspects, methods and compositions relating to diagnosis and treatment of cardiac disorders are provided by the present invention. According to specific aspects, methods and compositions relating to detection of HcTnT-N69 (SEQ ID NO:1) in assays relating to diagnosis and treatment of cardiac disorders are provided by the present invention.

SEQUENCE LISTING

The instant application contains a Sequence Listing which has been submitted electronically as a file in ASCII format and is hereby incorporated by reference in its entirety. Said ASCII format file, created on Jan. 12, 2022, is named 47WAY12803_ST25_txt and is 28,432 bytes in size.

BACKGROUND OF THE INVENTION

Cardiac disorders, i.e. diseases or conditions characterized by diseased or injured cardiac muscle, continue to contribute significant levels of morbidity and mortality worldwide. There is a continuing need for methods and compositions relating to diagnosis and treatment of cardiac disorders.

SUMMARY OF THE INVENTION

Antibodies and antigen binding fragments thereof characterized by specific binding to HcTnT-N69 or HcTnT-neo, or a variant of either thereof, are provided according to aspects of the present invention. According to aspects of the present invention, such antibodies and/or antigen binding fragments thereof are isolated from an animal or cell in which they are produced.

According to aspects of the present invention, an antibody or antigen binding fragment thereof is an isolated monoclonal antibody or antigen binding fragment thereof characterized by specific binding to HcTnT-N69 or HcTnT-neo or a variant of either thereof. A hybridoma producing the monoclonal antibody is provided according to aspects of the present invention. Optionally, the isolated monoclonal antibody, or antigen binding fragment thereof, characterized by specific binding to HcTnT-N69, or a variant thereof, further includes an attached detectable label. Optionally, the isolated monoclonal antibody, or antigen binding fragment thereof, characterized by specific binding to HcTnT-N69, or a variant thereof, is immobilized on a solid or semi-solid support. Optionally, the isolated monoclonal antibody, or antigen binding fragment thereof, characterized by specific binding to HcTnT-N69, or a variant thereof, is conjugated to a cargo moiety.

According to aspects of the present invention, an isolated monoclonal antibody or antigen binding fragment thereof characterized by specific binding to HcTnT-N69 or a variant thereof is provided which includes: 1) a Variable Heavy region (VH) comprising amino acid sequence SEQ ID NO: 2, or a variant thereof; and a Variable Light region (VL) comprising amino acid sequence SEQ ID NO: 30; 2) a VH region comprising amino acid sequence SEQ ID NO: 8, or a variant thereof; and a VL region comprising amino acid sequence SEQ ID NO: 30; and 3) a VH region comprising amino acid sequence SEQ ID NO: 12, or a variant thereof; and a VL region comprising amino acid sequence SEQ ID NO: 30. A hybridoma producing the monoclonal antibody is provided according to aspects of the present invention. Optionally, the isolated monoclonal antibody, or antigen binding fragment thereof, characterized by specific binding to HcTnT-N69, or a variant thereof, further includes an attached detectable label. Optionally, the isolated monoclonal antibody, or antigen binding fragment thereof, characterized by specific binding to HcTnT-N69, or a variant thereof, is immobilized on a solid or semi-solid support. Optionally, the isolated monoclonal antibody, or antigen binding fragment thereof, characterized by specific binding to HcTnT-N69, or a variant thereof, is conjugated to a cargo moiety.

According to aspects of the present invention, an isolated monoclonal antibody or antigen binding fragment thereof characterized by specific binding to HcTnT-N69 or a variant thereof is provided which includes: 1) a VH region comprising amino acid sequence SEQ ID NO: 2, or a variant thereof; and a VL region comprising amino acid sequence SEQ ID NO: 29; 2) a VH region comprising amino acid sequence SEQ ID NO: 8, or a variant thereof; and a VL region comprising amino acid sequence SEQ ID NO: 29; and 3) a VH region comprising amino acid sequence SEQ ID NO: 12, or a variant thereof; and a VL region comprising amino acid sequence SEQ ID NO: 29. A hybridoma producing the monoclonal antibody is provided according to aspects of the present invention. Optionally, the isolated monoclonal antibody, or antigen binding fragment thereof, characterized by specific binding to HcTnT-N69, or a variant thereof, further includes an attached detectable label. Optionally, the isolated monoclonal antibody, or antigen binding fragment thereof, characterized by specific binding to HcTnT-N69, or a variant thereof, is immobilized on a solid or semi-solid support. Optionally, the isolated monoclonal antibody, or antigen binding fragment thereof, characterized by specific binding to HcTnT-N69, or a variant thereof, is conjugated to a cargo moiety.

According to aspects of the present invention, an isolated monoclonal antibody or antigen binding fragment thereof characterized by specific binding to HcTnT-N69 or a variant thereof is provided which includes: 1) a VH region comprising amino acid sequence SEQ ID NO: 2, or a variant thereof; and a VL region comprising amino acid sequence SEQ ID NO: 3 or SEQ ID NO: 6 or a variant of either thereof 2) a VH region comprising amino acid sequence SEQ ID NO: 8, or a variant thereof; and a VL region comprising amino acid sequence SEQ ID NO: 9 or a variant thereof; and 3) a VH region comprising amino acid sequence SEQ ID NO: 12, or a variant thereof; and a VL region comprising amino acid sequence SEQ ID NO:13, SEQ ID NO: 16, SEQ ID NO: 18, SEQ ID NO: 20, or a variant of any thereof. A hybridoma producing the monoclonal antibody is provided according to aspects of the present invention. Optionally, the isolated monoclonal antibody, or antigen binding fragment thereof, characterized by specific binding to HcTnT-N69, or a variant thereof, further includes an attached detectable label. Optionally, the isolated monoclonal antibody, or antigen binding fragment thereof, characterized by specific binding to HcTnT-N69, or a variant thereof, is immobilized on a solid or semi-solid support. Optionally, the isolated monoclonal antibody, or antigen binding fragment thereof, characterized by specific binding to HcTnT-N69, or a variant thereof, is conjugated to a cargo moiety.

Nucleic acids are provided according to aspects of the present invention encoding a VH or VL region of an isolated antibody or antigen binding fragment thereof wherein the antibody is characterized by specific binding to HcTnT-N69 or HcTnT-neo or a variant of either thereof.

Expression constructs are provided according to aspects of the present invention which include a nucleic acid encoding a VH or VL region of an isolated antibody or antigen binding fragment thereof wherein the antibody is characterized by specific binding to HcTnT-N69 or HcTnT-neo or a variant of either thereof.

Hybridomas are provided according to aspects of the present invention containing a nucleic acid encoding a VH or VL region of an isolated antibody or antigen binding fragment thereof wherein the antibody is characterized by specific binding to HcTnT-N69 or a variant thereof, and wherein the hybridomas produce monoclonal antibodies including the encoded VH or VL region and characterized by specific binding to HcTnT-N69 or HcTnT-neo or a variant of either thereof.

Methods for detecting a cardiac condition in a human subject are provided according to aspects of the present invention which include providing an immunological reagent characterized by specific binding to: an N-terminal fragment of human cardiac troponin T (HcTnT-N69) or a neoepitope of human cardiac troponin T generated by removal of HcTnT-N69 from HcTnT (HcTnT-neo); contacting the immunological reagent with a biological sample of the human subject under binding conditions; and detecting binding of the immunological reagent with HcTnT-N69 or HcTnT-neo, wherein detection of HcTnT-N69 or HcTnT-neo in the biological sample is indicative of a cardiac condition in the subject.

Methods for detecting a cardiac condition in a human subject are provided according to aspects of the present invention which include providing a monoclonal antibody which specifically binds to HcTnT-N69 (SEQ ID NO:1); contacting the monoclonal antibody with a biological sample of the human subject under binding conditions; and detecting binding of the monoclonal antibody with HcTnT-N69, wherein detection of HcTnT-N69 in the biological sample is indicative of a cardiac condition in the subject.

Methods for detecting a cardiac condition in a human subject are provided according to aspects of the present invention which include providing a monoclonal antibody which specifically binds to HcTnT-N69 (SEQ ID NO:1), wherein monoclonal antibody which specifically binds to HcTnT-N69 (SEQ ID NO:1) is selected from the group consisting of: 1) a monoclonal antibody comprising: a Variable Heavy region (VH) comprising amino acid sequence SEQ ID NO: 2, or a variant thereof; and a Variable Light region (VL) comprising amino acid sequence SEQ ID NO: 30; 2) a monoclonal antibody comprising: a VH region comprising amino acid sequence SEQ ID NO: 8, or a variant thereof; and a VL region comprising amino acid sequence SEQ ID NO: 30; and 3) a monoclonal antibody comprising: a VH region comprising amino acid sequence SEQ ID NO: 12, or a variant thereof; and a VL region comprising amino acid sequence SEQ ID NO: 30; contacting the monoclonal antibody with a biological sample of the human subject under binding conditions; and detecting binding of the monoclonal antibody with HcTnT-N69, wherein detection of HcTnT-N69 in the biological sample is indicative of a cardiac condition in the subject.

Methods for detecting a cardiac condition in a human subject are provided according to aspects of the present invention which include providing a monoclonal antibody which specifically binds to HcTnT-N69 (SEQ ID NO:1), wherein monoclonal antibody which specifically binds to HcTnT-N69 (SEQ ID NO:1) is selected from the group consisting of: 1) a monoclonal antibody comprising: a VH region comprising amino acid sequence SEQ ID NO: 2, or a variant thereof; and a VL region comprising amino acid sequence SEQ ID NO: 29; 2) a monoclonal antibody comprising: a VH region comprising amino acid sequence SEQ ID NO: 8, or a variant thereof; and a VL region comprising amino acid sequence SEQ ID NO: 29; and 3) a monoclonal antibody comprising: a VH region comprising amino acid sequence SEQ ID NO: 12, or a variant thereof; and a VL region comprising amino acid sequence SEQ ID NO: 29; contacting the monoclonal antibody with a biological sample of the human subject under binding conditions; and detecting binding of the monoclonal antibody with HcTnT-N69, wherein detection of HcTnT-N69 in the biological sample is indicative of a cardiac condition in the subject.

Methods for detecting a cardiac condition in a human subject are provided according to aspects of the present invention which include providing a monoclonal antibody which specifically binds to HcTnT-N69 (SEQ ID NO:1), wherein monoclonal antibody which specifically binds to HcTnT-N69 (SEQ ID NO:1) is selected from the group consisting of: 1) a monoclonal antibody comprising: a VH region comprising amino acid sequence SEQ ID NO: 2, or a variant thereof; and a VL region comprising amino acid sequence SEQ ID NO: 3 or SEQ ID NO: 6 or a variant of either thereof; 2) a monoclonal antibody comprising: a VH region comprising amino acid sequence SEQ ID NO: 8, or a variant thereof; and a VL region comprising amino acid sequence SEQ ID NO: 9 or a variant thereof; and 3) a monoclonal antibody comprising: a VH region comprising amino acid sequence SEQ ID NO: 12, or a variant thereof; and a VL region comprising amino acid sequence SEQ ID NO:13, SEQ ID NO: 16, SEQ ID NO: 18, SEQ ID NO: 20, or a variant of any thereof; contacting the monoclonal antibody with a biological sample of the human subject under binding conditions; and detecting binding of the monoclonal antibody with HcTnT-N69, wherein detection of HcTnT-N69 in the biological sample is indicative of a cardiac condition in the subject.

Optionally, the biological sample is cardiac muscle, whole blood, plasma, serum, urine, saliva or another body fluid.

Optionally, the assaying includes an ELISA assay.

Optionally, the assaying includes immunochromatography; antigen capture; flow cytometry; immunoblot; immunoprecipitation; immunodiffusion; competitive immunoassay, immunocytochemistry; radioimmunoassay; or a combination of any two or more thereof.

According to aspects of inventive methods, a human patient urine sample and a human patient serum sample are both assayed and a ratio of results of the assay is calculated.

According to aspects of inventive methods, obtaining a biological sample of the human subject is obtained and, the contacting step is performed outside of the body of the human subject. According to aspects of inventive methods, the biological sample of the human subject is present in the body of the human subject and the contacting step is performed inside of the body of the human subject.

Immunoassay kits for detecting a cardiac condition of a human subject having or suspected of having a cardiac condition, are provided according to aspects of the present invention including one or more antibodies or antigen binding fragments wherein the one or more antibodies or antigen binding fragments are characterized by specific binding to HcTnT-N69, or a variant thereof.

BRIEF DESCRIPTION OF THE DRAWINGS

FIG. 10 shows alignment comparisons of variable region amino acid sequences of anti-HcTnT N69 monoclonal antibodies. VH variants 1, 2, and 3. As shown VH Variant 1 (IgG1) is included in mAbs 1D6, 2A8, 2C1, 2D11, 2F11, 3F3; VH Variant 2 (IgG3) is included in mAbs 1E11, 3B6, 3E5; and VH Variant 3 (IgM) is included in mAbs 3H5, 2H3, 4F5, 2D9. Comparison of VH Variant 1 with an unrelated IgG1 VH amino acid sequence (accession # S59138.1, SEQ ID NO:25) shows that 38.9% (44/113 aligned residues) of the residues are non-conserved, thus specific to the anti-N69 mAbs; Conserved residues are underlined in the unrelated reference sequence. Comparison of VH Variant 2 with an unrelated IgG3 VH amino acid sequence (accession # DQ273284.1, SEQ ID NO:26) shows that 54.5% (60/110 aligned residues) of the residues are non-conserved, thus specific to the anti-N69 mAbs; Conserved residues are underlined in the unrelated reference sequence. Comparison of VH Variant 3 with an unrelated IgM VH amino acid sequence (accession # M77137.1, SEQ ID NO:27) shows that 50.9% (57/112 aligned residues) of the residues are non-conserved, thus specific to the anti-N69 mAbs; Conserved residues are underlined in the unrelated reference sequence.

FIG. 11 shows alignment comparisons of variable region amino acid sequences of anti-HcTnT N69 monoclonal antibodies. As shown, VL (kappa) variant 1 is included in mAbs 1D6, 2A8, 2C1; VL (kappa) variant 2 is included in mAbs 2D11, 2F11, 3F3VL; (kappa) variant 3 is included in mAbs 1E11, 3B6, 3E5; VL (kappa) variant 4 is included in mAb 3H5; VL (kappa) variant 5 is included in mAb 2H3; VL (kappa) variant 6 is included in mAb 4F5; and VL (kappa) variant 7 is included in mAb 2D9. Comparison of VL Variants 1 to 7 with an unrelated kappa VL amino acid sequence (accession # Z22039.1, SEQ ID NO:28) shows that for Variant 1: 34.3% (36/105) of the residues are non-conserved; Variant 2: 34.3% (36/105) of the residues are non-conserved; Variant 3: 39.0% (41/105) of the residues are non-conserved; Variant 4: 33.3% (35/105) of the residues are non-conserved; Variant 5: 33.3% (35/105) of the residues are non-conserved; Variant 6: 33.3% (35/105) of the residues are non-conserved; Variant 7: 33.3% (35/105) of the residues are non-conserved. Conserved residues are underlined in the unrelated reference sequence. The shaded residues are diverged and different among the anti-N69 mAbs. FIG. 11 illustrates that the consensus sequence of anti-N69 mAb kappa VL (SEQ ID NO:29) shows 42.9% specificity versus the reference sequence (45/105 aligned residues).

DETAILED DESCRIPTION OF THE INVENTION

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; Engelke, D. R., RNA Interference (RNAi): Nuts and Bolts of RNAi Technology, DNA Press LLC, Eagleville, P A, 2003; Herdewijn, P. (Ed.), Oligonucleotide Synthesis: Methods and Applications, Methods in Molecular Biology, Humana Press, 2004; A. Nagy, M. Gertsenstein, K. Vintersten, R. Behringer, Manipulating the Mouse Embryo: A Laboratory Manual, 3rd edition, Cold Spring Harbor Laboratory Press; Dec. 15, 2002, ISBN-10: 0879695919; Kursad Turksen (Ed.), Embryonic stem cells: methods and protocols in Methods Mol Biol. 2002; 185, Humana Press; Current Protocols in Stem Cell Biology, ISBN: 9780470151808.

The singular terms "a," "an," and "the" are not intended to be limiting and include plural referents unless explicitly stated otherwise or the context clearly indicates otherwise.

Figure 1:
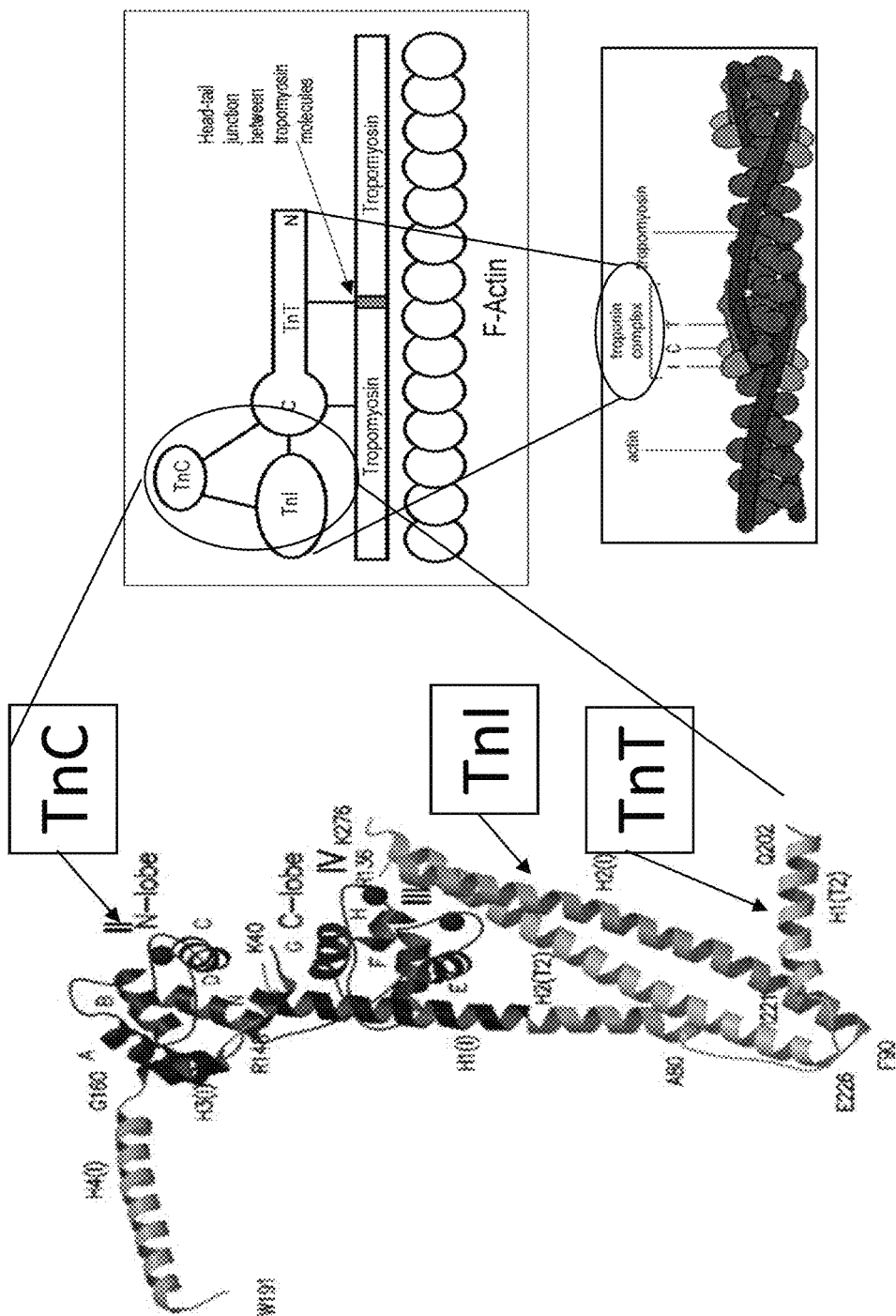
FIG. 1 shows a 3-D diagram and adjacent schematics illustrating regions of cardiac troponin T (cTnT) and interactions with other muscle proteins, troponin I, troponin C, tropomyosin and F-Actin. The N-terminal region of cTnT is not resolved in the crystal structure, implicating a flexible structure.
Figure 2:
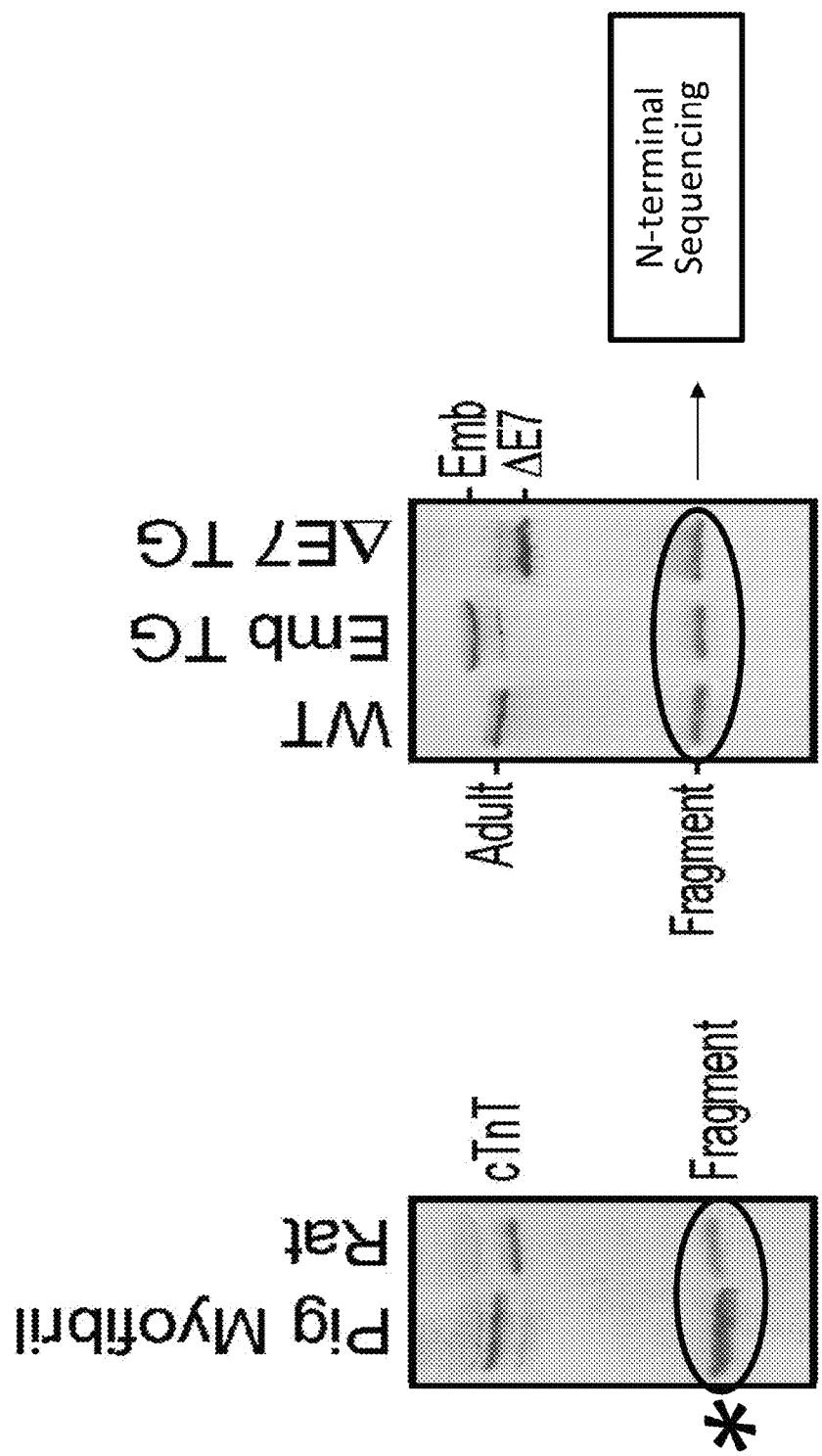
FIG. 2 illustrates rapid, massive and restrictive N-terminal (NT) truncation of cTnT in ischemia. At the asterisk (*), the results show that over 50% of cTnT was restrictively cleaved to selectively remove the N-terminal segment in the remote zone of MI pig left ventricle in 40 min.

The N-terminal Region of cardiac troponin (cTnT) is a regulatory structure that is altered by posttranscriptional modification. FIG. 1 shows a 3-D diagram and adjacent schematics illustrating regions of cTnT and interactions with other muscle proteins, troponin I, troponin C, tropomyosin and F-Actin. The N-terminal region of cTnT is not resolved in the crystal structure, implicating a flexible structure.

cTnT is truncated by restrictive proteolysis in cardiomyocytes, generating an N-terminal fragment and a truncated cTnT protein in a subject having a cardiac condition, exemplified by acute ischemia and/or acute pressure overload. FIG. 2 illustrates rapid, massive and restrictive N-terminal (NT) truncation of cTnT in ischemia.

Figure 3:
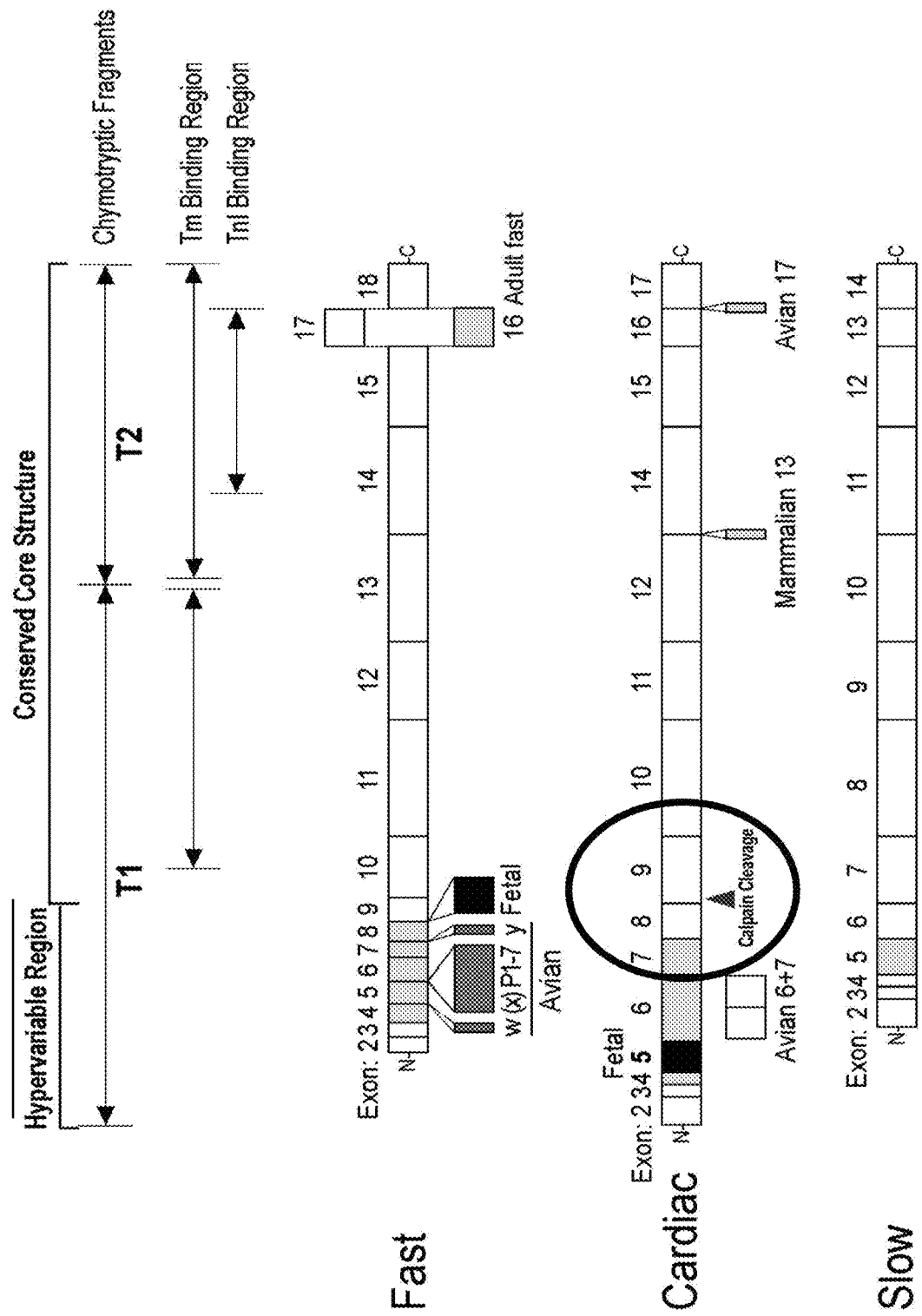
FIG. 3 is a diagram illustrating aspects of cardiac troponin T compared to fast skeletal muscle troponin T or slow skeletal muscle troponin T, as described in detail in Jin, Zhang, & Bautista, Crit Rev Eukar Gene Expr 2008 and Wei & Jin, Gene 2016. The NT truncation site is shown, see the circled "calpain cleavage" site.
Figure 4:
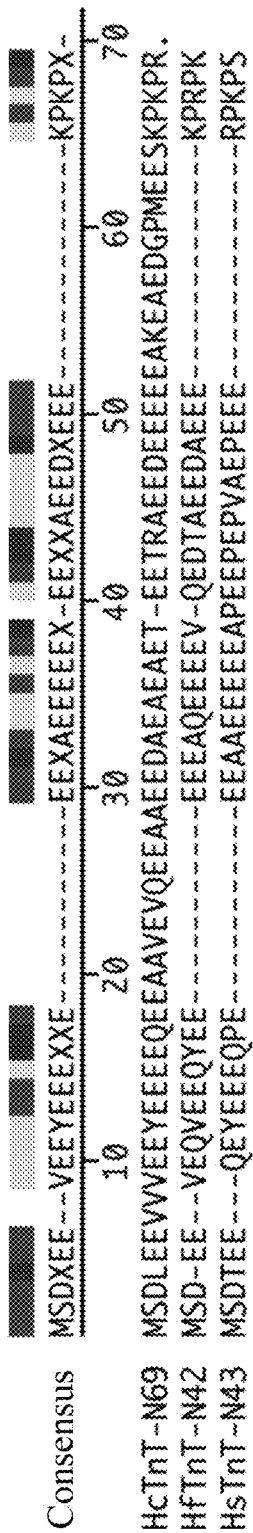
FIG. 4 shows alignment of N-terminal regions of human cardiac troponin T (HcTnT-N69, SEQ ID NO:1), human fast skeletal muscle troponin T (HfTnT-N42, SEQ ID NO:22) and human slow skeletal muscle troponin T (HsTnT-N43, SEQ ID NO:23), along with a consensus sequence, SEQ ID NO:24, obtained by comparison of HcTnT-N69, HfTnT-N42, and HsTnT-N43.

FIG. 3 is a diagram illustrating aspects of cardiac troponin T compared to fast skeletal muscle troponin T or slow skeletal muscle troponin T, as described in detail in Jin, Zhang, & Bautista, Crit Rev Eukar Gene Expr 2008 and Wei & Jin, Gene 2016. FIG. 4 shows alignment of N-terminal regions of human cardiac troponin T (HcTnT-N69, SEQ ID NO:1), human fast skeletal muscle troponin T (HfTnT-N42, SEQ ID NO:22) and human slow skeletal muscle troponin T (HsTnT-N43, SEQ ID NO:23), along with a consensus sequence, SEQ ID NO:24 obtained by comparison of HcTnT-N69, HfTnT-N42, and HsTnT-N43.

Figure 5:
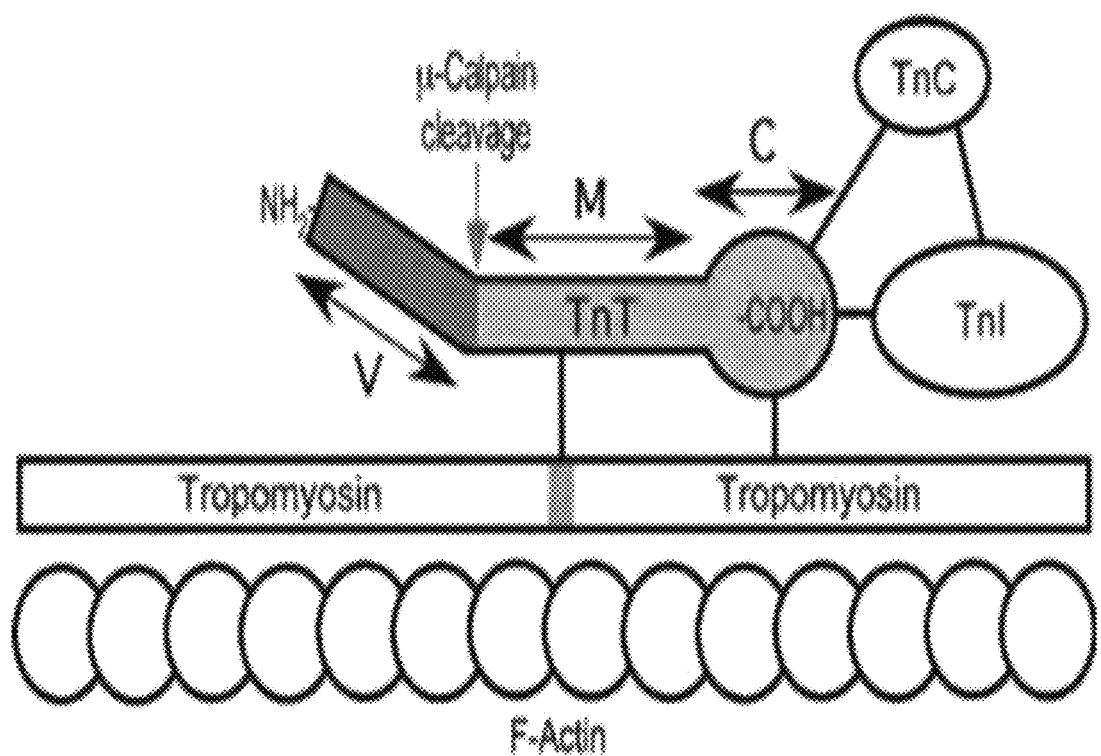
FIG. 5 is a diagram showing the N-terminal variable region of cTnT.

FIG. 5 is a diagram showing the N-terminal variable region of cTnT.

The N-terminal cTnT fragment cleaved from cTnT is 68-72 amino acids in length with a molecular weight of approximately 8 kD.

The N-terminal cTnT fragment cleaved from cTnT, N69 peptide, is rapidly cleaved in cardiac muscle cells in disease conditions such as myocardial ischemic and other kind of damages. This is an early response of the heart to stress conditions, and occurs prior to or without the death of cardiac muscle cells. Cleavage of the N-terminal cTnT fragment from cTnT is an adaptive response to stresses which serves to decrease myocardial energy expenditure while maintaining baseline cardiac function. Therefore, the detection of the N69 peptide, and/or variants thereof, provides an early blood marker for cardiac stress, especially valuable for the diagnosis of myocardial ischemia prior to cell death, and identify non-ischemic myocardial infarction.

Assays

Methods for aiding in the detection and diagnosis of a cardiac disorder in a human subject having or suspected of having a cardiac disorder are provided which include assaying a biological sample for an N-terminal fragment of human cardiac troponin T (NT-cTnT) generated by removal of the N-terminal fragment from and/or a neoepitope (HcTnT-neo) at the new N-terminal region of human cardiac troponin T generated by removal of the N-terminal fragment NT-cTnT, to detect either or both NT-cTnT and HcTnT-neo in the biological sample.

Particular N-terminal fragments of human cardiac troponin T disclosed herein as an analyte in human samples and associated with a cardiac condition in a human patient include HcTnT-N69 (SEQ ID NO:1) and variants thereof.

Methods for aiding in the detection and diagnosis of a cardiac disorder in a human subject having or suspected of having a cardiac disorder are provided which include collecting a biological sample from the human subject; and assaying the sample using an antibody specific for HcTnT-N69 (SEQ ID NO:1) and variants thereof to detect the cleaved N-terminal fragment in the biological sample.

Methods for aiding in the detection and diagnosis of a cardiac disorder in a human subject having or suspected of having a cardiac disorder are provided which include collecting a biological sample from the human subject; and assaying the sample using an antibody specific for HcTnT-neo in the biological sample.

Methods for aiding in the detection and diagnosis of a cardiac disorder in a human subject having or suspected of having a cardiac disorder are provided which include collecting a biological sample from the human subject; and assaying the sample using an antibody specific for a 69 amino acid N-terminal fragment of human cardiac troponin T (HcTnT-N69, SEQ ID NO:1), or one or more cleavage variants thereof, to detect HcTnT-N69 in the biological sample.

Methods for aiding in the detection and diagnosis of a cardiac disorder in a human subject having or suspected of having a cardiac disorder are provided which include collecting a biological sample from the human subject; and assaying the sample using an antibody specific for a neoepitope of human cardiac troponin T (HcTnT-neo) generated by removal of the N-terminal fragment of human cardiac troponin T (HcTnT-N69, SEQ ID NO:1), or a cleavage variant thereof, to detect HcTnT-neo in the biological sample.

The phrase "cardiac disorder" refers to a disease or condition characterized by diseased or injured cardiac muscle, including, but not limited to, ischemic events including acute or chronic myocardial ischemia, acute heart failure, chronic heart failure, acute or chronic coronary syndrome, coronary artery disease, pressure overload including left ventricular pressure overload, right ventricular pressure overload, left atrial pressure overload, right atrial pressure overload, aortic stenosis, atherosclerosis, inflammatory conditions such as myocarditis, pericarditis and endocarditis, cardiomyopathy, angina, blood vessel graft disease, occlusive coronary thrombus, valvular heart disease, arrhythmia including tachycardia, congenital heart diseases, and inflammatory cardiomegaly.

Methods for detecting a cardiac disorder in a human subject having or suspected of having a cardiac disorder which include obtaining a biological sample from the human subject; providing one or more antibodies or antigen binding fragments characterized by specific binding to an epitope of the HcTnT-N69 peptide or variant thereof; and assaying the biological sample using the one or more antibodies or antigen binding fragments, wherein detection of HcTnT-N69 peptide or variant thereof in the biological sample is indicative of a cardiac disorder in the human subject.

Methods for detecting a cardiac disorder in a human subject having or suspected of having a cardiac disorder which include obtaining a biological sample from the human subject; providing one or more antibodies or antigen binding fragments characterized by specific binding to HcTnT-neo or variant thereof; in the biological sample using the one or more antibodies or antigen binding fragments, wherein detection of HcTnT-neo or variant thereof in the biological sample is indicative of a cardiac disorder in the human subject.

Detection of HcTnT-N69 and/or HcTnT-neo in the biological sample of a human subject is indicative of a cardiac disorder in the subject.

A biological sample which is assayed for HcTnT-N69 and/or HcTnT-neo according to processes of the invention may be any biological sample containing or suspected of containing HcTnT-N69 and/or HcTnT-neo including, whole blood, plasma, serum, urine, saliva and other body fluids. According to aspects of the present invention, a biological sample which is assayed for HcTnT-N69 and/or HcTnT-neo according to processes of the invention is human urine, whole blood, plasma, serum, saliva, or a combination of any two or more thereof.

Assays according to aspects, assays for HcTnT-N69 and/or HcTnT-neo allow a user to differentiate between type 1 and type 2 myocardial infarction; differentiate acute myocardial infarction from remodeling; and/or determine therapeutic effectiveness, such as in acute heart failure and acute coronary syndrome.

Assays according to aspects, are conveniently performed in various settings, including home, office, clinic, hospital as well as in the field, such as by paramedics or other emergency response personnel.

According to particular aspects, a serum sample is obtained from the subject and assayed for HcTnT-N69 and/or HcTnT-neo for early detection of acute myocardial ischemia in chest pain patients.

According to particular aspects, a serum sample is obtained from the subject and assayed for HcTnT-N69 and/or HcTnT-neo for indicator of true myocardial ischemia in patients with non-ST-elevation myocardial infarction (NSTEMI) or type II myocardial infarction.

Optionally, a ratio of serum HcTnT-N69 and/or serum HcTnT-neo to total serum high sensitivity cardiac troponin T (hs-cTnT) and/or high sensitivity cardiac troponin I (hs-cTnI) is obtained as an indicator of true myocardial ischemia in patients with non-ST-elevation myocardial infarction (NSTEMI) or type II myocardial infarction.

In a further option, fractional troponin truncation is assayed as an indicator of true myocardial ischemia in patients with non-ST-elevation myocardial infarction (NSTEMI) or type II myocardial infarction.

According to particular aspects, a urine sample is obtained from the subject and assayed for HcTnT-N69 and/or HcTnT-neo for early detection of acute myocardial ischemia in chest pain patients.

According to particular aspects, a urine sample is obtained from the subject and assayed for HcTnT-N69 and/or HcTnT-neo for monitoring of chronic heart failure treatment.

According to particular aspects, a urine sample is obtained from the subject and assayed for HcTnT-N69 and/or HcTnT-neo to monitor therapeutic effectiveness in acute heart failure patients. For example, clearance of HcTnT-N69 and/or HcTnT-neo over time, such as measured in serial samples obtained at various intervals or as a 24-hour measurement, is indicative of therapeutic effectiveness in acute heart failure patients.

According to particular aspects, two or more samples are assayed for HcTnT-N69 and/or HcTnT-neo to obtain a ratio of the analyte (HcTnT-N69 and/or HcTnT-neo) in the first sample:second sample.

According to particular aspects, two or more samples are assayed for HcTnT-N69 and/or HcTnT-neo to obtain a ratio of the analyte (HcTnT-N69 and/or HcTnT-neo) in the first sample:second sample, where the first sample is obtained from the subject earlier than the second sample.

According to particular aspects, a urine sample is obtained from the subject and a serum sample is obtained from the subject and both samples assayed for HcTnT-N69 to obtain a ratio of HcTnT-N69 in the urine sample:serum sample. This ratio is relevant to timing of acute myocardial ischemia onset and duration of on-going myocardial ischemia.

According to particular aspects, a urine sample is obtained from the subject and a serum sample is obtained from the subject and both samples assayed for HcTnT-neo to obtain a ratio of HcTnT-neo in the urine sample:serum sample. This ratio is relevant to timing of acute myocardial ischemia onset and duration of on-going myocardial ischemia.

The terms "subject" and "patient" are used interchangeably herein and refer to a human individual.

Optionally, a control or standard is included in a method for aiding in the detection and diagnosis of a cardiac disorder in a human subject suspected of having a cardiac disorder according to aspects of the present invention.

The terms "control" and "standard" are familiar to those of ordinary skill in the art and refer to any control or standard that can be used for comparison. The control or standard may be determined prior to assay for HcTnT-N69 and/or HcTnT-neo, in parallel, simultaneously, in a multiplex assay or other assay format. A control or standard can be a first HcTnT-N69 and/or HcTnT-neo level determined by assay in a first sample obtained from a patient. A control or standard can be a negative control and/or a positive control.

Detection of HcTnT-N69 and/or HcTnT-neo in a biological sample according to aspects of the present invention is accomplished by immunoassay using an antibody or antigen binding fragment thereof characterized by specific binding to an epitope of SEQ ID NO:1 or variant thereof.

The term "epitope" refers to a portion of an antigen that is bound by an antibody.

Methods and compositions of the present invention are not limited to particular amino acid sequences identified herein and variants of a reference peptide or protein are encompassed.

Variants of a peptide or protein described herein are characterized by conserved functional properties compared to the corresponding peptide or protein.

The term "HcTnT-N69" refers to the peptide of SEQ ID NO:1 and optionally encompasses variant peptides having at least 95%, 96%, 97%, 98%, 99%, or greater identity to full-length SEQ ID NO:1 as well as variant peptides having at least 95%, 96%, 97%, 98%, 99%, or greater identity, such as 100% identity, to full-length SEQ ID NO:1 with an additional 1, 2, 3 or 4 amino acids on the N-terminal or C-terminal end of the sequence compared to full-length SEQ ID NO:1. The term "HcTnT-N69" further includes variants of NT-cTnT resulting from variable proteolysis and alternative RNA splicing, Percent identity is determined by comparison of amino acid or nucleic acid sequences, including a reference amino acid or nucleic acid sequence and a putative homologue amino acid or nucleic acid sequence. To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions×100%). The two sequences compared are generally the same length or nearly the same length. Optionally, the two sequences are natural variants of a structural domain of a protein or two related proteins.

The determination of percent identity between two sequences can also be accomplished using a mathematical algorithm. Algorithms used for determination of percent identity illustratively include the algorithms of S. Karlin and S. Altshul, PNAS, 90:5873-5877, 1993; T. Smith and M. Waterman, Adv. Appl. Math. 2:482-489, 1981, S. Needleman and C. Wunsch, J. Mol. Biol., 48:443-453, 1970, W. Pearson and D. Lipman, PNAS, 85:2444-2448, 1988 and others incorporated into computerized implementations such as, but not limited to, GAP, BESTFIT, FASTA, TFASTA; and BLAST, for example incorporated in the Wisconsin Genetics Software Package, Genetics Computer Group, 575 Science Drive, Madison, Wis.) and publicly available from the National Center for Biotechnology Information.

A non-limiting example of a mathematical algorithm utilized for the comparison of two sequences is the algorithm of Karlin and Altschul, 1990, PNAS 87:2264-2268, modified as in Karlin and Altschul, 1993, PNAS. 90:5873-5877. Such an algorithm is incorporated into the NBLAST and XBLAST programs of Altschul et al., 1990, J. Mol. Biol. 215:403. BLAST nucleotide searches are performed with the NBLAST nucleotide program parameters set, e.g., for score=100, word length=12 to obtain nucleotide sequences homologous to a nucleic acid molecules of the present invention. BLAST protein searches are performed with the XBLAST program parameters set, e.g., to score 50, word length=3 to obtain amino acid sequences homologous to a protein molecule of the present invention. To obtain gapped alignments for comparison purposes, Gapped BLAST are utilized as described in Altschul et al., 1997, Nucleic Acids Res. 25:3389-3402. Alternatively, PSI BLAST is used to perform an iterated search which detects distant relationships between molecules. When utilizing BLAST, Gapped BLAST, and PSI Blast programs, the default parameters of the respective programs (e.g., of XBLAST and NBLAST) are used. Another preferred, non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 is used.

The percent identity between two sequences is determined using techniques similar to those described above, with or without allowing gaps. In calculating percent identity, typically only exact matches are counted.

One of skill in the art will recognize that one or more amino acid mutations can be introduced without altering the functional properties of a given nucleic acid or protein, respectively. Mutations can be introduced using standard molecular biology techniques, such as site-directed mutagenesis and PCR-mediated mutagenesis, to produce variants. For example, one or more amino acid substitutions, additions, or deletions can be made without altering the functional properties of a reference protein.

When comparing a reference protein to a putative variant, amino acid similarity may be considered in addition to identity of amino acids at corresponding positions in an amino acid sequence. "Amino acid similarity" refers to amino acid identity and conservative amino acid substitutions in a putative variant compared to the corresponding amino acid positions in a reference protein.

Conservative amino acid substitutions can be made or may be present in reference proteins to produce or identify variants.

Conservative amino acid substitutions are art recognized substitutions of one amino acid for another amino acid having similar characteristics. For example, each amino acid may be described as having one or more of the following characteristics: electropositive, electronegative, aliphatic, aromatic, polar/nonpolar, hydrophobic and hydrophilic. A conservative substitution is a substitution of one amino acid having a specified structural or functional characteristic for another amino acid having the same characteristic. Acidic amino acids include aspartate, glutamate; basic amino acids include histidine, lysine, arginine; aliphatic amino acids include isoleucine, leucine and valine; aromatic amino acids include phenylalanine, tyrosine and tryptophan; polar amino acids include aspartate, glutamate, histidine, lysine, asparagine, glutamine, arginine, serine, threonine and tyrosine; and hydrophobic amino acids include alanine, cysteine, phenylalanine, glycine, isoleucine, leucine, methionine, proline, valine and tryptophan; and conservative substitutions include substitution among amino acids within each group. Amino acids may also be described in terms of relative size; alanine, cysteine, aspartate, glycine, asparagine, proline, threonine, serine, valine are all typically considered to be small.

A variant can include synthetic amino acid analogs, amino acid derivatives and/or non-standard amino acids, illustratively including, without limitation, alpha-aminobutyric acid, citrulline, canavanine, cyanoalanine, diaminobutyric acid, diaminopimelic acid, dihydroxy-phenylalanine, djenkolic acid, homoarginine, hydroxyproline, norleucine, norvaline, 3-phosphoserine, homoserine, 5-hydroxytryptophan, 1-methylhistidine, 3-methylhistidine, and ornithine.

The phrase "specific binding" and grammatical equivalents as used herein in reference to binding of an anti-HcTnT-N69 antibody or antigen binding fragment (also referred to as an anti-N69 antibody or anti-N69 monoclonal antibody) or anti-HcTnT-neo antibody or antigen binding fragment to HcTnT-N69 or HcTnT-neo, respectively, refers to binding of the antibody or antigen binding fragment to HcTnT-N69 (free (cleaved) HcTnT-N69 peptide or present in intact HcTnT) or HcTnT-neo without substantial binding to peptides or proteins other than intact HcTNT present in a biological sample to be assayed for presence of HcTnT-N69 and/or HcTnT-neo. It is understood by the ordinarily skilled artisan that specific binding refers to specific binding as determinable by use of appropriate controls to distinguish it from nonspecific binding.

According to aspects of the present invention, the phrase "specific binding" and grammatical equivalents as used herein in reference to binding of an anti-HcTnT-N69 antibody or antigen binding fragment or anti-HcTnT-neo antibody or antigen binding fragment to HcTnT-N69 or HcTnT-neo, respectively, without substantial binding to other human non-cardiac muscle proteins or peptides, other than intact HcTNT, such as fast skeletal muscle troponin or slow skeletal muscle troponin, wherein the antibody or antigen binding fragment has an affinity constant (KA) greater than $1 \times 10^5$ M for HcTnT-N69 or HcTnT-neo, or a variant of either thereof. The term "without substantial binding to other human non-cardiac muscle proteins or peptides" refers to a minimal amount of binding to other human non-cardiac muscle proteins or peptides such that HcTnT-N69, intact HcTnT, or HcTnT-neo is the predominant peptide or protein detected in an immunodetection assay where HcTnT-N69, intact HcTnT, HcTnT-neo and other human non-cardiac muscle proteins or peptides are present together in a sample. For example, "without substantial binding to other human non-cardiac muscle proteins or peptides" refers to less than 25%, 20%, 15%, 10%, 5%, 1% or 0.1%, binding to other human non-cardiac muscle proteins or peptides such that HcTnT-N69, intact HcTnT, or HcTnT-neo is the predominant peptide or protein detected in an immunodetection assay where HcTnT-N69, intact HcTnT, HcTnT-neo and other human non-cardiac muscle proteins or peptides are present together in a sample.

As used herein, the terms "antibody" and "antibodies" relate to monoclonal antibodies, polyclonal antibodies, bispecific antibodies, multispecific antibodies, chimeric antibodies, camelized antibodies, single domain antibodies, single-chain Fvs (scFv), single chain antibodies, disulfide-linked Fvs (sdFv), and antigen-binding fragments of any of these. In particular, antibodies include immunoglobulin molecules and immunologically active fragments of immunoglobulin molecules, i.e., molecules that contain an antigen binding site. Immunoglobulin molecules are of any type (e.g., IgG, IgE, IgM, IgD, IgA and IgY), class or subclass (e.g., IgG1, IgG2 including IgG2a and IgG2b, IgG3, IgG4, IgA1 and IgA2).

As used herein, the term "antigen-binding fragment" defines a fragment of an antibody that immunospecifically binds to a target antigen. An antigen-binding fragment may be generated by any technique known to one of skill in the art. For example, Fab and F(ab')2 antigen-binding fragments may be produced by proteolytic cleavage of immunoglobulin molecules, using enzymes such as papain (to produce Fab antigen-binding fragments) or pepsin (to produce F(ab')2 antigen-binding fragments). Antigen-binding fragments are also produced by recombinant DNA technologies. Antigen-binding fragments encompassed by the present compositions and methods possess the ability to specifically bind HcTnT-N69 (free (cleaved) HcTnT-N69 peptide or present in intact HcTnT) or HcTnT-neo.

Antibodies, antigen-binding fragments and methods for their generation are known in the art, for instance, as described in Antibody Engineering, Kontermann, R. and Dübel, S. (Eds.), Springer, 2001; Harlow, E. and Lane, D., Antibodies: A Laboratory Manual, Cold Spring Harbor Laboratory Press, 1988; Ausubel, F. et al., (Eds.), Short Protocols in Molecular Biology, Wiley, 2002; J. D. Pound (Ed.) Immunochemical Protocols, Methods in Molecular Biology, Humana Press, 2nd ed., 1998; B. K. C. Lo (Ed.), Antibody Engineering: Methods and Protocols, Methods in Molecular Biology, Humana Press, 2003; and Kohler, G. and Milstein, C., Nature, 256:495-497 (1975).

Monoclonal antibodies may be produced using any technique known in the art. For example, a hybridoma cell line is produced by immunizing an animal with HcTnT-N69; harvesting spleen cells from the immunized animal; fusing the harvested spleen cells to a myeloma cell line, thereby generating hybridoma cells; establishing hybridoma cell lines from the hybridoma cells, and identifying a hybridoma cell line that produces an antibody that binds HcTnT-N69 (e.g., as described in Examples herein). Such hybridoma cell lines, and anti-HcTnT-N69 monoclonal antibodies produced by them, are aspects of the present application. Monoclonal antibodies secreted by a hybridoma cell line can be purified using any technique known in the art.

The term "isolated," as used herein, refers to material that is removed from its original or native environment. For example, a naturally-occurring polynucleotide or polypeptide present in a living animal is not isolated, but the same polynucleotide or polypeptide, separated by human intervention from some or all of the co-existing materials in the natural system, is isolated. In a preferred form, an isolated antibody, such as a monoclonal antibody, is substantially free of other polypeptides, particularly other polypeptides of animal origin, or other materials present in, for example, a hybridoma cell.

According to aspects of the present invention, an antibody is provided in a highly purified form, i.e., greater than 95% pure, such as greater than 99% pure.

Generally described, antibodies contain heavy chain polypeptides and light chain polypeptides. Antigen recognition is mediated by variable regions of the heavy and light chains. Complementarity determining region (CDR) refers to polypeptide regions within the variable region of heavy and light chains. Three CDRs (CDR1, CDR2 and CDR3) are present in each light chain variable region ($V_L$) and each heavy chain variable region (VH). The CDRs are generally responsible for specific antigen recognition properties of the antibody or antigen-binding fragment.

Antibodies according to aspects of the present invention are mouse monoclonal antibodies. Seven classes of anti-N69 mouse mAbs with different combinations of VH/VL sequences are provided according to aspects of the present invention: Class I: characterized by heavy chain variable region 1 (VH1) and light chain variable region 1 (VL1) include three separately isolated hybridomas and the monoclonal antibodies they produce wherein the hybridomas and antibodies are called 1D6, 2A8, and 2C1; Class II: characterized by heavy chain variable region 1 (VH1) and light chain variable region 2 (VL2) include three separately isolated hybridomas and the monoclonal antibodies they produce wherein the hybridomas and antibodies are called: 2D11, 2F11, 3F3; Class III: characterized by heavy chain variable region 2 (VH2) and light chain variable region 3 (VL3) include three separately isolated hybridomas and the monoclonal antibodies they produce wherein the hybridomas and antibodies are called: 1E11, 3B6, 3E5; Class IV: characterized by heavy chain variable region 3 (VH3) and light chain variable region 4 (VL4) include an isolated hybridoma and the monoclonal antibody produced wherein the hybridoma and antibody is called: 3H5; Class V: characterized by heavy chain variable region 3 (VH3) and light chain variable region 5 (VL5) include an isolated hybridoma and the monoclonal antibody produced wherein the hybridoma and antibody is called: 2H3; Class VI: characterized by heavy chain variable region 3 (VH3) and light chain variable region 6 (VL6) include an isolated hybridoma and the monoclonal antibody produced wherein the hybridoma and antibody is called: 4F5; and Class VII: characterized by heavy chain variable region 3 (VH3) and light chain variable region 7 (VL7) include an isolated hybridoma and the monoclonal antibody produced wherein the hybridoma and antibody is called: 2D9.

All of the mAbs described, 1D6, 2A8, 2C1, 2D11, 2F11, 3F3, 1E11, 3B6, 3E5, 3H5, 2H3, 4F5, and 2D9, have high affinity to HcTnT-N69 both when it resides in intact HcTnT and as isolated (free, also known as cleaved) HcTnT-N69 peptide. Some of these antibodies have higher affinity to free HcTnT-N69; whereas others have higher affinity to HcTnT-N69 when present in intact HcTnT. Antibodies of the present invention having differing affinities for free HcTnT-N69 or HcTnT-N69 when present in intact HcTnT provide the ability to distinguish isolated (free) HcTnT-N69 from HcTnT-N69 when present in intact HcTnT in immunological detection methods.

The term "intact HcTnT" as used herein refers to an HcTnT protein wherein the N-terminal fragment of human cardiac troponin T (HcTnT-N69, SEQ ID NO:1), or a cleavage variant thereof, has not been cleaved from the remainder of the HcTnT protein.

Represented by Class I, Class II and Class IV, several mAbs show higher affinity to the epitope HcTnT-N69 residing in intact HcTnT compared to the epitope in isolated HcTnT-N69 peptide.

Represented by Class III, several anti-N69 mAbs show higher affinity to isolated (free also known as cleaved) HcTnT-N69 peptide compared to intact HcTnT.

Hybridoma cells which produce these mouse monoclonal antibodies are provided according to aspects of the present invention, including hybridoma 1D6 which expresses mouse monoclonal antibody 1D6; hybridoma 2A8 which expresses mouse monoclonal antibody 2A8; hybridoma 2C1 which expresses mouse monoclonal antibody 2C1; hybridoma 1E11 which expresses mouse monoclonal antibody 1E11; hybridoma 3B6 which expresses mouse monoclonal antibody 3B6; hybridoma 3E5 which expresses mouse monoclonal antibody 3E5; hybridoma 2D9 which expresses mouse monoclonal antibody 2D9; hybridoma 2D11 which expresses mouse monoclonal antibody 2D11; hybridoma 2F11 which expresses mouse monoclonal antibody 2F11; hybridoma 3F3 which expresses mouse monoclonal antibody 3F3; hybridoma 2H3 which expresses mouse monoclonal antibody 2H3; hybridoma 3H5 which expresses mouse monoclonal antibody 3H5; and hybridoma 4F5 which expresses mouse monoclonal antibody 4F5.

Substitution at one or more amino acids in a CDR is possible while retaining specific antigen-binding function, particularly for those amino acid residues that do not contact the antigen. Such substitutions may be made at positions identified and known in the art or may be made empirically.

Class I: mAbs 1D6, 2A8, 2C1

Class I mAbs are characterized by heavy chain variable region 1 (VH1, SEQ ID NO:2) and light chain variable region 1 (VL1, SEQ ID NO:3) include three separately isolated hybridomas and the monoclonal antibodies they produce wherein the hybridomas and antibodies are called 1D6, 2A8, and 2C1. An example of a monoclonal antibody according to aspects of the present invention which is characterized by specific binding to HcTnT-N69 or HcTnT-neo is a Class I mAb represented by 1D6, which includes a variable heavy chain region (VH) of SEQ ID NO:2 (VH1) and a variable light chain region (VL) of (SEQ ID NO:3) (VL1).

According to aspects of the present invention, a monoclonal antibody or an antigen-binding fragment thereof which is characterized by specific binding to HcTnT-N69 or HcTnT-neo includes a heavy chain variable region including the amino acid sequence SEQ ID NO:2, or a variant thereof. The variant includes an amino acid sequence having at least 70%, at least 75%, at least 80%, at least 85%, at least 90%, at least 95%, at least 96%, at least 97%, at least 98%, or at least 99% identity with the amino acid sequence of SEQ ID NO:2, and retains at least a substantial proportion (at least about 50%, 60%, 70%, 80%, 90%, 95% or more) of the affinity/avidity and/or the specificity/selectivity of the parent antibody 1D6 and in some cases such an antibody may be associated with greater affinity, selectivity and/or specificity than the parent antibody 1D6.

SEQ ID NO:2 IgG1 Monoclonal Antibody 1D6 Variable Heavy Chain Region (109 Amino Acids)

```
GPELVKPGASVKISCKTSGYTFTENTIHWVKQSHG

KSLEWVGGINPNNGGTNYNQKFKGRAALTVDKSSS

TAYMELRSLTSEDSAVYYCARSWDWFAYWGQGTLV

TVSA
```

According to aspects of the present invention, a monoclonal antibody or an antigen-binding fragment thereof which is characterized by specific binding to HcTnT-N69 or HcTnT-neo includes a light chain variable domain including the amino acid sequence SEQ ID NO:3, or a variant thereof. The variant includes an amino acid sequence having at least 70%, at least 75%, at least 80%, at least 85%, at least 90%, at least 95%, at least 96%, at least 97%, at least 98%, or at least 99% identity with the amino acid sequence as set forth in SEQ ID NO:3, and retains at least a substantial proportion (at least about 50%, 60%, 70%, 80%, 90%, 95% or more) of the affinity/avidity and/or the specificity/selectivity of the parent antibody 1D6 and in some cases such an antibody may be associated with greater affinity, selectivity and/or specificity than the parent antibody 1D6.

SEQ ID NO:3 Monoclonal Antibody 1D6 Kappa Variable Light Chain Region (106 Amino Acids)

```
LSLPVSLGDQASISCRSSQSLVHSNGNTYLHWYLQK

PGQSPKLLVYKVSNRFSGVPDRFSGSGSGTDFTLKI

IRVEAEDLGVYFCSQSTRIPFTFGSGTKLEMKRA
```

According to aspects of the present invention, a monoclonal antibody or an antigen-binding fragment thereof which is characterized by specific binding to HcTnT-N69 or HcTnT-neo includes a heavy chain variable region including the amino acid sequence of SEQ ID NO:2, or a variant thereof, and a light chain variable region including the amino acid sequence of SEQ ID NO:3, or a variant thereof. The variant includes an amino acid sequence having at least 70%, at least 75%, at least 80%, at least 85%, at least 90%, at least 95%, at least 96%, at least 97%, at least 98%, or at least 99% identity with the amino acid sequence of SEQ ID NO:2 or SEQ ID NO:3, and retains at least a substantial proportion (at least about 50%, 60%, 70%, 80%, 90%, 95% or more) of the affinity/avidity and/or the specificity/selectivity of the parent antibody and in some cases such an antibody may be associated with greater affinity, selectivity and/or specificity than the parent antibody 1D6.

According to aspects of the present invention, a monoclonal antibody or an antigen-binding fragment thereof which is characterized by specific binding to HcTnT-N69 or HcTnT-neo includes a variable heavy chain region, or a variant thereof, encoded by the nucleotide sequence of SEQ ID NO:4 or a variant of SEQ ID NO:4 which hybridizes to the complement of SEQ ID NO:4 under stringent hybridization conditions.

SEQ ID NO:4 IgG1 Monoclonal Antibody 1D6 Variable Heavy Chain Region (327 Nucleotides) (VH1)

```
GGACCTGAACTGGTGAAGCCTGGGGCTTCAGTGAA

GATTTCCTGTAAGACTTCTGGATACACATTCACTG

AAAACACCATACACTGGGTGAAGCAGAGCCATGGA

AAGAGCCTTGAGTGGGTTGGAGGTATCAATCCTAA

CAATGGTGGCACTAATTACAATCAGAAATTTAAGG

GCAGGGCCGCATTGACTGTAGACAAGTCCTCCAGC

ACAGCCTACATGGAGCTCCGCAGCCTGACATCTGA

AGATTCTGCAGTCTATTATTGTGCAAGATCCTGGG

ACTGGTTTGCTTACTGGGGCCAAGGGACTCTGGTC

ACTGTCTCTGCA
```

According to aspects of the present invention, the isolated antibody or an antigen-binding fragment includes a variable light chain region, or a variant thereof, encoded by the nucleotide sequence of SEQ ID NO:5 or a variant of SEQ ID NO:5 which hybridizes to the complement of SEQ ID NO:5 under stringent hybridization conditions.

SEQ ID NO:5 IgG1 Monoclonal Antibody 1D6 Variable Light Chain Region (318 Nucleotides) (VL1)

```
CTCTCCCTGCCTGTCAGTCTTGGAGATCAGGCCTC

CATCTCTTGCAGATCTAGTCAGAGCCTTGTACACA

GTAATGGAAACACCTATTTACATTGGTACCTGCAG

AAGCCAGGCCAGTCTCCAAAGCTCCTGGTCTACAA

AGTTTCCAACCGATTTTCTGGGGTCCCAGACAGGT

TCAGTGGCAGTGGATCAGGGACAGATTTCACACTC

AAGATCATCAGAGTGGAGGCTGAGGATCTGGGAGT

TTATTTCTGCTCTCAAAGTACACGTATTCCATTCA

CGTTCGGCTCGGGGACAAAGTTGGAAATGAAACGG

GCT
```

According to aspects of the present invention, a monoclonal antibody or an antigen-binding fragment thereof which is characterized by specific binding to HcTnT-N69 or HcTnT-neo includes: 1) a variable heavy chain region, or a variant thereof, encoded by the nucleotide sequence of SEQ ID NO:4 or a variant of SEQ ID NO:4 which hybridizes to the complement of SEQ ID NO:4 under stringent hybridization conditions and 2) a variable light chain region, or a variant thereof, encoded by the nucleotide sequence of SEQ ID NO:5 or a variant of SEQ ID NO:5 which hybridizes to the complement of SEQ ID NO:5 under stringent hybridization conditions.

Class II: mAbs 2D11, 2F11, 3F3

Class II mAbs are characterized by heavy chain variable region 1 (VH1) and light chain variable region 2 (VL2) include three separately isolated hybridomas and the monoclonal antibodies they produce wherein the hybridomas and antibodies are called: 2D11, 2F11, 3F3.

An example of a monoclonal antibody of the present disclosure characterized by specific binding to HcTnT-N69 or HcTnT-neo is mAb 2D11, which includes a variable heavy chain region of SEQ ID NO:2 (VH1) and a variable light chain region of SEQ ID NO:6 (VL2).

According to aspects of the present invention, a monoclonal antibody or an antigen-binding fragment thereof which is characterized by specific binding to HcTnT-N69 or HcTnT-neo includes a light chain variable domain including the amino acid sequence of SEQ ID NO:6, or a variant thereof. The variant includes an amino acid sequence having at least 70%, at least 75%, at least 80%, at least 85%, at least 90%, at least 95%, at least 96%, at least 97%, at least 98%, or at least 99% identity with the amino acid sequence as set forth in SEQ ID NO:6, and retains at least a substantial proportion (at least about 50%, 60%, 70%, 80%, 90%, 95% or more) of the affinity/avidity and/or the specificity/selectivity of the parent antibody and in some cases such an antibody may be associated with greater affinity, selectivity and/or specificity than the parent antibody 2D11.

SEQ ID NO:6 Kappa Monoclonal Antibody 2D11 Variable Light Chain Region (106 Amino Acids)

```
LSLPVSLGDQASISCRSSQSLVHSNGNTYLHWYLQK

PGQSPKLLVYKVSNRFSGVPDRFSGSGSGTDFTLKI

IRVKAEDLGVYFCSQSTRIPFTFGSGTKLEMKRA
```

According to aspects of the present invention, a monoclonal antibody or an antigen-binding fragment thereof which is characterized by specific binding to HcTnT-N69 or HcTnT-neo includes a heavy chain variable region including the amino acid sequence of SEQ ID NO:2, or a variant thereof, and a light chain variable region including the amino acid sequence of SEQ ID NO:6, or a variant thereof. The variant includes an amino acid sequence having at least 70%, at least 75%, at least 80%, at least 85%, at least 90%, at least 95%, at least 96%, at least 97%, at least 98%, or at least 99% identity with the amino acid sequence as set forth in SEQ ID NO:2 or SEQ ID NO:6, and retains at least a substantial proportion (at least about 50%, 60%, 70%, 80%, 90%, 95% or more) of the affinity/avidity and/or the specificity/selectivity of the parent antibody and in some cases such an antibody may be associated with greater affinity, selectivity and/or specificity than the parent antibody 2D11.

According to aspects of the present invention, a monoclonal antibody or an antigen-binding fragment thereof which is characterized by specific binding to HcTnT-N69 or HcTnT-neo includes a variable light chain region, or a variant thereof, encoded by the nucleotide sequence of SEQ ID NO:7 or a variant of SEQ ID NO:7 which hybridizes to the complement of SEQ ID NO:7 under stringent hybridization conditions.

SEQ ID NO:7 IgG1 Monoclonal Antibody 2D11 Variable Light Chain Region (318 Nucleotides)

```
CTCTCCCTGCCTGTCAGTCTTGGAGATCAGGCCTCC

ATCTCTTGCAGATCTAGTCAGAGCCTTGTACACAGT

AATGGAAACACCTATTTACATTGGTACCTGCAGAAG

CCAGGCCAGTCTCCAAAGCTCCTGGTCTACAAAGTT

TCCAACCGATTTTCTGGGGTCCCAGACAGGTTCAGT

GGCAGTGGATCAGGGACAGATTTCACACTCAAGATC

ATCAGAGTGAAGGCTGAGGATCTGGGAGTTTATTTC
```

-continued
TGCTCTCAAAGTACACGTATTCCATTCACGTTCGGC

TCGGGGACAAAGTTGGAAATGAAACGGGCT

According to aspects of the present invention, a monoclonal antibody or an antigen-binding fragment thereof which is characterized by specific binding to HcTnT-N69 or HcTnT-neo includes: 1) a variable heavy chain region, or a variant thereof, encoded by the nucleotide sequence of SEQ ID NO:4 or a variant of SEQ ID NO:4 which hybridizes to the complement of SEQ ID NO:4 under stringent hybridization conditions and 2) a variable light chain region, or a variant thereof, encoded by the nucleotide sequence of SEQ ID NO:7 or a variant of SEQ ID NO:7 which hybridizes to the complement of SEQ ID NO:7 under stringent hybridization conditions.

Class III: mAbs 1E11, 3B6, 3E5

Class III mAbs are characterized by heavy chain variable region 2 (VH2) and light chain variable region 3 (VL3) include three separately isolated hybridomas and the monoclonal antibodies they produce wherein the hybridomas and antibodies are called: 1E11, 3B6, 3E5.

An example of a monoclonal antibody of the present disclosure characterized by specific binding to: HcTnT-N69 or HcTnT-neo is mAb 1E11, which includes a variable heavy chain region of SEQ ID NO:8 and a variable light chain region of SEQ ID NO:9.

According to aspects of the present invention, a monoclonal antibody or an antigen-binding fragment thereof which is characterized by specific binding to HcTnT-N69 or HcTnT-neo includes a heavy chain variable region including the amino acid sequence of SEQ ID NO:8, or a variant thereof. The variant includes an amino acid sequence having at least 70%, at least 75%, at least 80%, at least 85%, at least 90%, at least 95%, at least 96%, at least 97%, at least 98%, or at least 99% identity with the amino acid sequence as set forth in SEQ ID NO:8, and retains at least a substantial proportion (at least about 50%, 60%, 70%, 80%, 90%, 95% or more) of the affinity/avidity and/or the specificity/selectivity of the parent antibody and in some cases such an antibody may be associated with greater affinity, selectivity and/or specificity than the parent antibody 1E11.

SEQ ID NO:8 IgG3 Monoclonal Antibody 1E11 Variable Heavy Chain Region (112 Amino Acids)

GAELAKPGASVKMSCKASGYTFTTYWMHWVKQRPGQGLEWIGFINPST

GYTEYNQKFKDKATLTADKSSSTAYMQLSSLTSGDSAVYYCARKSFAY

WGHGTLVTVSAATTTA

According to aspects of the present invention, a monoclonal antibody or an antigen-binding fragment thereof which is characterized by specific binding to HcTnT-N69 or HcTnT-neo includes a light chain variable domain including the amino acid sequence of SEQ ID NO:9, or a variant thereof. The variant includes an amino acid sequence having at least 70%, at least 75%, at least 80%, at least 85%, at least 90%, at least 95%, at least 96%, at least 97%, at least 98%, or at least 99% identity with the amino acid sequence as set forth in SEQ ID NO:9, and retains at least a substantial proportion (at least about 50%, 60%, 70%, 80%, 90%, 95% or more) of the affinity/avidity and/or the specificity/selectivity of the parent antibody and in some cases such an antibody may be associated with greater affinity, selectivity and/or specificity than the parent antibody1E11.

SEQ ID NO:9 Kappa Monoclonal Antibody 1E11 Variable Light Chain Region (106 Amino Acids)

LTLSVTIGQPASISCKSSQSLLHSDGKTYLNWLLQRPGQSPKRLIYLV

SKLDSGVPDRFTGSGSGTDFTLKISRVEAEDVGIYYCWQGTQFPRTFG

GGTKLEIKRA

According to aspects of the present invention, a monoclonal antibody or an antigen-binding fragment thereof which is characterized by specific binding to HcTnT-N69 or HcTnT-neo includes a heavy chain variable region including the amino acid sequence of SEQ ID NO:8, or a variant thereof, and a light chain variable region including the amino acid sequence of SEQ ID NO:9, or a variant thereof. The variant includes an amino acid sequence having at least 70%, at least 75%, at least 80%, at least 85%, at least 90%, at least 95%, at least 96%, at least 97%, at least 98%, or at least 99% identity with the amino acid sequence as set forth in SEQ ID NO:8 or SEQ ID NO:9, and retains at least a substantial proportion (at least about 50%, 60%, 70%, 80%, 90%, 95% or more) of the affinity/avidity and/or the specificity/selectivity of the parent antibody and in some cases such an antibody may be associated with greater affinity, selectivity and/or specificity than the parent antibody 1E11.

According to aspects of the present invention, a monoclonal antibody or an antigen-binding fragment thereof which is characterized by specific binding to HcTnT-N69 or HcTnT-neo includes a variable heavy chain region, or a variant thereof, encoded by the nucleotide sequence of SEQ ID NO:10 or a variant of SEQ ID NO:10 which hybridizes to the complement of SEQ ID NO:10 under stringent hybridization conditions.

SEQ ID NO:10 IgG3 Monoclonal Antibody 1E11 Variable Heavy Chain Region (336 Nucleotides)

GGGGCTGAACTGGCAAAACCTGGGGCCTCAGTGAAGATGTCCTGCAAG

GCTTCTGGTTACACCTTTACTACTTACTGGATGCACTGGGTAAAACAG

AGGCCTGGACAGGGTCTGGAATGGATTGGATTCATTAATCCTAGTACT

GGTTATACTGAATACAATCAGAAGTTCAAGGACAAGGCCACATTGACT

GCAGACAAATCCTCCAGCACAGCCTACATGCAACTGAGCAGCCTGACA

TCTGGGGACTCTGCAGTCTATTACTGTGCAAGAAAGAGTTTTGCTTAC

TGGGGCCACGGGACTCTGGTCACTGTCTCTGCAGCTACAACAACAGCC

According to aspects of the present invention, a monoclonal antibody or an antigen-binding fragment thereof which is characterized by specific binding to HcTnT-N69 or HcTnT-neo includes a variable light chain region, or a variant thereof, encoded by the nucleotide sequence of SEQ ID NO:11 or a variant of SEQ ID NO:11 which hybridizes to the complement of SEQ ID NO:11 under stringent hybridization conditions.

SEQ ID NO:11 IgG3 Monoclonal Antibody 1E11 Variable Light Chain Region (318 Nucleotides)

CTCACTTTGTCGGTTACCATTGGACAACCAGCCTCCATCTCTTGCAAG

TCAAGTCAGAGCCTCTTACATAGTGATGGAAAGACATATTTGAATTGG

TTGTTACAGAGGCCAGGCCAGTCTCCAAAGCGCCTAATCTATCTGGTG

```
-continued
TCTAAACTGGACTCTGGAGTCCCTGACAGGTTCACTGGCAGTGGATCA

GGGACAGATTTCACACTGAAAATCAGCAGAGTGGAGGCTGAGGATGTG

GGAATTTATTATTGCTGGCAAGGTACACAATTTCCTCGGACGTTCGGT

GGAGGCACCAAGCTGGAAATCAAACGGGCT
```

According to aspects of the present invention, a monoclonal antibody or an antigen-binding fragment thereof which is characterized by specific binding to HcTnT-N69 or HcTnT-neo includes: 1) a variable heavy chain region, or a variant thereof, encoded by the nucleotide sequence of SEQ ID NO:10 or a variant of SEQ ID NO:10 which hybridizes to the complement of SEQ ID NO:10 under stringent hybridization conditions and 2) a variable light chain region, or a variant thereof, encoded by the nucleotide sequence of SEQ ID NO:11 or a variant of SEQ ID NO:11 which hybridizes to the complement of SEQ ID NO:11 under stringent hybridization conditions.

Class IV: mAb 3H5

Class IV is characterized by heavy chain variable region 3 (VH3) and light chain variable region 4 (VL4) include an isolated hybridoma and the monoclonal antibody produced wherein the hybridoma and antibody is called: 3H5.

An example of a monoclonal antibody of the present disclosure characterized by specific binding to: HcTnT-N69 or HcTnT-neo is mAb 3H5, which includes a variable heavy chain region of SEQ ID NO:12 and a variable light chain region of SEQ ID NO:13.

According to aspects of the present invention, a monoclonal antibody or an antigen-binding fragment thereof which is characterized by specific binding to HcTnT-N69 or HcTnT-neo includes a heavy chain variable region including the amino acid sequence SEQ ID NO:12, or a variant thereof. The variant includes an amino acid sequence having at least 70%, at least 75%, at least 80%, at least 85%, at least 90%, at least 95%, at least 96%, at least 97%, at least 98%, or at least 99% identity with the amino acid sequence as set forth in SEQ ID NO:12, and retains at least a substantial proportion (at least about 50%, 60%, 70%, 80%, 90%, 95% or more) of the affinity/avidity and/or the specificity/selectivity of the parent antibody and in some cases such an antibody may be associated with greater affinity, selectivity and/or specificity than the parent antibody 3H5.

SEQ ID NO:12 IgM Monoclonal Antibody 3H5 Variable Heavy Chain Region (113 Amino Acids)

GGGLVQPKGSLKLSCAASGFTFNTYAMNWVRQAPGKGLEWVARIRSKS

NNYATYYADSVKDRFTISRDDSQSMLYLQMNNLKTEDTAMYYCVRHDG

VAWFAYWGQGTLVTVSA

According to aspects of the present invention, a monoclonal antibody or an antigen-binding fragment thereof which is characterized by specific binding to HcTnT-N69 or HcTnT-neo includes a light chain variable domain including the amino acid sequence SEQ ID NO:13, or a variant thereof. The variant includes an amino acid sequence having at least 70%, at least 75%, at least 80%, at least 85%, at least 90%, at least 95%, at least 96%, at least 97%, at least 98%, or at least 99% identity with the amino acid sequence as set forth in SEQ ID NO:13, and retains at least a substantial proportion (at least about 50%, 60%, 70%, 80%, 90%, 95% or more) of the affinity/avidity and/or the specificity/selectivity of the parent antibody and in some cases such an antibody may be associated with greater affinity, selectivity and/or specificity than the parent antibody 3H5.

SEQ ID NO:13 Kappa Monoclonal Antibody 3H5 Variable Light Chain Region (106 Amino Acids)

LSLPVSLGDQASISCRSSQSIVHSNGNTYLEWYLQKPGQSPKLLIYKV

SNRFSGVPDRFSGSGSGTDFTLKISRVEAEDLGVYYCFQGSHVPPTFG

AGTKLELKRA

According to aspects of the present invention, a monoclonal antibody or an antigen-binding fragment thereof which is characterized by specific binding to HcTnT-N69 or HcTnT-neo includes a heavy chain variable region including the amino acid sequence of SEQ ID NO:12, or a variant thereof, and a light chain variable region including the amino acid sequence of SEQ ID NO:13, or a variant thereof. The variant includes an amino acid sequence having at least 70%, at least 75%, at least 80%, at least 85%, at least 90%, at least 95%, at least 96%, at least 97%, at least 98%, or at least 99% identity with the amino acid sequence as set forth in SEQ ID NO:12 or SEQ ID NO:13, and retains at least a substantial proportion (at least about 50%, 60%, 70%, 80%, 90%, 95% or more) of the affinity/avidity and/or the specificity/selectivity of the parent antibody and in some cases such an antibody may be associated with greater affinity, selectivity and/or specificity than the parent antibody 3H5.

According to aspects of the present invention, a monoclonal antibody or an antigen-binding fragment thereof which is characterized by specific binding to HcTnT-N69 or HcTnT-neo includes a variable heavy chain region, or a variant thereof, encoded by the nucleotide sequence of SEQ ID NO:14 or a variant of SEQ ID NO:14 which hybridizes to the complement of SEQ ID NO:14 under stringent hybridization conditions.

SEQ ID NO:14 IgM Monoclonal Antibody 3H5 Variable Heavy Chain Region (339 Nucleotides)

GGTGGAGGATTGGTGCAGCCTAAAGGGTCATTGAAACTCTCATGTGCA

GCCTCTGGATTCACCTTCAATACCTACGCCATGAACTGGGTCCGCCAG

GCTCCAGGAAAGGGTTTGGAATGGGTTGCTCGCATAAGAAGTAAAAGT

AATAATTATGCAACATATTATGCCGATTCAGTGAAAGACAGGTTCACC

ATCTCCAGAGATGATTCACAAAGCATGCTCTATCTGCAAATGAACAAC

TTGAAAACTGAGGACACAGCCATGTATTACTGTGTGAGACATGATGGT

GTCGCCTGGTTTGCTTACTGGGGCCAAGGGACTCTGGTCACTGTCTCT

GCA

According to aspects of the present invention, a monoclonal antibody or an antigen-binding fragment thereof which is characterized by specific binding to HcTnT-N69 or HcTnT-neo includes a variable light chain region, or a variant thereof, encoded by the nucleotide sequence of SEQ ID NO:15 or a variant of SEQ ID NO:15 which hybridizes to the complement of SEQ ID NO:15 under stringent hybridization conditions.

SEQ ID NO:15 IgM Monoclonal Antibody 3H5 Variable Light Chain Region (318 Nucleotides)

```
CTCTCCCTGCCTGTCAGTCTTGGAGATCAAGCCTCCATCTCTTGCAGA
TCTAGTCAGAGCATTGTACATAGTAATGGAAACACCTATTTAGAATGG
TACCTGCAGAAACCAGGCCAGTCTCCAAAGCTCCTGATCTACAAAGTT
TCCAACCGATTTTCTGGGGTCCCAGACAGGTTCAGTGGCAGTGGATCA
GGGACAGATTTCACACTCAAGATCAGCAGAGTGGAGGCTGAGGATCTG
GGAGTTTATTACTGCTTTCAAGGTTCACATGTTCCTCCCACGTTCGGT
GCTGGGACCAAGCTGGAGCTGAAACGGGCT
```

According to aspects of the present invention, a monoclonal antibody or an antigen-binding fragment thereof which is characterized by specific binding to HcTnT-N69 or HcTnT-neo includes: 1) a variable heavy chain region, or a variant thereof, encoded by the nucleotide sequence of SEQ ID NO:14 or a variant of SEQ ID NO:14 which hybridizes to the complement of SEQ ID NO:14 under stringent hybridization conditions and 2) a variable light chain region, or a variant thereof, encoded by the nucleotide sequence of SEQ ID NO:15 or a variant of SEQ ID NO:15 which hybridizes to the complement of SEQ ID NO:15 under stringent hybridization conditions.

Class V: mAb 2H3

Class V is characterized by heavy chain variable region 3 (VH3) and light chain variable region 5 (VL5) include an isolated hybridoma and the monoclonal antibody produced wherein the hybridoma and antibody is called: 2H3.

An example of a monoclonal antibody of the present disclosure characterized by specific binding to: HcTnT-N69 or HcTnT-neo is mAb 2H3, which includes a variable heavy chain region of SEQ ID NO:12 and a variable light chain region of SEQ ID NO:16.

According to aspects of the present invention, a monoclonal antibody or an antigen-binding fragment thereof which is characterized by specific binding to HcTnT-N69 or HcTnT-neo includes a light chain variable domain including the amino acid sequence SEQ ID NO:16, or a variant thereof. The variant includes an amino acid sequence having at least 70%, at least 75%, at least 80%, at least 85%, at least 90%, at least 95%, at least 96%, at least 97%, at least 98%, or at least 99% identity with the amino acid sequence as set forth in SEQ ID NO:16, and retains at least a substantial proportion (at least about 50%, 60%, 70%, 80%, 90%, 95% or more) of the affinity/avidity and/or the specificity/selectivity of the parent antibody and in some cases such an antibody may be associated with greater affinity, selectivity and/or specificity than the parent antibody 2H3.

SEQ ID NO:16 Kappa Monoclonal Antibody 2H3 Variable Light Chain Region (106 Amino Acids)

```
LSLPVSLGDQASISCRSSQSIVHSNGNTYLEWYLQKPGQSPKLLIYKV
SNRFSGVPDRFSGSGSGTDFTLKISRVKAEDLGVYYCFQGSHVPPTFG
AGTKLELKRA
```

According to aspects of the present invention, a monoclonal antibody or an antigen-binding fragment thereof which is characterized by specific binding to HcTnT-N69 or HcTnT-neo includes a heavy chain variable region including the amino acid sequence of SEQ ID NO:12, or a variant thereof, and a light chain variable region including the amino acid sequence of SEQ ID NO:16, or a variant thereof. The variant includes an amino acid sequence having at least 70%, at least 75%, at least 80%, at least 85%, at least 90%, at least 95%, at least 96%, at least 97%, at least 98%, or at least 99% identity with the amino acid sequence as set forth in SEQ ID NO:12 or SEQ ID NO:16, and retains at least a substantial proportion (at least about 50%, 60%, 70%, 80%, 90%, 95% or more) of the affinity/avidity and/or the specificity/selectivity of the parent antibody and in some cases such an antibody may be associated with greater affinity, selectivity and/or specificity than the parent antibody 2H3.

According to aspects of the present invention, a monoclonal antibody or an antigen-binding fragment thereof which is characterized by specific binding to HcTnT-N69 or HcTnT-neo includes a variable light chain region, or a variant thereof, encoded by the nucleotide sequence of SEQ ID NO:17 or a variant of SEQ ID NO:17 which hybridizes to the complement of SEQ ID NO:17 under stringent hybridization conditions.

SEQ ID NO:17 IgM Monoclonal Antibody 2H3 Variable Light Chain Region (318 Nucleotides)

```
CTCTCCCTGCCTGTCAGTCTTGGAGATCAAGCCTCCATCTCTTGCAGA
TCTAGTCAGAGCATTGTACATAGTAATGGAAACACCTATTTAGAATGG
TACCTGCAGAAACCAGGCCAGTCTCCAAAGCTCCTGATCTACAAAGTT
TCCAACCGATTTTCTGGGGTCCCAGACAGGTTCAGTGGCAGTGGATCA
GGGACAGATTTCACACTCAAGATCAGCAGAGTGAAGGCTGAGGATCTG
GGAGTTTATTACTGCTTTCAAGGTTCACATGTTCCTCCCACGTTCGGT
GCTGGGACCAAGCTGGAGCTGAAACGGGCT
```

According to aspects of the present invention, a monoclonal antibody or an antigen-binding fragment thereof which is characterized by specific binding to HcTnT-N69 or HcTnT-neo includes: 1) a variable heavy chain region, or a variant thereof, encoded by the nucleotide sequence of SEQ ID NO:14 or a variant of SEQ ID NO:14 which hybridizes to the complement of SEQ ID NO:14 under stringent hybridization conditions and 2) a variable light chain region, or a variant thereof, encoded by the nucleotide sequence of SEQ ID NO:17 or a variant of SEQ ID NO:17 which hybridizes to the complement of SEQ ID NO:17 under stringent hybridization conditions.

Class VI: mAb 4F5

Class VI is characterized by heavy chain variable region 3 (VH3) and light chain variable region 6 (VL6) include an isolated hybridoma and the monoclonal antibody produced wherein the hybridoma and antibody is called: 4F5.

An example of a monoclonal antibody of the present disclosure characterized by specific binding to: HcTnT-N69 or HcTnT-neo is mAb 4F5, which includes a variable heavy chain region of SEQ ID NO:12 and a variable light chain region SEQ ID NO:18.

According to aspects of the present invention, a monoclonal antibody or an antigen-binding fragment thereof which is characterized by specific binding to HcTnT-N69 or HcTnT-neo includes a light chain variable domain including the amino acid sequence of SEQ ID NO:18, or a variant thereof. The variant includes an amino acid sequence having at least 70%, at least 75%, at least 80%, at least 85%, at least 90%, at least 95%, at least 96%, at least 97%, at least 98%, or at least 99% identity with the amino acid sequence as set forth in SEQ ID NO:18, and retains at least a substantial proportion (at least about 50%, 60%, 70%, 80%, 90%, 95% or more) of the affinity/avidity and/or the specificity/selectivity of the parent antibody and in some cases such an antibody may be associated with greater affinity, selectivity and/or specificity than the parent antibody 4F5.

SEQ ID NO:18 Kappa Monoclonal Antibody 4F5 Variable Light Chain Region (106 Amino Acids)

LSLPVSLGDQASISCKSSQSIVHSNGNTYLEWYLQKPGQSPKLLIYKV

SNRFSGVPDRFSGSGSGTDFTLKISRVKAEDLGVYYCFQGSHVPPTFG

AGTKLELKRA

According to aspects of the present invention, a monoclonal antibody or an antigen-binding fragment thereof which is characterized by specific binding to HcTnT-N69 or HcTnT-neo includes a heavy chain variable region including the amino acid sequence of SEQ ID NO:12, or a variant thereof, and a light chain variable region including the amino acid sequence of SEQ ID NO:18, or a variant thereof. The variant includes an amino acid sequence having at least 70%, at least 75%, at least 80%, at least 85%, at least 90%, at least 95%, at least 96%, at least 97%, at least 98%, or at least 99% identity with the amino acid sequence as set forth in SEQ ID NO:12 or SEQ ID NO:18, and retains at least a substantial proportion (at least about 50%, 60%, 70%, 80%, 90%, 95% or more) of the affinity/avidity and/or the specificity/selectivity of the parent antibody and in some cases such an antibody may be associated with greater affinity, selectivity and/or specificity than the parent antibody 4F5.

According to aspects of the present invention, a monoclonal antibody or an antigen-binding fragment thereof which is characterized by specific binding to HcTnT-N69 or HcTnT-neo includes a variable light chain region, or a variant thereof, encoded by the nucleotide sequence of SEQ ID NO:19 or a variant of SEQ ID NO:19 which hybridizes to the complement of SEQ ID NO:19 under stringent hybridization conditions.

SEQ ID NO:19 IgM Monoclonal Antibody 4F5 Variable Light Chain Region (318 Nucleotides)

CTCTCCCTGCCTGTCAGTCTTGGAGATCAAGCCTCCATCTCTTGCAGA

TCTAGTCAGAGCATTGTACATAGTAATGGAAACACCTATTTAGAATGG

TACCTGCAGAAACCAGGCCAGTCTCCAAAGCTCCTGATCTACAAAGTT

TCCAACCGATTTTCTGGGGTCCCAGACAGGTTCAGTGGCAGTGGATCA

GGGACAGATTTCACACTCAAGATCAGCAGAGTGAAGGCTGAGGATCTG

GGAGTTTATTACTGCTTTCAAGGTTCACATGTTCCTCCCACGTTCGGT

GCTGGGACCAAGCTGGAGCTGAAACGGGCT

According to aspects of the present invention, a monoclonal antibody or an antigen-binding fragment thereof which is characterized by specific binding to HcTnT-N69 or HcTnT-neo includes: 1) a variable heavy chain region, or a variant thereof, encoded by the nucleotide sequence of SEQ ID NO:14 or a variant of SEQ ID NO:14 which hybridizes to the complement of SEQ ID NO:14 under stringent hybridization conditions and 2) a variable light chain region, or a variant thereof, encoded by the nucleotide sequence of SEQ ID NO:19 or a variant of SEQ ID NO:19 which hybridizes to the complement of SEQ ID NO:19 under stringent hybridization conditions.

Class VII: mAb 2D9

Class VII is characterized by heavy chain variable region 3 (VH3) and light chain variable region 7 (VL7) include an isolated hybridoma and the monoclonal antibody produced wherein the hybridoma and antibody is called: 2D9.

An example of a monoclonal antibody of the present disclosure characterized by specific binding to: HcTnT-N69 or HcTnT-neo is mAb 2D9, which includes a variable heavy chain region of SEQ ID NO:12 and a variable light chain region of SEQ ID NO:20.

According to aspects of the present invention, a monoclonal antibody or an antigen-binding fragment thereof which is characterized by specific binding to HcTnT-N69 or HcTnT-neo includes a light chain variable domain including the amino acid sequence SEQ ID NO:20, or a variant thereof. The variant includes an amino acid sequence having at least 70%, at least 75%, at least 80%, at least 85%, at least 90%, at least 95%, at least 96%, at least 97%, at least 98%, or at least 99% identity with the amino acid sequence as set forth in SEQ ID NO:20, and retains at least a substantial proportion (at least about 50%, 60%, 70%, 80%, 90%, 95% or more) of the affinity/avidity and/or the specificity/selectivity of the parent antibody and in some cases such an antibody may be associated with greater affinity, selectivity and/or specificity than the parent antibody 2D9.

SEQ ID NO:20 Kappa Monoclonal Antibody 2D9 Variable Light Chain Region (106 Amino Acids)

LSLPVSLGDQASISCKSSQSIVHSNGNTYLKWYLQKPGQSPKLLIYKV

SNRFSGVPDRFSGSGSGTDFTLKISRVKAEDLGVYYCFQGSHVPPTFG

AGTKLELKRA

According to aspects of the present invention, a monoclonal antibody or an antigen-binding fragment thereof which is characterized by specific binding to HcTnT-N69 or HcTnT-neo includes a heavy chain variable region including the amino acid sequence of SEQ ID NO:12, or a variant thereof, and a light chain variable region including the amino acid sequence of SEQ ID NO:20, or a variant thereof. The variant includes an amino acid sequence having at least 70%, at least 75%, at least 80%, at least 85%, at least 90%, at least 95%, at least 96%, at least 97%, at least 98%, or at least 99% identity with the amino acid sequence as set forth in SEQ ID NO:12 or SEQ ID NO:20, and retains at least a substantial proportion (at least about 50%, 60%, 70%, 80%, 90%, 95% or more) of the affinity/avidity and/or the specificity/selectivity of the parent antibody and in some cases such an antibody may be associated with greater affinity, selectivity and/or specificity than the parent antibody 2D9.

According to aspects of the present invention, a monoclonal antibody or an antigen-binding fragment thereof which is characterized by specific binding to HcTnT-N69 or HcTnT-neo includes a variable light chain region, or a variant thereof, encoded by the nucleotide sequence of SEQ ID NO:21 or a variant of SEQ ID NO:21 which hybridizes to the complement of SEQ ID NO:21 under stringent hybridization conditions.

SEQ ID NO:21 IgM Monoclonal Antibody 2D9 Variable Light Chain Region (318 Nucleotides)

CTCTCCCTGCCTGTCAGTCTTGGAGATCAAGCCTCCATCTCTTGCAGA

TCTAGTCAGAGCATTGTACATAGTAATGGAAACACCTATTTAAAATGG

TACCTGCAGAAACCAGGCCAGTCTCCAAAGCTCCTGATCTACAAAGTT

-continued

```
TCCAACCGATTTTCTGGGGTCCCAGACAGGTTCAGTGGCAGTGGATCA

GGGACAGATTTCACACTCAAGATCAGCAGAGTGAAGGCTGAGGATCTG

GGAGTTTATTACTGCTTTCAAGGTTCACATGTTCCTCCCACGTTCGGT

GCTGGGACCAAGCTGGAGCTGAAACGGGCT
```

According to aspects of the present invention, a monoclonal antibody or an antigen-binding fragment thereof which is characterized by specific binding to HcTnT-N69 or HcTnT-neo includes: 1) a variable heavy chain region, or a variant thereof, encoded by the nucleotide sequence of SEQ ID NO:14 or a variant of SEQ ID NO:14 which hybridizes to the complement of SEQ ID NO:14 under stringent hybridization conditions and 2) a variable light chain region, or a variant thereof, encoded by the nucleotide sequence of SEQ ID NO:21 or a variant of SEQ ID NO:21 which hybridizes to the complement of SEQ ID NO:21 under stringent hybridization conditions.

It will be appreciated by those of ordinary skill in the art that, due to the degenerate nature of the genetic code, alternate nucleic acid sequences encode the variable heavy chain regions, variable light chain regions and variants thereof disclosed herein and that such alternate nucleic acids may be used in compositions and methods described herein.

The terms "hybridization" and "hybridizes" refer to pairing and binding of complementary nucleic acids. Hybridization occurs to varying extents between two nucleic acids depending on factors such as the degree of complementarity of the nucleic acids, the melting temperature, Tm, of the nucleic acids and the stringency of hybridization conditions, as is well known in the art. The term "stringency of hybridization conditions" refers to conditions of temperature, ionic strength, and composition of a hybridization medium with respect to particular common additives such as formamide and Denhardt's solution. Determination of particular hybridization conditions relating to a specified nucleic acid is routine and is well known in the art, for instance, as described in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002. High stringency hybridization conditions are those which only allow hybridization of substantially complementary nucleic acids. Typically, nucleic acids having about 85-100% complementarity are considered highly complementary and hybridize under high stringency conditions. Intermediate stringency conditions are exemplified by conditions under which nucleic acids having intermediate complementarity, about 50-84% complementarity, as well as those having a high degree of complementarity, hybridize. In contrast, low stringency hybridization conditions are those in which nucleic acids having a low degree of complementarity hybridize.

The terms "specific hybridization" and "specifically hybridizes" refer to hybridization of a particular nucleic acid to a target nucleic acid without substantial hybridization to nucleic acids other than the target nucleic acid in a sample.

Stringency of hybridization and washing conditions depends on several factors, including the Tm of the probe and target and ionic strength of the hybridization and wash conditions, as is well-known to the skilled artisan. Hybridization and conditions to achieve a desired hybridization stringency are described, for example, in Sambrook et al., Molecular Cloning: A Laboratory Manual, Cold Spring Harbor Laboratory Press, 2001; and Ausubel, F. et al., (Eds.), Short Protocols in Molecular Biology, Wiley, 2002.

Nucleic acids encoding VH or VL regions and the encoded proteins described herein may be generated recombinantly, such as by expression using an expression construct. Such nucleic acids and proteins may also be chemically synthesized by well-known methods.

The term "expression construct" is used to refer to a double-stranded recombinant nucleotide sequence containing a desired coding sequence and containing one or more regulatory elements necessary or desirable for the expression of the operably-linked coding sequence. The term "regulatory element" as used herein refers to a nucleotide sequence that controls some aspect of the expression of nucleotide sequences. Exemplary regulatory elements illustratively include an enhancer, a TATA box, an internal ribosome entry site (IRES), an intron, an origin of replication, a polyadenylation signal (pA), a promoter, a transcription termination sequence, and an upstream regulatory domain, which contribute to the replication, transcription, and posttranscriptional processing of a nucleotide sequence. Those of ordinary skill in the art are capable of selecting and using these and other regulatory elements in an expression construct with no more than routine experimentation. Expression constructs may be generated recombinantly or synthetically using well-known methodology.

The term "operably-linked" as used herein refers to a nucleotide sequence in a functional relationship with a second nucleotide sequence.

A regulatory element included in an expression cassette may be a promoter. The term "promoter" as used herein refers to a regulatory nucleotide sequence operably-linked to a coding nucleotide sequence to be transcribed such as a nucleotide sequence encoding a desired sequence of amino acids. A promoter is generally positioned upstream of a nucleotide sequence to be transcribed and provides a site for specific-binding by RNA polymerase and other transcription factors. A promoter may be a constitutive promoter or an inducible promoter. A promoter may provide ubiquitous, tissue-specific, or cell-type specific expression.

In addition to a promoter, one or more enhancer sequences may be included such as, but not limited to, the cytomegalovirus (CMV) early enhancer element and the SV40 enhancer element.

Additional included sequences include an intron sequence, a transcription termination sequence, and an mRNA polyadenylation (pA) sequence such as, but not limited to SV40-pA, beta-globin-pA, and AAT-pA.

An expression construct may include sequences necessary for amplification in bacterial cells, such as a selection marker (e.g., a kanamycin or ampicillin resistance gene) and an origin of replication.

Methods of detection of HcTnT-N69 and/or HcTnT-neo in a biological sample according to aspects of the present invention include contacting a sample containing or suspected of containing HcTnT-N69 and/or HcTnT-neo under antigen/antibody binding conditions with a detectably labeled anti-HcTnT-N69 and/or anti-HcTnT-neo antibody, or HcTnT-N69 or HcTnT-neo or intact HcTnT (in a competitive assay format), wherein the detectable label is directly or indirectly attached to the anti-HcTnT-N69 and/or anti-HcTnT-neo antibody. If present, the HcTnT-N69 and/or HcTnT-neo binds to the detectably labeled anti-HcTnT-N69 and/or anti-HcTnT-neo antibody, respectively, to form a complex such that specific detection of the complex is indicative of the specified analyte in the sample.

The term "detectable label" refers to any atom or moiety that can provide a detectable signal and which can be attached to a binding agent, such as a primary or secondary antibody or antigen binding fragment, or analyte, such as HcTnT-N69 or HcTnT-neo. Examples of such detectable labels include fluorescent moieties, chemiluminescent moieties, bioluminescent moieties, ligands, particles, latex particles, luminescent particles, magnetic particles, fluorescent particles, colloidal gold, enzymes, enzyme substrates, radioactive and non-radioactive isotopes and chromophores. Such particles can be of any shape, size, composition, or physiochemical characteristics compatible with assay conditions. The particles can be microparticles having a diameter of less than one millimeter, for example, a size ranging from about 0.1 to about 1,000 micrometers in diameter, inclusive, such as about 3-25 microns in diameter, inclusive, or about 5-10 microns in diameter, inclusive. The particles can be nanoparticles having a diameter from about 1 nanometer (nm) to about 100,000 nm in diameter, inclusive, for example, a size ranging from about 10-1,000 nm, inclusive, or for example, a size ranging from 200-500 nm, inclusive.

Any appropriate method, including but not limited to spectroscopic, optical, photochemical, biochemical, enzymatic, electrical, magnetic, radioactive, isotopic and/or immunochemical is used to detect a detectable label in an assay described herein.

According to aspects of the present disclosure, a detectably labeled antibody or antigen binding fragment characterized by specific binding to HcTnT-69 or a variant thereof, or HcTnT-neo or variant thereof, is an imaging agent which can be used in diagnostic or other clinical assessment procedures. Imaging can be performed by many procedures well-known to those having ordinary skill in the art, for example, by positron emission tomography (PET), single photon emission computed tomography (SPECT), optical fluorescent and luminescent agents and magnetic resonance imaging (MM). In embodiments, the detectable label is a radionuclide tracer is chosen from $^{11}$C, $^{13}$N, $^{15}$O, $^{18}$F, $^{64}$Cu, $^{68}$Ga, $^{76}$Br, $^{82}$Rb, $^{86}$Y, $^{89}$Zr, $^{99}$mTc, $^{111}$In, $^{124}$I, $^{131}$I, $^{186}$Re, $^{43}$K, $^{52}$Fe, $^{57}$Co, $^{67}$Cu, $^{67}$Ga, $^{77}$Br, $^{81}$Rb, $^{81}$mKr, $^{87}$mSr, $^{113}$mIn, $^{123}$I, $^{125}$I, $^{127}$Cs, $^{129}$Cs, $^{132}$I, $^{197}$Hg, $^{203}$Pb and $^{206}$Bi or combination of any two or more thereof.

Immunoassays are well-known in the art and include, but are not limited to, enzyme-linked immunosorbent assay (ELISA) such as but not limited to, antigen capture ELISA, indirect ELISA, fixed cell ELISA; immunochromatography; antigen capture; flow cytometry; immunoblot; immunoprecipitation; immunodiffusion; competitive immunoassays, immunocytochemistry; radioimmunoassay; surface plasmon resonance immunoassay; and combinations of any of these. Generalized details of immunoassays are described in standard references, illustratively including Wild, D., The Immunoassay Handbook, 3rd Ed., Elsevier Science, 2005; Gosling, J. P., Imunoassays: A Practical Approach, Practical Approach Series, Oxford University Press, 2005; E. Harlow and D. Lane, Antibodies: A Laboratory Manual, Cold Spring Harbor Laboratory Press, 1988; F. Breitling and S. Dübel, Recombinant Antibodies, John Wiley & Sons, New York, 1999; H. Zola, Monoclonal Antibodies: Preparation and Use of Monoclonal Antibodies and Engineered Antibody Derivatives, Basics: From Background to Bench, BIOS Scientific Publishers, 2000; B. K. C. Lo, Antibody Engineering: Methods and Protocols, Methods in Molecular Biology, Humana Press, 2003; F. M. Ausubel et al., Eds., Short Protocols in Molecular Biology, Current Protocols, Wiley, 2002; Ormerod, M. G., Flow Cytometry: a practical approach, Oxford University Press, 2000; and Givan, A. L., Flow Cytometry: first principles, Wiley, New York, 2001.

Immunoassay according to aspects of the present invention may include contacting an anti-HcTnT-N69 antibody or antigen binding fragment thereof with a biological sample, wherein the anti-HcTnT-N69 antibody or antigen binding fragment thereof, is immobilized on a solid support to detect binding of the anti-HcTnT-N69 antibody or antigen binding fragment thereof with HcTnT-N69 in the biological sample.

Immunoassay according to aspects of the present invention may include contacting an anti-HcTnT-neo antibody or antigen binding fragment thereof with a biological sample, wherein the anti-HcTnT-neo antibody or antigen binding fragment thereof, is immobilized on a solid support to detect binding of the anti-HcTnT-neo antibody or antigen binding fragment thereof with HcTnT-neo in the biological sample.

Optionally an immunoassay according to aspects of the present invention is performed using a competitive immunoassay format including immobilization of HcTnT-N69, HcTnT-neo and/or intact cTnT.

Optionally, an immunoassay according to aspects of the present invention includes administration of one or more detectably labeled antibodies or antigen binding fragments characterized by specific binding to HcTnT-69 or a variant thereof, or HcTnT-neo or variant thereof, to a living human.

Methods for detecting a cardiac disorder in a human subject having or suspected of having a cardiac disorder which include administering one or more detectably labeled antibodies or antigen binding fragments characterized by specific binding to HcTnT-69 or a variant thereof, or HcTnT-neo or variant thereof; performing an imaging technique to detect the detectable label indicative of specific binding of the one or more detectably labeled antibodies or antigen binding fragments in the human subject, wherein detection of HcTnT-neo or variant thereof in the biological sample is indicative of a cardiac disorder in the human subject.

Methods for detecting a cardiac disorder in a human subject having or suspected of having a cardiac disorder which include administering one or more detectably labeled antibodies or antigen binding fragments characterized by specific binding to HcTnT-69 or a variant thereof, or HcTnT-neo or variant thereof; performing an imaging technique to detect the detectable label indicative of specific binding of the one or more detectably labeled antibodies or antigen binding fragments in the human subject, wherein detection of HcTnT-neo or variant thereof in the biological sample is indicative of cardiac ischemia in the human subject.

The term "solid support" as used herein includes both solid supports and semi-solid supports. The term "solid porous support" as used herein includes both solid porous supports and semi-solid porous supports. The solid support can be in any of various forms or shapes, including planar, such as but not limited to membranes, silicon chips, glass plates and dipsticks; or three dimensional such as but not limited to particles, microtiter plates, microtiter wells, pins and fibers.

A solid support for attachment of an antibody or antigen binding fragment can be any of various materials such as glass; plastic, such as polypropylene, polystyrene, nylon; paper; silicon; nitrocellulose; or any other material to which the antibody, antigen binding fragment or antigen can be attached for use in an assay.

In particular aspects, a solid support to which an antibody, antigen binding fragment, or antigen is attached is a particle which is stable and insoluble under assay conditions. The particles can be of any shape, size, composition, or physiochemical characteristics compatible with assay conditions.

The particle characteristics are optionally chosen so that the particle can be separated from fluid, e.g., on a filter with a particular pore size or by some other physical property, e.g., a magnetic property.

The particles are optionally latex particles, luminescent particles, magnetic particles, or fluorescent particles.

The particles can be of any shape, size, composition, or physiochemical characteristics compatible with assay conditions. The particles can be microparticles having a diameter of less than one millimeter, for example, a size ranging from about 0.1 to about 1,000 micrometers in diameter, inclusive, such as about 3-25 microns in diameter, inclusive, or about 5-10 microns in diameter, inclusive. The particles can be nanoparticles having a diameter from about 1 nanometer (nm) to about 100,000 nm in diameter, inclusive, for example, a size ranging from about 10-1,000 nm, inclusive, or for example, a size ranging from 200-500 nm, inclusive. The particles are can be organic or inorganic particles, such as glass or metal and can be particles of a synthetic or naturally occurring polymer, such as polystyrene, polycarbonate, silicon, nylon, cellulose, agarose, dextran, and polyacrylamide. Particles are latex beads according to aspects of the present invention.

Particles used are optionally encoded and distinguishable from other particles based on a characteristic such as color, reflective index and/or an imprinted or otherwise optically detectable pattern. For example, the particles may be encoded using optical, chemical, physical, or electronic tags. Encoded particles can contain or be attached to, one or more fluorophores which are distinguishable, for instance, by excitation and/or emission wavelength, emission intensity, excited state lifetime or a combination of these or other optical characteristics. Optical bar codes can be used to encode particles.

According to aspects of the present invention, immunoassay includes assay of HcTnT-N69 and/or HcTnT-neo in a biological sample by an ELISA technique.

The biological sample may be diluted or processed to purify or concentrate HcTnT-N69 and/or HcTnT-neo prior to analysis.

Any reaction or diluent buffer compatible with the sample, reagents and reaction can be used, including but not limited to phosphate buffered saline, sodium phosphate buffer, potassium phosphate buffer, Tris-HCl buffer, Tricine buffer and other buffers described herein.

HcTnT-N69 and/or HcTnT-neo contained in a biological sample is optionally purified or concentrated for assay according to a method of the present invention.

The term "purified" in the context of a biological sample refers to separation of HcTnT-N69 and/or HcTnT-neo in the biological sample from at least one other component present in the biological sample.

In particular embodiments, HcTnT-N69 and/or HcTnT-neo is optionally substantially purified from the biological sample to produce a substantially purified sample for use in an inventive assay. The term "substantially purified" refers to a desired material separated from other substances naturally present in a sample obtained from the subject so that the desired material makes up at least about 0.01-100% of the mass, by weight, such as about 0.01%, 0.1%, 1%, 5%, 10%, 25%, 50% 75% or greater than about 75% of the mass, by weight, of the substantially purified sample.

Sample purification is achieved by techniques illustratively including electrophoretic methods such as gel electrophoresis and 2-D gel electrophoresis; chromatography methods such as HPLC, ion exchange chromatography, affinity chromatography, size exclusion chromatography, thin layer and paper chromatography. It is appreciated that electrophoresis and chromatographic methods can also be used to separate a peptide or peptides from other components in a sample in the course of performing an assay, as in, for example separation of proteins in immunoblot assays.

According to one aspect of the present invention, HcTnT-N69 and/or HcTnT-neo is isolated and concentrated by absorption onto a solid substrate.

Conjugates and Compositions

A conjugate composition is provided according to the present invention which includes an antibody or antigen binding fragment thereof characterized by specific binding to HcTnT-N69 or HcTnT-neo, or a variant of either thereof, conjugated to a cargo moiety. Conjugate compositions including such an antibody or antigen binding fragment conjugated to a cargo moiety may be used to deliver a cargo moiety to a target, such as a cell expressing HcTnT and/or where free HcTnT-N69 or HcTnT-neo are present.

A cargo moiety included in a conjugate can be any material desired to be delivered to the target, including, but not limited to, a drug, a contrast agent, or a nucleic acid.

A drug or contrast agent included as a cargo moiety is not limited as to the identity of the drug or contrast agent.

Optionally, the cargo moiety is a nucleic acid. A delivered nucleic acid may be any of various nucleic acids, such as, but not limited to, an expression vector, such as a bacterial plasmid or a viral expression vector. A nucleic acid cargo is optionally an antisense construct such as an antisense oligonucleotide, an siRNA, an shRNA or an expression vector for expressing an antisense nucleic acid.

A cargo moiety is conjugated to an antibody or antigen binding fragment thereof characterized by specific binding to HcTnT-N69 or HcTnT-neo, or a variant of either thereof by any of various methods. The conjugation method chosen will depend on the chemical identity of the cargo and the antibody or antigen binding fragment.

A conjugate according to embodiments of the present invention encompasses an antibody or antigen binding fragment and a cargo linked together by chemical bonding, covalent or non-covalent, as well as by recombinant techniques including production of a fusion protein, such as a conjugate produced using a nucleic acid expression construct encoding the antibody or antigen binding fragment and a cargo.

In particular embodiments, a cargo moiety and an antibody or antigen binding fragment are chemically linked via free functional groups on these moieties. Such functional groups illustratively include amino, carboxyl, hydroxyl, and sulfhydryl groups.

A linkage between a cargo moiety and an antibody or antigen binding fragment is illustratively an ester, an ether, a carbamate, a carbonate, a disulfide, a peptide, and an amide. The term "linkage" refers to a bond or group formed by chemical reaction between the two moieties such that the moieties are covalently coupled, directly or indirectly.

In one embodiment, a linkage between an antibody or antigen binding fragment and a cargo moiety is labile in an intracellular environment, such that the an antibody or antigen binding fragment and cargo moiety may be separated following cell uptake. For instance, a linkage may be susceptible to hydrolysis, enzymatic cleavage, or other form of cleavage, such that the cargo moiety provides a desired effect following such separation from the antibody or antigen binding fragment. An ester linkage is one example of a linkage susceptible to hydrolysis in a cell. A disulfide linkage is a further example of a linkage susceptible to cleavage following cell uptake. In other embodiments, a cargo moiety provides a desired effect while conjugated to the antibody or antigen binding fragment.

In one embodiment, more than one cargo moiety may be included in a conjugate composition. Further, more than one antibody or antigen binding fragment may be included in a conjugate composition.

A protective group may be added to an antibody or antigen binding fragment and/or cargo moiety in a process to form a conjugate according to the present invention. Such groups, their generation and use are described in Protective Groups in Organic Synthesis by T. W. Greene and P. G. M. Wuts, John Wiley & Sons, 1999.

Conjugation chemistries used in conjugation of a cargo moiety and an antibody or antigen binding fragment illustratively include coupling agents such as glutaraldehyde, carbodiimide, succinimde esters, benzidine, periodate, isothionate and combinations of these.

A conjugate according to the present invention is optionally produced using recombinant techniques. For example, in particular embodiments, a conjugate is an expression product of a nucleic acid construct including an expression construct encoding a fusion protein, the fusion protein including an antibody or antigen binding fragment or portion thereof and a cargo moiety linked directly to the antibody or antigen binding fragment or portion thereof or through an intermediate linker.

An antibody or antigen binding fragment and/or an antibody or antigen binding fragment conjugate of the present invention can be administered to a subject alone or as part of a pharmaceutical composition. Inventive compositions are suitable for administration to patients by a variety of routes illustratively including intravenous, oral, parenteral, intramuscular, subcutaneous and mucosal.

An antibody or antigen binding fragment and/or an antibody or antigen binding fragment conjugate of the present invention optionally includes a pharmaceutically acceptable carrier. The term "pharmaceutically acceptable" refers to a material which can be administered to a subject along with an inventive antibody or antigen binding fragment and/or an antibody or antigen binding fragment conjugate composition without causing significant undesirable biological effects and without interacting in a deleterious manner with any other component of the pharmaceutical composition.

Pharmaceutical compositions suitable for administration illustratively include physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers; diluents; solvents; or vehicles include water, ethanol, polyols such as propylene glycol, polyethylene glycol, glycerol, and the like, suitable mixtures thereof; vegetable oils such as olive oil; and injectable organic esters such as ethyloleate. Proper fluidity can be maintained, for example, by the use of a coating such as lecithin, by the maintenance of the required particle size in the case of dispersions, and by the use of surfactants.

Compositions suitable for injection optionally include physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

Pharmaceutical compositions according to the present invention may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and the like. Prolonged absorption of an injectable pharmaceutical form can be brought about by the use of agents delaying absorption, for example, aluminum monostearate and gelatin.

Further exemplary adjuvants include immunostimulating adjuvants such as Freund's complete adjuvant; Freund's incomplete adjuvant; aluminum hydroxide such as commercially available as Alhydrogel, Accurate Chemical & Scientific Co, Westbury, N.Y.; and Gerbu adjuvant, available from C-C Biotech, Poway, Calif.

Solid dosage forms for oral administration include capsules, tablets, pills, powders, and granules. In such solid dosage forms, an inventive conjugate is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Microencapsulated formulations of an inventive antibody or antigen binding fragment and/or an antibody or antigen binding fragment conjugate are also contemplated.

Liquid dosage forms for oral administration include pharmaceutically acceptable emulsions, solutions, suspensions, syrups, and elixirs. In addition to a conjugate according to the present invention, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, a pharmaceutical composition according to the present invention can also include adjuvants, such as wetting agents, emulsifying and suspending agents, sweetening, flavoring, and perfuming agents.

Suspensions, in addition to an inventive conjugate, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Further specific details of pharmaceutical formulation can be found in Pharmaceutical Dosage Forms: Tablets, eds. H. A. Lieberman et al., New York: Marcel Dekker, Inc., 1989; L. V. Allen, Jr. et al., Ansel's Pharmaceutical Dosage Forms and Drug Delivery Systems, 8th Ed., Philadelphia, Pa., Lippincott, Williams & Wilkins, 2004; and Remington, The Science and Practice of Pharmacy, $21^{st}$ ed., Lippincott, Williams & Wilkins, Philadelphia, Pa., 2006.

An inventive antibody or antigen binding fragment and/or an antibody or antigen binding fragment conjugate is optionally delivered in conjunction with a non-conjugated therapeutic and/or diagnostic agent in one embodiment. A therapeutic and/or diagnostic agent suitable in this regard illustratively includes an analgesic, an antibiotic, an antibody, an antigen, an anti-inflammatory, an anti-tumoral agent, an antiviral, a gamma or beta radiation emitting species, an enzyme, and a hormone. In addition, two or more compositions may be administered to a subject.

The dosage of an inventive pharmaceutical composition will vary based on factors such as the route of administration; the age, health, and weight of the subject to whom the composition is to be administered; the nature and extent of the subject's symptoms, if any, and the effect desired. Usually a daily dosage of an inventive antibody or antigen binding fragment and/or an antibody or antigen binding fragment conjugate is in the range of about 0.001 to 100 milligrams per kilogram of a subject's body weight. A daily dose may be administered as two or more divided doses to obtain the desired effect. An inventive pharmaceutical composition may also be formulated for sustained release to obtain desired results.

According to aspects, immunoassay kits for detecting a cardiac condition in a human subject having or suspected of having a cardiac condition are provided which include one or more antibodies or antigen binding fragments characterized by specific binding to HcTnT-N69, HcTnT-neo or a variant of either thereof.

According to aspects, immunoassay kits for detecting a cardiac condition in a human subject having or suspected of having a cardiac condition are provided which include one or more antibodies or antigen binding fragments including a first antibody or antigen binding fragment characterized by specific binding to HcTnT-N69, HcTnT-neo or a variant of either thereof.

Immunoassay kits for detecting a cardiac condition of a human subject having or suspected of having a cardiac condition, are provided according to aspects of the present invention including one or more nucleic acids encoding a VH or VL region of one or more antibodies or antigen binding fragments wherein the one or more antibodies or antigen binding fragments are characterized by specific binding to HcTnT-N69, or a variant thereof.

One or more auxiliary components are optionally included in such kits, such as a control peptide or protein, a secondary antibody, one or more reaction vessels, a buffer, diluent or a reconstituting agent.

Optionally, a kit according to aspects of the present invention includes a detectable label attached to an antibody or antigen binding fragment characterized by specific binding to HcTnT-N69, HcTnT-neo, or a variant of either thereof. In a further option, a kit according to aspects of the present invention includes a detectable label to be attached to an antibody or antigen binding fragment characterized by specific binding to HcTnT-N69, HcTnT-neo, or a variant of either thereof. In a further option, a kit according to aspects of the present invention includes a detectably labeled secondary reagent, such as a secondary antibody, such as an anti-mouse IgG secondary antibody, which specifically binds to an antibody or antigen binding fragment characterized by specific binding to HcTnT-N69, HcTnT-neo, or a variant of either thereof. In a further option, a kit according to aspects of the present invention includes a detectably labeled secondary reagent, such as a secondary antibody, such as an anti-mouse IgG secondary antibody, which specifically binds to a monoclonal antibody or antigen binding fragment characterized by specific binding to HcTnT-N69 or a variant thereof.

Embodiments of inventive compositions and methods are illustrated in the following examples. These examples are provided for illustrative purposes and are not considered limitations on the scope of inventive compositions and methods.

EXAMPLES

Figure 6:
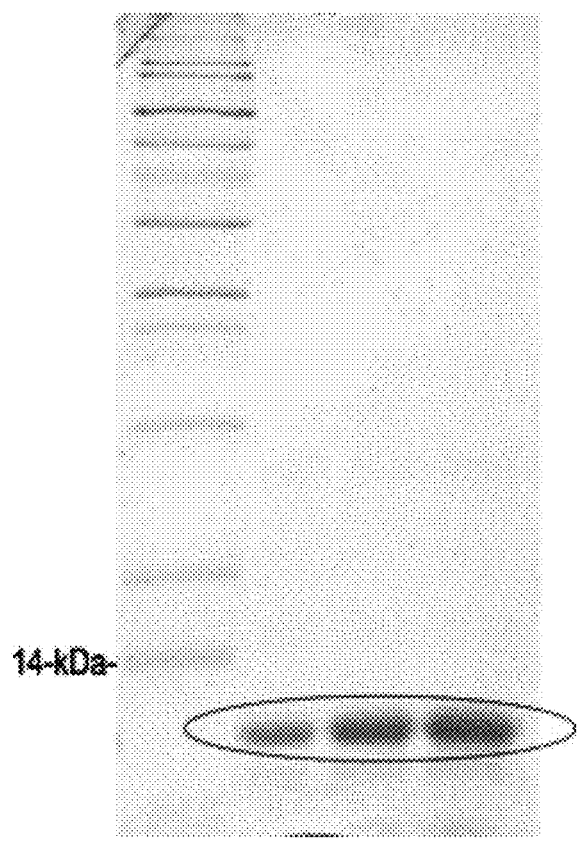
FIG. 6 is an image of an SDS-gel showing recombinantly produced N-terminal cTnT (NT-cTnT). The location of the recombinantly produced NT-cTnT is circled on the gel image. Molecular weight standards are shown in the far-left lane.
Figure 7:
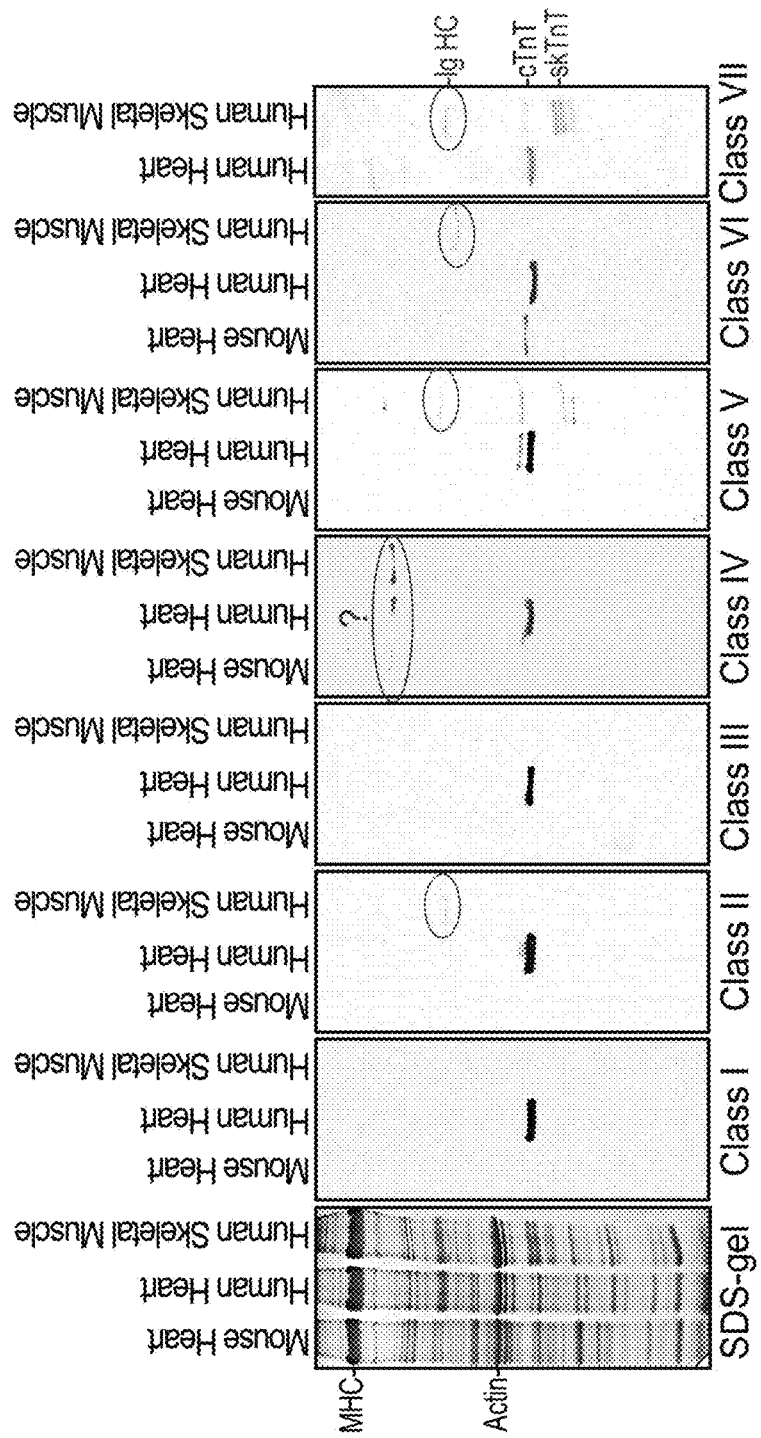
FIG. 7 shows results of Western blotting on total protein extracts from cardiac and skeletal muscle tissues. The representative Western blots shown in FIG. 7 show specificity of monoclonal antibodies classified herein as Classes I, II, III, IV, V, VI and VII. Classes I, II, III, IV and VI are highly specific to cardiac TnT without crossreaction with skeletal muscle TnT. Class VI also recognizes mouse cardiac TnT. Classes V and VII have some minor crossreaction with skeletal muscle TnT. A trace amount of immunoglobulin heavy chain (IgHC) was detected in the human skeletal muscle tissue sample (likely from blood contained in the sample) by the crossreaction of anti-mouse total Ig secondary antibody. An unknown protein band was recognized by Class IV mAb in both mouse and human heart and muscle samples.

HcTnT-N69, SEQ ID NO:1 was recombinantly produced. FIG. 6 is an SDS-gel showing recombinantly produced N-terminal cTnT.

Figure 8:
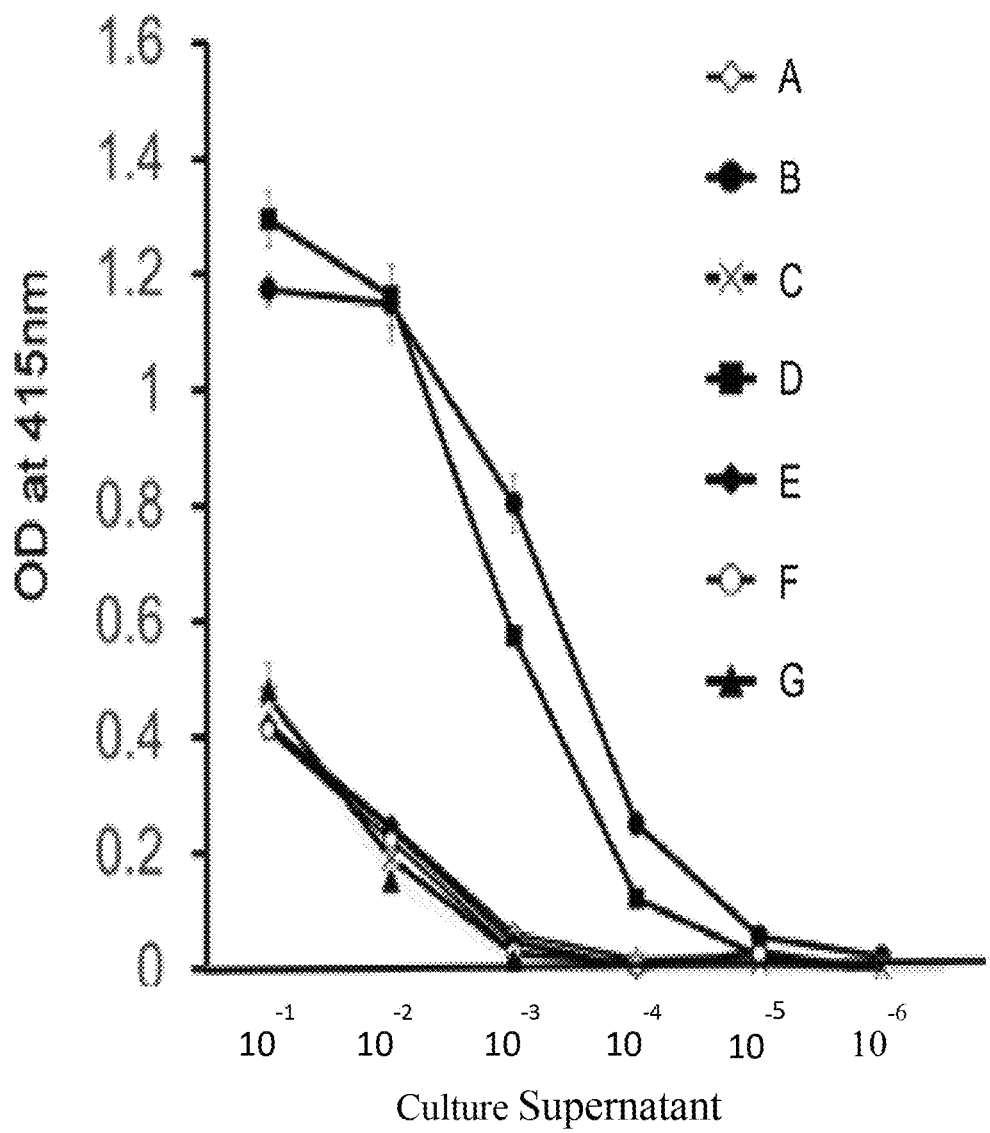
FIG. 8 is a graph showing results of ELISA analysis for seven anti-N69 monoclonal antibodies produced and isolated.
Figure 9A:
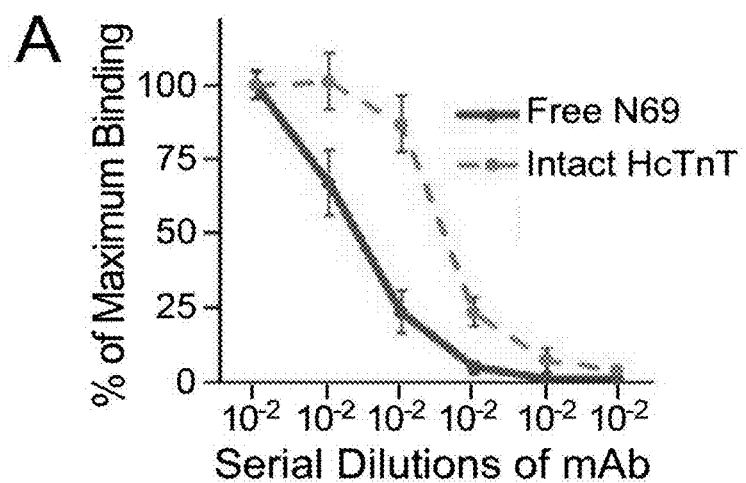
FIG. 9A is a graph representative of monoclonal antibodies of Class I, Class II and Class IV, having higher affinity to the N69 peptide epitope residing in the intact human cardiac troponin T (HcTnT) protein compared to the isolated N69 peptide, although both the N69 peptide and intact HcTnT protein are recognized.
Figure 9B:
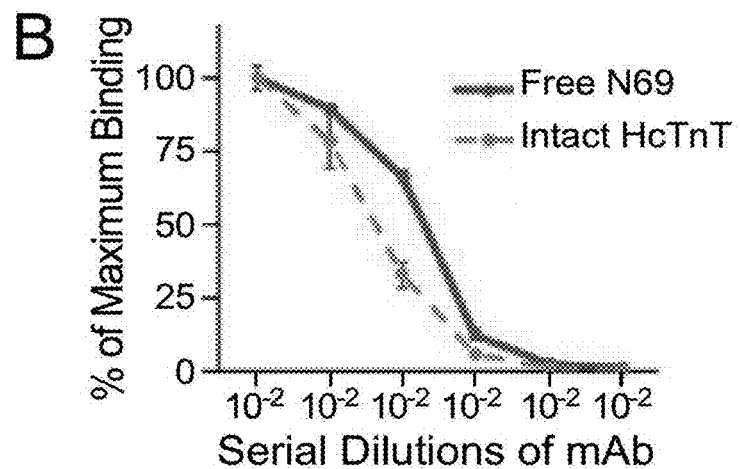
FIG. 9B is a graph representative of monoclonal antibodies of Class III, having higher affinity to the N69 peptide epitope residing in the isolated N69 peptide compared to the N69 peptide epitope residing in the intact HcTnT protein, although both the N69 peptide and intact HcTnT protein are recognized.

Monoclonal Antibody Development:

8-week-old female Balb/c mice were immunized with the antigen, HcTnT-N69, SEQ ID NO:1. Spleen cells were harvested from the immunized mouse to fuse with 5P2/0-Ag14 mouse myeloma cells. Hybridomas were selected by HAT (0.1 mM hypoxanthine, 0.4 μM aminopterin, 16 thymidine) media and screened by indirect ELISA using horseradish peroxidase (HRP)-labeled, goat anti-mouse total immunoglobulin (Sigma) as the second antibody. The anti-cTnT-N69 antibody-secreting hybridomas were subcloned three or more times by limiting dilution to establish stable cell lines. The hybridoma cells were introduced into 2,6,10,14-tetramethyl pentadecane (Pristane, Sigma)-primed peritoneal cavity of Balb/c mice to produce mAb-enriched ascites fluids. Alternatively, the hybridoma cells were cultured in vitro to produce mAb-enriched culture supernatants.

The immunoglobulin subclass of the mAbs was determined by a sandwich ELISA using a mouse immunoglobulin isotyping kit.

Cardiac TnT specificity of the monoclonal antibodies was determined using Western blotting on total protein extracts from cardiac and skeletal muscle tissues. Alkaline phosphatase-labeled anti-mouse IgG antibody was used as the second antibody. FIG. 7 shows results of this analysis.

ELISA Titrations

Purified HcTnT-N69 (also called N69) having the amino acid sequences shown in SEQ ID NO:1 or intact human cTnT antigen was immobilized on microtiter plates. After washing and blocking the plastic surface with 1% BSA and 0.05% Tween-20, the immobilized antigen was incubated with serial dilutions of the anti-N69 mAbs. Following washes to remove the unbound antibody, the plates were further incubated with HRP-conjugated second antibody followed by washes and $H_2O_2$-ABTS substrate reaction. $A_{415nm}$ curve for each assay well was recorded by an automated microplate reader. FIG. 8 shows the results of this analysis.

Determination of the Sequence of mRNA encoding anti-N69 mAbs

RNA Isolation
1. Collect hybridoma cells (~1×10⁶) into 15 ml tube, spin 5 min at 300×g to remove media
2. Re-suspend and transfer cells to 1.5 ml centrifuge tubes in 1 ml ice cold PBS and pellet cells by spinning at 300×g for 5 min
3. Frozen the cell pellet immediately in liquid nitrogen and store at −80° C.
4. Using Trizol reagent to extract cellular RNA per the manufacturer's instruction
5. Dissolve the yield RNA in 20 ul DEPC-treated water and incubate at 55-60° C. for 10 min
6. Run 1 ul of the RNA solution on agarose gel to check quality and estimate concentration Reverse Transcription
1. Use 1 ug RNA to incubate with 20 pmole of an anchored oligo dT primer (TV 20) at 70° C. for 5 min
2. Cool at room temperature for 10 min and on ice for 5 min
3. Add AMV reverse transcriptase, reaction buffer and dNTP for 35 ul reaction of reverse transcription of cDNA 42° C. for 2 hrs
4. Store the RT product at −80° C.

PCR of cDNA Encoding Ig HV and LV Regions
1. PCR primers are designed as described in Wang et al. J. Immunol. Methods 233:167-77, 2000.
2. 2 ul of the RT products are used in 25 ul PCR reaction using high fidelity thermostable DNA polymerase.
3. 3 ul of the PCR product of each reaction was examined on agarose gel Sequence Analysis
1. 10 ul of each PCR product was sent to a commercial facility for direct DNA sequencing using both of the PCR primers
2. Ig VH and VL cDNA and predicted protein sequences were analyzed using a computer software Assay Example 1

The detection of HcTnT-N69 in patient samples may be carried out as in an assay similar to the following examples:
N69 peptide (HcTnT-N69) or N69-containing HcTnT protein, or a derivative of either, is immobilized on a solid phase. A human patient sample is mixed with a predetermined concentration of anti-N69 mAb of the present invention (labeled or unlabeled) and these are incubated together, followed by washing to remove unbound materials. The bound anti-N69 mAb is detected via direct labeling or via a labeled secondary antibody. The presence and concentration of N69 in the sample will be quantified by the degree of decrease of the bound anti-N69 mAb.

Assay Example 2

An anti-N69 Ab of the present invention is immobilized on a solid phase. A human patient sample solution is applied to the solid phase and the changes in optical signals are monitored, such as by use of surface plasmon resonance (SPR).

| SEQUENCES |
|---|
| Human cTnT N69 amino acid sequence SEQ ID NO: 1<br>MSDLEEVVVEEYEEEEQEEAAVEVQEEAAEEDAEAEAETEETRAEEDEEEEAKEAEDGPMEES<br>KPKPR (SEQ ID NO: 1) |
| SEQ ID NO: 2 - Amino acid sequence of variable heavy chain region of mAb 1D6<br>GPELVKPGASVKISCKTSGYTFTENTIHWVKQSHGKSLEWVGGINPNNGGTNYNQKFK<br>GRAALTVDKSSSTAYMELRSLTSEDSAVYYCARSWDWFAYWGQGTLVTVSA<br>(SEQ ID NO: 2) |
| SEQ ID NO: 3 - Amino acid sequence of variable heavy chain region of mAb 1D6<br>LSLPVSLGDQASISCRSSQSLVHSNGNTYLHWYLQKPGQSPKLLVYKVSNRFSGVPDRFS<br>GSGSGTDFTLKIIRVEAEDLGVYFCSQSTRIPFTFGSGTKLEMKRA (SEQ ID NO: 3) |
| SEQ ID NO: 4 - nucleotide sequence encoding variable heavy chain region of mAb 1D6<br>GGACCTGAACTGGTGAAGCCTGGGGCTTCAGTGAAGATTTCCTGTAAGACTTCTGGA<br>TACACATTCACTGAAAACACCATACACTGGGTGAAGCAGAGCCATGGAAAGAGCCT<br>TGAGTGGGTTGGAGGTATCAATCCTAACAATGGTGGCACTAATTACAATCAGAAATT<br>TAAGGGCAGGGCCGCATTGACTGTAGACAAGTCCTCCAGCACAGCCTACATGGAGC<br>TCCGCAGCCTGACATCTGAAGATTCTGCAGTCTATTATTGTGCAAGATCCTGGGACT<br>GGTTTGCTTACTGGGGCCAAGGGACTCTGGTCACTGTCTCTGCA (SEQ ID NO: 4) |
| SEQ ID NO: 5 - nucleotide sequence encoding variable light chain region of mAb 1D6<br>CTCTCCCTGCCTGTCAGTCTTGGAGATCAGGCCTCCATCTCTTGCAGATCTAGTCAGA<br>GCCTTGTACACAGTAATGGAAACACCTATTTACATTGGTACCTGCAGAAGCCAGGCC<br>AGTCTCCAAAGCTCCTGGTCTACAAAGTTTCCAACCGATTTTCTGGGGTCCCAGACA<br>GGTTCAGTGGCAGTGGATCAGGGACAGATTTCACACTCAAGATCATCAGAGTGGAG<br>GCTGAGGATCTGGGAGTTTATTTCTGCTCTCAAAGTACACGTATTCCATTCACGTTCG<br>GCTCGGGGACAAAGTTGGAAATGAAACGGGCT (SEQ ID NO: 5) |
| SEQ ID NO: 6 - Amino acid sequence of variable light chain region of mAb 2D11<br>LSLPVSLGDQASISCRSSQSLVHSNGNTYLHWYLQKPGQSPKLLVYKVSNRFSGVPDRFS<br>GSGSGTDFTLKIIRVKAEDLGVYFCSQSTRIPFTFGSGTKLEMKRA (SEQ ID NO: 6) |

SEQ ID NO: 7 - nucleotide sequence encoding variable light chain region of mAb
2D11
CTCTCCCTGCCTGTCAGTCTTGGAGATCAGGCCTCCATCTCTTGCAGATCTAGTCAGA
GCCTTGTACACAGTAATGGAAACACCTATTTACATTGGTACCTGCAGAAGCCAGGCC
AGTCTCCAAAGCTCCTGGTCTACAAAGTTTCCAACCGATTTTCTGGGGTCCCAGACA
GGTTCAGTGGCAGTGGATCAGGGACAGATTTCACACTCAAGATCATCAGAGTGAAG
GCTGAGGATCTGGGAGTTTATTTCTGCTCTCAAAGTACACGTATTCCATTCACGTTCG
GCTCGGGGACAAAGTTGGAAATGAAACGGGCT (SEQ ID NO: 7)

SEQ ID NO: 8 - Amino acid sequence of variable heavy chain region of mAb 1E11
GAELAKPGASVKMSCKASGYTFTTYWMHWVKQRPGQGLEWIGFINPSTGYTEYNQKF
KDKATLTADKSSSTAYMQLSSLTSGDSAVYYCARKSFAYWGHGTLVTVSAATTTA
(SEQ ID NO: 8)

SEQ ID NO: 9 - Amino acid sequence of variable light chain region of mAb 1E11
LTLSVTIGQPASISCKSSQSLLHSDGKTYLNWLLQRPGQSPKRLIYLVSKLDSGVPDRFTG
SGSGTDFTLKISRVEAEDVGIYYCWQGTQFPRTFGGGTKLEIKRA (SEQ ID NO: 9)

SEQ ID NO: 10 - nucleotide sequence encoding variable heavy chain region of mAb
1E11
GGGGCTGAACTGGCAAAACCTGGGGCCTCAGTGAAGATGTCCTGCAAGGCTTCTGG
TTACACCTTTACTACTTACTGGATGCACTGGGTAAAACAGAGGCCTGGACAGGGTCT
GGAATGGATTGGATTCATTAATCCTAGTACTGGTTATACTGAATACAATCAGAAGTT
CAAGGACAAGGCCACATTGACTGCAGACAAATCCTCCAGCACAGCCTACATGCAAC
TGAGCAGCCTGACATCTGGGGACTCTGCAGTCTATTACTGTGCAAGAAAGAGTTTTG
CTTACTGGGGCCACGGGACTCTGGTCACTGTCTCTGCAGCTACAACAACAGCC
(SEQ ID NO: 10)

SEQ ID NO: 11 - nucleotide sequence encoding variable light chain region of mAb
1E11
CTCACTTTGTCGGTTACCATTGGACAACCAGCCTCCATCTCTTGCAAGTCAAGTCAG
AGCCTCTTACATAGTGATGGAAAGACATATTTGAATTGGTTGTTACAGAGGCCAGGC
CAGTCTCCAAAGCGCCTAATCTATCTGGTGTCTAAACTGGACTCTGGAGTCCCTGAC
AGGTTCACTGGCAGTGGATCAGGGACAGATTTCACACTGAAAATCAGCAGAGTGGA
GGCTGAGGATGTGGGAATTTATTATTGCTGGCAAGGTACACAATTTCCTCGGACGTT
CGGTGGAGGCACCAAGCTGGAAATCAAACGGGCT (SEQ ID NO: 11)

SEQ ID NO: 12 - Amino acid sequence of variable heavy chain region of mAb 3H5
GGGLVQPKGSLKLSCAASGFTFNTYAMNWVRQAPGKGLEWVARIRSKSNNYATYYAD
SVKDRFTISRDDSQSMLYLQMNNLKTEDTAMYYCVRHDGVAWFAYWGQGTLVTVSA
(SEQ ID NO: 12)

SEQ ID NO: 13 - Amino acid sequence of variable light chain region of mAb 3H5
LSLPVSLGDQASISCRSSQSIVHSNGNTYLEWYLQKPGQSPKLLIYKVSNRFSGVPDRFSG
SGSGTDFTLKISRVEAEDLGVYYCFQGSHVPPTFGAGTKLELKRA (SEQ ID NO: 13)

SEQ ID NO: 14 - nucleotide sequence encoding variable heavy chain region of mAb
3H5
GGTGGAGGATTGGTGCAGCCTAAAGGGTCATTGAAACTCTCATGTGCAGCCTCTGGA
TTCACCTTCAATACCTACGCCATGAACTGGGTCCGCCAGGCTCCAGGAAAGGGTTTG
GAATGGGTTGCTCGCATAAGAAGTAAAAGTAATAATTATGCAACATATTATGCCGAT
TCAGTGAAAGACAGGTTCACCATCTCCAGAGATGATTCACAAAGCATGCTCTATCTG
CAAATGAACAACTTGAAAACTGAGGACACAGCCATGTATTACTGTGTGAGACATGA
TGGTGTCGCCTGGTTTGCTTACTGGGGCCAAGGGACTCTGGTCACTGTCTCTGCA
(SEQ ID NO: 14)

SEQ ID NO: 15 - nucleotide sequence encoding variable light chain region of mAb
3H5
CTCTCCCTGCCTGTCAGTCTTGGAGATCAAGCCTCCATCTCTTGCAGATCTAGTCAGA
GCATTGTACATAGTAATGGAAACACCTATTTAGAATGGTACCTGCAGAAACCAGGC
CAGTCTCCAAAGCTCCTGATCTACAAAGTTTCCAACCGATTTTCTGGGGTCCCAGAC
AGGTTCAGTGGCAGTGGATCAGGGACAGATTTCACACTCAAGATCAGCAGAGTGGA
GGCTGAGGATCTGGGAGTTTATTACTGCTTTCAAGGTTCACATGTTCCTCCCACGTTC
GGTGCTGGGACCAAGCTGGAGCTGAAACGGGCT (SEQ ID NO: 15)

SEQ ID NO: 16 - Amino acid sequence of variable light chain region of mAb 2H3
LSLPVSLGDQASISCRSSQSIVHSNGNTYLEWYLQKPGQSPKLLIYKVSNRFSGVPDRFSG
SGSGTDFTLKISRVKAEDLGVYYCFQGSHVPPTFGAGTKLELKRA (SEQ ID NO: 16)

SEQ ID NO: 17 - nucleotide sequence encoding variable light chain region of mAb
2H3
CTCTCCCTGCCTGTCAGTCTTGGAGATCAAGCCTCCATCTCTTGCAGATCTAGTCAGA
GCATTGTACATAGTAATGGAAACACCTATTTAGAATGGTACCTGCAGAAACCAGGC -continued

SEQUENCES

CAGTCTCCAAAGCTCCTGATCTACAAAGTTTCCAACCGATTTTCTGGGGTCCCAGAC
AGGTTCAGTGGCAGTGGATCAGGGACAGATTTCACACTCAAGATCAGCAGAGTGAA
GGCTGAGGATCTGGGAGTTTATTACTGCTTTCAAGGTTCACATGTTCCTCCCACGTTC
GGTGCTGGGACCAAGCTGGAGCTGAAACGGGCT (SEQ ID NO: 17)

SEQ ID NO: 18 - Amino acid sequence of variable light chain region of mAb 4F5
LSLPVSLGDQASISCKSSQSIVHSNGNTYLEWYLQKPGQSPKLLIYKVSNRFSGVPDRFSG
SGSGTDFTLKISRVKAEDLGVYYCFQGSHVPPTFGAGTKLELKRA (SEQ ID NO: 18)

SEQ ID NO: 19 - nucleotide sequence encoding variable light chain region of mAb 4F5
CTCTCCCTGCCTGTCAGTCTTGGAGATCAAGCCTCCATCTCTTGCAGATCT
AGTCAGAGCATTGTACATAGTAATGGAAACACCTATTTAGAATGGTACCTGCAGAA
ACCAGGCCAGTCTCCAAAGCTCCTGATCTACAAAGTTTCCAACCGATTTTCTGGGGT
CCCAGACAGGTTCAGTGGCAGTGGATCAGGGACAGATTTCACACTCAAGATCAGCA
GAGTGAAGGCTGAGGATCTGGGAGTTTATTACTGCTTTCAAGGTTCACATGTTCCTC
CCACGTTCGGTGCTGGGACCAAGCTGGAGCTGAAACGGGCT (SEQ ID NO: 19)

SEQ ID NO: 20 - Amino acid sequence of variable light chain region of mAb 2D9
LSLPVSLGDQASISCKSSQSIVHSNGNTYLKWYLQKPGQSPKLLIYKVSNRFSGVPDRFS
GSGSGTDFTLKISRVKAEDLGVYYCFQGSHVPPTFGAGTKLELKRA (SEQ ID NO: 20)

SEQ ID NO: 21 - nucleotide sequence encoding variable light chain region of mAb 2D9
CTCTCCCTGCCTGTCAGTCTTGGAGATCAAGCCTCCATCTCTTGCAGATCTAGTCAGA
GCATTGTACATAGTAATGGAAACACCTATTTAAAATGGTACCTGCAGAAACCAGGC
CAGTCTCCAAAGCTCCTGATCTACAAAGTTTCCAACCGATTTTCTGGGGTCCCAGAC
AGGTTCAGTGGCAGTGGATCAGGGACAGATTTCACACTCAAGATCAGCAGAGTGAA
GGCTGAGGATCTGGGAGTTTATTACTGCTTTCAAGGTTCACATGTTCCTCCCACGTTC
GGTGCTGGGACCAAGCTGGAGCTGAAACGGGCT (SEQ ID NO: 21)

SEQ ID NO: 22: human fast skeletal muscle troponin T (HfTnT-N42)
MSDEEVEQVEEQYEEEEEAQEEEVQEDTAEEDAEEEKPRPK SEQ ID NO: 23: human slow skeletal muscle troponin T (HsTnT-N43)
MSDTEEQEYEEEQPEEEAAEEEEEAPEEPEPVAEPEEERPKPS SEQ ID NO: 24: consensus sequence obtained by comparison of HcTnT-N69, HfTnT-N42, and HsTnT-N43.

$MSDX_1EEVEEYEEEX_2X_3EEEX_4AEEEEEX_5EEX_6X_7AEEDX_8EEEKPKPX_9$, where $X_1$ is L or T; $X_2$ is E or Y or Q; $X_3$ is Q or E or P; $X_4$ is D or E or A; $X_5$ is T or V or A; $X_6$ is T or D or P; $X_7$ is R or T or E; $X_8$ is E or A or P; and $X_9$ is R or K or S.

SEQ ID NO: 25: An unrelated IgG1 VH amino acid sequence (accession #S59138.1)
GAELVRPGTSVKVSCKAFGYAFSNYLIEWVQQRHGQGLEGIGVMIYPGSGDHKYNEKF
KGKATLTADKSSSTAYMQLSSLTSDDSAVYFCARFDYDVTYAMAYWGQGTSATV SEQ ID NO: 26: An unrelated IgG3 VH amino acid sequence (accession #DQ273284.1)
GGGLVQPGGSMKLSCVASEFTFNNYWMNWVRQSPEKGLEWVAEIRLKSNNYATHYAE
SVKGRFTISRDDSKSSVYLQMNNLRAEDTGIYYCTSNVAMDYWGQGTTVTVSS SEQ ID NO: 27: An unrelated IgM VH amino acid sequence (accession #M77137.1)
GLVAPSQSLSITCTVSGFSLTSYGVHWVRQPPGKGLEWLGVIWAGGSTNYNSALMSRLS
ISKGDNSKSQVFLKMNSLQTDDTAMYYCARCYYGSHFDYWGQGTTLTVSS SEQ ID NO: 28 An unrelated kappa VL amino acid sequence (accession #Z22039.1)
SSLAVSAGEKVTMSCKSSQSLLNSRTRKNYLAWYQQKPGQSPKLLIYWASSRESGVPDR
FTGSGSGTDFTLTISSVQAEDLAVYYCKQSYNLYTFGGGTKLEIK SEQ ID NO: 29 Anti-N69 mAb kappa VL Consensus sequence
LSLPVSLGDQASISCKSSQSIVHSNGNTYLEWYLQRPGQSPKLLIYKVSNRFSGVPDRFSG
SGSGTDFTLKISRVKAEDLGVYYCFQGSHVPPTFGAGTKLELK SEQ ID NO: 30 Anti-N69 VL Consensus sequence
$LX_1LX_2VX_1X_3GX_4X_5ASISCKSSQSX_3X_6HSX_7GX_8TYLX_9WX_{10}LQRPGQSPKX_{11}LX_{12}YX_{13}V$
$SX_8X_{11}X_{14}SGVPDRFX_1GSGSGTDFTLKIX_{15}RVX_{16}AEDX_6GX_{12}YX_{17}CX_{18}QX_{19}X_1X_{20}X_{21}PX_{22}$
$TFGX_{23}GTKLEX_{24}K$, where $X_1$ is S or T; $X_2$ is P or S; $X_3$ is L or I; $X_4$ is D or Q; $X_5$ is Q or P; $X_6$ is V or L; $X_7$ is N or D; $X_8$ is N or K; $X_9$ is E or H or N or K; $X_{10}$ is Y or L; $X_{11}$ is L

| SEQUENCES |
|---|
| or R; $X_{12}$ is I or V; $X_{13}$ is K or L; $X_{14}$ is F or D; $X_{15}$ is S or I; $X_{16}$ is K or E; $X_{17}$ is Y or F; $X_{18}$ is F or S or W; $X_{19}$ is G or S; $X_{20}$ is H or R or Q; $X_{21}$ is V or I or F; $X_{22}$ is P or F or R; $X_{23}$ is A or S or G; and $X_{24}$ is L or M or I. |

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A nucleic acid encoding a variable heavy (VH) and/or variable light (VL) region of an isolated antibody or antigen binding fragment thereof, the antibody or antigen binding fragment thereof characterized by specific binding to HcTnT-N69 (69-amino acid fragment of N-terminus of human cardiac troponin T), wherein the nucleic acid encodes:

1) a VH region comprising amino acid sequence SEQ ID NO:2, or a variant thereof having 90% or greater identity; and/or a VL region comprising amino acid sequence SEQ ID NO:3 or SEQ ID NO:6 or a variant of either thereof having 90% or greater identity;
2) a VH region comprising amino acid sequence SEQ ID NO:8, or a variant thereof having 90% or greater identity; and/or a VL region comprising amino acid sequence SEQ ID NO:9 or a variant thereof having 90% or greater identity;
3) a VH region comprising amino acid sequence SEQ ID NO:12, or a variant thereof having 90% or greater identity; and/or a VL region comprising amino acid sequence SEQ ID NO:13, SEQ ID NO:16, SEQ ID NO:18, SEQ ID NO:20, or a variant of any thereof having 90% or greater identity;
4) a VH region comprising amino acid sequence SEQ ID NO:2, or a conservative substitution variant thereof; and/or a VL region comprising amino acid sequence SEQ ID NO:3 or SEQ ID NO:6 or a conservative substitution variant of either thereof;
5) a VH region comprising amino acid sequence SEQ ID NO:8, or a conservative substitution variant thereof;

and/or a VL region comprising amino acid sequence SEQ ID NO:9 or a conservative substitution variant thereof;
6) a VH region comprising amino acid sequence SEQ ID NO:12, or a conservative substitution variant thereof; and/or a VL region comprising amino acid sequence SEQ ID NO:13, SEQ ID NO:16, SEQ ID NO:18, SEQ ID NO:20, or a conservative substitution variant of any thereof, wherein the conservative substitution variant of any of SEQ ID NOs. 2, 3, 6, 8, 9, 12, 13, 16, 18, and 20 comprises at least one substitution of an acidic, basic, aliphatic, or aromatic amino acid with a different acidic, basic, aliphatic, or aromatic amino acid, respectively;
7) a VH region comprising complementarity determining region (CDR) 1 consisting of amino acid (aa) 18 to aa 28 of SEQ ID NO:2, CDR 2 consisting of aa 43 to aa 52 of SEQ ID NO:2 and CDR 3 consisting of aa 92 to aa 96 of SEQ ID NO:2;
and/or a VL region comprising CDR 1 consisting of aa 21 to aa 31 of SEQ ID NO:3, CDR 2 consisting of aa 43 to aa 52 of SEQ ID NO:3 and CDR 3 consisting of aa 86 to aa 93 of SEQ ID NO:3;
and/or CDR 1 consisting of aa 21 to aa 31 of SEQ ID NO:6, CDR 2 consisting of aa 43 to aa 52 of SEQ ID NO:6 and CDR 3 consisting of aa 86 to aa 93 of SEQ ID NO:6;
8) a VH region comprising CDR 1 consisting of aa 18 to aa 28 of SEQ ID NO:8, CDR 2 consisting of aa 43 to aa 52 of SEQ ID NO:8 and CDR 3 consisting of aa 90 to aa 96 of SEQ ID NO:8;
and/or a VL region comprising CDR 1 consisting of aa 21 to aa 31 of SEQ ID NO:9, CDR 2 consisting of aa 43 to aa 52 of SEQ ID NO:9 and CDR 3 consisting of aa 86 to aa 93 of SEQ ID NO:9; or
9) a VH region comprising CDR 1 consisting of aa 18 to aa 28 of SEQ ID NO:12, CDR 2 consisting of aa 41 to aa 59 of SEQ ID NO:12 and CDR 3 consisting of aa 92 to aa 102 of SEQ ID NO:12;
and/or a VL region comprising CDR 1 consisting of aa 21 to aa 31 of SEQ ID NO:13, CDR 2 consisting of aa 43 to aa 52 of SEQ ID NO:13 and CDR 3 consisting of aa 86 to aa 93 of SEQ ID NO:13;
and/or CDR 1 consisting of aa 21 to aa 31 of SEQ ID NO:16, CDR 2 consisting of aa 43 to aa 52 of SEQ ID NO:16 and CDR 3 consisting of aa 86 to aa 93 of SEQ ID NO:16;
and/or CDR 1 consisting of aa 21 to aa 31 of SEQ ID NO:18, CDR 2 consisting of aa 43 to aa 52 of SEQ ID NO:18 and CDR 3 consisting of aa 86 to aa 93 of SEQ ID NO:18;
and/or CDR 1 consisting of aa 21 to aa 31 of SEQ ID NO:20, CDR 2 consisting of aa 43 to aa 52 of SEQ ID NO:20 and CDR 3 consisting of aa 86 to aa 93 of SEQ ID NO:20.

2. The nucleic acid of claim 1 comprising a sequence selected from the group consisting of: SEQ ID NO:4, SEQ ID NO:5, SEQ ID NO:7, SEQ ID NO:10, SEQ ID NO:11, SEQ ID NO:14, SEQ ID NO:15, SEQ ID NO:17, SEQ ID NO:19, SEQ ID NO:21, and a variant of any thereof.

3. A hybridoma comprising a nucleic acid of claim 1 and producing a monoclonal antibody comprising the encoded variable heavy (VH) and/or variable light (VL) region and characterized by specific binding to HcTnT-N69.

* * * * *